(12) United States Patent
Pankiewicz et al.

(10) Patent No.: US 6,326,490 B1
(45) Date of Patent: Dec. 4, 2001

(54) TETRAPHOSPHONATE BICYCLIC TRISANHYDRIDES

(75) Inventors: Krzysztof W. Pankiewicz; Krystyna Lesiak; Kyoichi A. Watanabe, all of Gaithersburg, MD (US)

(73) Assignee: Pharmasset, Ltd., Atlanta, GA (US)

( * ) Notice: Subject to any disclaimer, the term of this patent is extended or adjusted under 35 U.S.C. 154(b) by 0 days.

(21) Appl. No.: 08/949,180

(22) Filed: Oct. 10, 1997

Related U.S. Application Data

(60) Provisional application No. 60/028,154, filed on Oct. 9, 1996, and provisional application No. 60/038,360, filed on Feb. 13, 1997.

(51) Int. Cl.[7] .......................... C07H 19/04; C07H 19/16; C07H 19/20; C07D 473/34
(52) U.S. Cl. ................... 536/26.3; 536/26.2; 536/26.23; 536/26.24; 536/26.72; 536/26.74; 536/27.21; 536/27.3; 536/27.6; 536/27.7; 536/28.53; 536/29.2; 544/276; 544/277; 544/265; 558/87; 558/155
(58) Field of Search .................................. 536/26.3, 26.2, 536/26.23, 26.24, 26.72, 26.74, 27.21, 27.3, 27.6, 27.7, 28.53, 29.2; 544/276, 277, 265; 558/87, 155

(56) References Cited

U.S. PATENT DOCUMENTS

| | | | |
|---|---|---|---|
| 5,442,101 | 8/1995 | Hanhijarvi et al. | 562/10 |
| 5,569,650 | * 10/1996 | Watanabe et al. | 514/43 |
| 5,658,890 | 8/1997 | Pankiewicz, K.W. et al. | 514/43 |
| 5,700,786 | * 12/1997 | Watanabe et al. | 514/47 |

FOREIGN PATENT DOCUMENTS

| | | |
|---|---|---|
| 4341161 | 6/1995 | (DE) . |
| WO 94/29331 | 12/1994 | (WO) . |
| WO 96/00585 | 1/1995 | (WO) . |
| WO 98/15563 | 10/1997 | (WO) . |

OTHER PUBLICATIONS

Glonek, T. et al. "Full anhydrization of methylenediphosphonic acid and of phosphoric acids by a carbodiimide" Inorg.Chem., 1975, vol. 14 (7); 1597–602, XP000907002.

Lipka et al. "Synthesis of Methylene–bridged Analogues of Nicoamide Riboside, Nicotinamide Mononucleotide and Nicotinamide Adenine Dinucleotide" Nucleotides and Nucleotides, 1996, vol. 15, 149–165.

Marquez et al., "Thiazole–4–carboxamide Adenine Dinucleotide (TAD). Analogues Stable to Phosphodiesterase Hydrolysis" J. Med. Chem., 1986, vol. 29 (9), 17626–1731.

Pankiewicz K. W. et al. "Synthesis of methylenebis(phosphonate) analogs of ADP Ribose" Collect. Czech. Chem. Commun. (Sep. 23, 1996), vol. 61, S92–S–95, XP002139837.

Pankiewicz K. W. et al. "Efficient synthesis of methylenebis(phosphonate) analogues of P1,P2–disubtituted phyrophospates of biological interest" (Apr. 15, 1997), vol. 119, 3691–3692.

\* cited by examiner

*Primary Examiner*—Ba K. Trinh
(74) *Attorney, Agent, or Firm*—Sherry M. Knowles; Clark G. Sullivan; King & Spalding

(57) ABSTRACT

Disclosed are novel bicyclic tris(anhydride)s useful as intermediates in the synthesis of biolologically active compounds, and the compounds which may be synthesized from such intermediates.

28 Claims, No Drawings

TETRAPHOSPHONATE BICYCLIC TRISANHYDRIDES

CROSS REFERENCE TO RELATED APPLICATIONS

This application is a continuation-in-part of application Ser. No. 60/028,154 filed Oct. 9, 1996, and of application Ser. No. 60/038,360 filed Feb. 13, 1997.

BACKGROUND OF THE INVENTION

1. Field of the Invention

The present invention relates to novel bicyclic tris (anhydride)s (BTAS) useful as intermediates in the synthesis of biologically active compounds, and the compounds which may be synthesized from such intermediates.

2. Description of Related Art $P^1,P^2$-disubstituted pyrophospate derivatives play an important role in a variety of biochemical transformations. For example, nicotinamide adenine dinucleotide (NAD) and flavin adenine dinucleotide (FAD) serve as the major electron carriers in biological dehydrogenations, whereas another pyrophosphate, coenzyme A (CoA), is a universal carrier of acyl groups. Cytidine diphosphodiacylglycerol (CDP-diacylglycerol), cytidine diphosphocholine (CDP-choline) and cytidine diphosphoethanolamine (CDP-ethanolamine) are activated intermediates in the de novo synthesis of various phospholipids. UDP-glucose, UDP-galactose as well as some purine dinucleotide sugars such as GDP-mannose serve as cofactors in many sugar transfer processes. Finally, mono- and poly(ADP-ribose) derivatives which modulate the function of proteins, as well as cyclic ADP-ribose which influences calcium metabolism, also contain the pyrophosphate moiety.

It has long been sought to develop a simple method to synthesize isosteric methylenebis(phosphonate) analogues of the above biologically important $P^1,P^2$-disubstituted pyrophosphates, because such analogues, in which the pyrophosphate oxygen is replaced by a methylene group, preserve the shape, size and electronic charge of the n atural counterpart significantly, and provide derivatives with modified biochemical properties at a particular site. For example, in contrast to the pyrophosphate bond ($P^1$—O—$P^2$), the $P^1$—CH—$P^2$ linkage o f methylenebis(phosphonate)s cannot be hydrolyzed by the enzymes that cleave the pyrophosphate bond. Another advantage of phosphonates as phosphate mimics is their ability to penetrate cell membranes (Miller and Tso, *Anti-Cancer Drug Design*, 1987, 2, 117; Bergstrom, et al., *Nucleosides, Nucleotides*, 1987, 6, 53; Bergstrom and Shum, *J. Org. Chem.*, 1988, 53, 3953).

Currently, no practical method is available for the synthesis of $P^1,P^2$-disubstituted methylenebis(phosphonate) analogues of natural cofactors and ADP-ribose derivatives. only a few such compounds have been synthesized in low yields after lengthy and tedious processes. For example, methylenebis(phosphonate) analogues of ADP-glucose, UDP-galactose, and GDP-mannose were prepared as potential inhibitor s of glycosyl transferase. Activation of the corresponding pyranosyl-1-methylenebis (phosphonate) with 1-(mesitylene-2-sulfonyl)-3-nitro-1,2,4-triazole (MSTN) and coupling with an appropriate nucleoside derivative afforded the desired compounds only in moderate yields (32–48%) which made the isolation of pure compounds a rather difficult and time consuming process (Vaghefi, et al., *J. Med. Chem.* 1987, 30, 1391). The methylenebis(phosphonate) analogue of tiazole-4-carboxamide adenine dinucleotide, β-methylene-TAD, was synthesized in 36% yield by dicyclohexylcarbodiimide (DCC) catalyzed coupling of protected tiazofurin with adenosine 5'-methylene bis(phosphonate). Again, purification of this compound from the mixture was quite cumbersome. It was found that β-methylene TAD is a potent inhibitor of inosine monophosphate dehydrogenase (IMPDH) (Marquez, et al., *J. Med. Chem.* 1986, 29, 1726).

Inosine monophosphate dehydrogenase (IMPDH) catalyzes the NAD dependent conversion of inosine 5' monophosphate (IMP) to xanthosine monophosphate. Two forms of the enzyme are found in mammalian cells, each encoded by distinct cDNAs (Natsumeda, Y. et al., *J. Biol. Chem.*, 1990,265, 5292–5295). Type I is expressed constitutively, while the levels of type II are markedly increased in tumor cells and activated lymphocytes. Conversely, when tumor cells are induced to differentiate, transcripts of type II decline to below those of type I.

Mycophenolic acid (MPA) is the most potent inhibitor of IMPDH (Carr, et al. *J. Biol. Chem.* 1993, 268, 27286–27290). It blocks B and T lymphocyte proliferation and has been used as an immunosuppressant (Wu, J. C. In *Perspectives in Drug Discovery and Design*, Wyvratt, M. J.; Sigal, N. H., Eds.; ESCOM Science Publ., Leiden, 1994, Vol. 2, pp 185–204), although it is inactive against tumors due to its quick conversion into the inactive β-glucuronide after administration (Franklin, et al. *Cancer Res.*, 1996, 56, 984–987). MPA inhibits IMPDH with even better specificity against the type II isoform dominant in cancer cells ($K_i$= 6–10 nM) than type I expressed in normal cells ($K_i$=33–37 nM) (Carr, et al., loc cit.). When the MPA binds to the cofactor moiety of IMPDH, it resembles that of nicotinamide mononucleotide (NMN) with a carboxyl group positioned at the space occupied by the phosphoryl group of NMN (Sintchak, et al., *Cell*, 1996, 85, 921–930).

SUMMARY OF THE INVENTION

In one aspect, the present invention relates to a compound having the following structure:

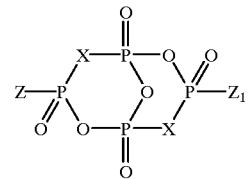

wherein

Z and $Z_1$ are the same or different and are alkyl, aralkyl, aryl, aminoalkyl, alkyloxy, aralkyloxy, alkylamino, aralkylamino, arylamino, alkylmercaptan, aralkylmercaptan, arylmercaptan, carbohydrate, nucleoside, a mycophenolic acid residue or derivative, steroid, or substituted glyceride; and X is methylene (—CH$_2$—), mono- or di-halo methylene, or —NR—, where R is H or alkyl.

In another aspect, the present invention provides a method for the preparation of a compound having the following structure:

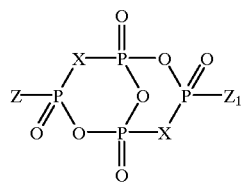

wherein

Z and $Z_1$ are the same or different and are alkyl, aralkyl, aryl, aminoalkyl, alkyloxy, aralkyloxy, alkylamino, aralkylamino, arylamino, alkylmercaptan, aralkylmercaptan, arylmercaptan, carbohydrate, nucleoside, a mycophenolic acid residue or derivative, steroid, or substituted glyceride; and X is methylene (—$CH_2$—), mono- or di-halo methylene, or —NR—, where R is H or alkyl; which method comprises reacting a compound having the following structure:

($Z_{p2}$)

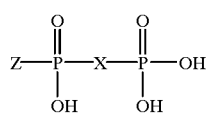

wherein Z and X are as described, with a dehydrating agent.

In another aspect, the present invention provides a method for the preparation of a compound having the following structure:

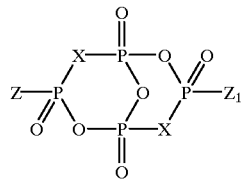

wherein

Z and $Z_1$ are the same or different and are alkyl, aralkyl, aryl, aminoalkyl, alkyloxy, aralkyloxy, alkylamino, aralkylamino, arylamino, alkylmercaptan, aralkylmercaptan, arylmercaptan, carbohydrate, nucleoside, a mycophenolic acid residue or derivative, steroid, or substituted glyceride; and X is methylene (—$CH_2$—), mono- or di-halo methylene, or —NR—, where R is H or alkyl; which method comprises reacting a compound having the following structure:

($Z_{p4}Z_1$)

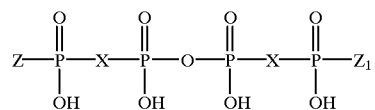

wherein Z, $Z_1$ and X are as defined above, with a dehydrating agent.

In another aspect, the present invention provides a method for the preparation of a compound having the following structure:

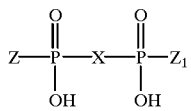

wherein

Z and $Z_1$ are the same or different and are alkyl, aralkyl, aryl, aminoalkyl, alkyloxy, aralkyloxy, alkylamino, aralkylamino, arylamino, alkylmercaptan, aralkylmercaptan, arylmercaptan, carbohydrate, nucleoside, steroid, a mycophenolic acid residue or derivative or substituted glyceride; and X is methylene (—$CH_2$—), mono- or di-halo methylene, or —NR—, where R is H or alkyl; which method comprises reacting a compound having the following structure:

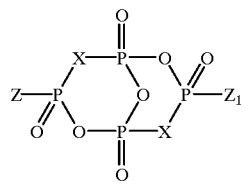

wherein Z, $Z_1$ and X are as defined above, with a nucleophilic agent.

In another aspect, the present invention provides compounds having the following structure:

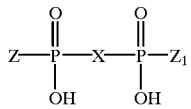

wherein

Z and $Z_1$ are the same or different and are alkyl, aralkyl, aryl, aminoalkyl, alkyloxy, aralkyloxy, alkylamino, aralkylamino, arylamino, alkylmercaptan, aralkylmercaptan, arylmercaptan, carbohydrate, nucleoside, steroid, a mycophenolic acid residue or derivative, or substituted glyceride; and X is methylene (—$CH_2$—), mono- or di-halo methylene, or —NR—, where R is H or alkyl.

In another aspect, the present invention provides compounds having the following structure:

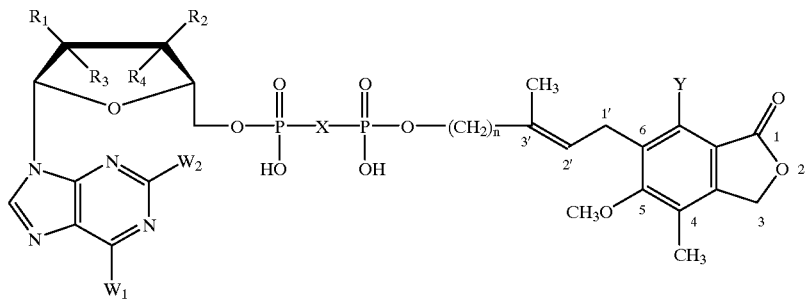

wherein each of $R_1$, $R_2$, $R_3$, and $R_4$ is independently H, OH or F;

X is O, S, mono- or di-halomethylene, or NR wherein R is H or alkyl, or $CH_2$;

Y is OH, SH or F; and each of $W_1$ and $W_2$ is independently H, OH, =O, OR, SH, SR, $NH_2$, NHR or $NR_2$, wherein R is $C_1$–$C_5$ alkyl and n is an integer from 1 to 5.

DESCRIPTION OF THE PREFERRED EMBODIMENTS

The present invention provides new, versatile intermediates for synthesis of numerous $P^1,P^2$-disubstituted methylene- and mono- or difluoro- or amino-methylene-bis (phosphonate)s of biological importance. The intermediate compounds may be prepared by action of a dehydrating agent on a $P^1$-mono-substituted phosphonomethylenephosphonate (Z—$P^1$—$CH_2$—$P_2$—OH or $ZP_2$) having the following structure:

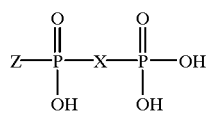
(Zp2)

wherein Z is aralkyl, aryl, aminoalkyl, alkyloxy, aralkyloxy, alkylamino, aralkylamino, arylamino, alkylmercaptan, aralkylmercaptan, arylmercaptan, carbohydrate, nucleoside, steroid, or substituted glyceride; and x is methylene (—$CH_2$—), mono- or di-halo methylene, or —NR—, where R is H or alkyl. There are many suitable dehydrating agents which would be apparent to one of ordinary skill. Preferred dehydrating agents include carbodiimides, particularly 1,3-dicyclohexylcarbodiimide (DCC) or 1,3-diisopropylcarbodiimide.

The intermediates of the present invention may also be prepared by dehydration of a $P^1,P^4$-disubstituted-$P^1$:$P^2$, $P^2$:$P^4$-dimethylene tetrakis(phosphonic) anhydride (Z—$P^1$—$CH_2$—$P^2$—O—$P^3$—$CH_2$—$P^4$—$Z_1$ or $Zp_4Z_1$) having the following structure:

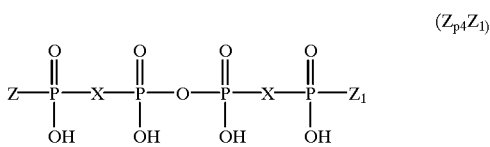
($Z_{p4}Z_1$)

wherein Z and $Z_1$ are the same or different and are alkyl, aralkyl, aryl, aminoalkyl, alkyloxy, aralkyloxy, alkylamino, aralkylamino, arylamino, alkylmercaptan, aralkylmercaptan, arylmercaptan, carbohydrate, nucleoside, a mycophenolic acid residue or derivative, steroid, or substituted glyceride; and X is methylene (—$CH_2$—), mono- or di-halo methylene, or —NR—, where R is H or alkyl.

The above $Zp_4Z_1$ analogues can be prepared from the corresponding methylenebis(phosphonate)s ($Zp_2$ or $Z_1p_2$) by reaction with a dehydrating agent, such as DCC, to give a symmetrical $Zp_4Z$ or $Z_1p_4Z_1$. Alternatively, the $Zp_2$ can be activated with imidazole and reacted with $Z_1p_2$ to give an unsymmetrical derivative $Zp_4Z_1$:

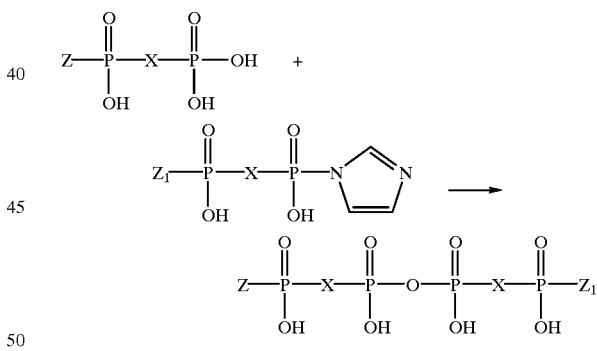

Such an unsymmetrical tetrakis(phosphonate) analogue can be further dehydrated to give the corresponding mixed bicyclic tris(anhydride), BTA, which upon reaction with an appropriate nucleophilic reagent $Z_2$ gives two different pyrophosphate analogues: $Zp_2Z_2$ and $Z_1p_2Z_2$.

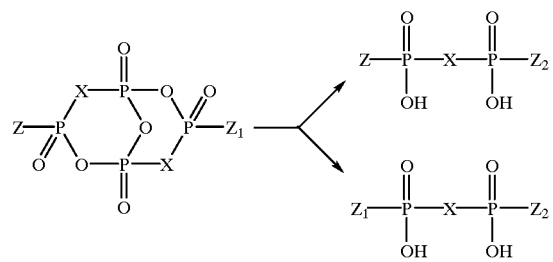

wherein $Z_2$ is aralkyl, aryl, aminoalkyl, alkyloxy, aralkyloxy, alkylamino, aralkylamino, arylamino, alkylmercaptan, aralkylmercaptan, arylmercaptan, carbohydrate, nucleoside, a mycophenolic acid residue or derivative, steroid, or substituted glyceride; and X is as described above.

During the course of studies on the reaction of 2′,3′-O-isopropylideneadenosin-5′-ylphosphonomethylenephosphonic acid (1, Scheme 1) with DCC, the inventors developed a very unique intermediate with the bicyclic[3.3.1] system (4) which is highly susceptible to nucleophilic attack to produce readily a number of $P^1,P^2$-disubstituted methylenebis (phosphonate)s. Scheme 1 exemplifies the synthesis of a $P^1$-(adenosin-5′-yl)-$P^2$-(benzyl β-D-ribofuranosid-5-yl)-methylenebis(phosphonate) derivative 7 in very high yield with a novel mechanism.

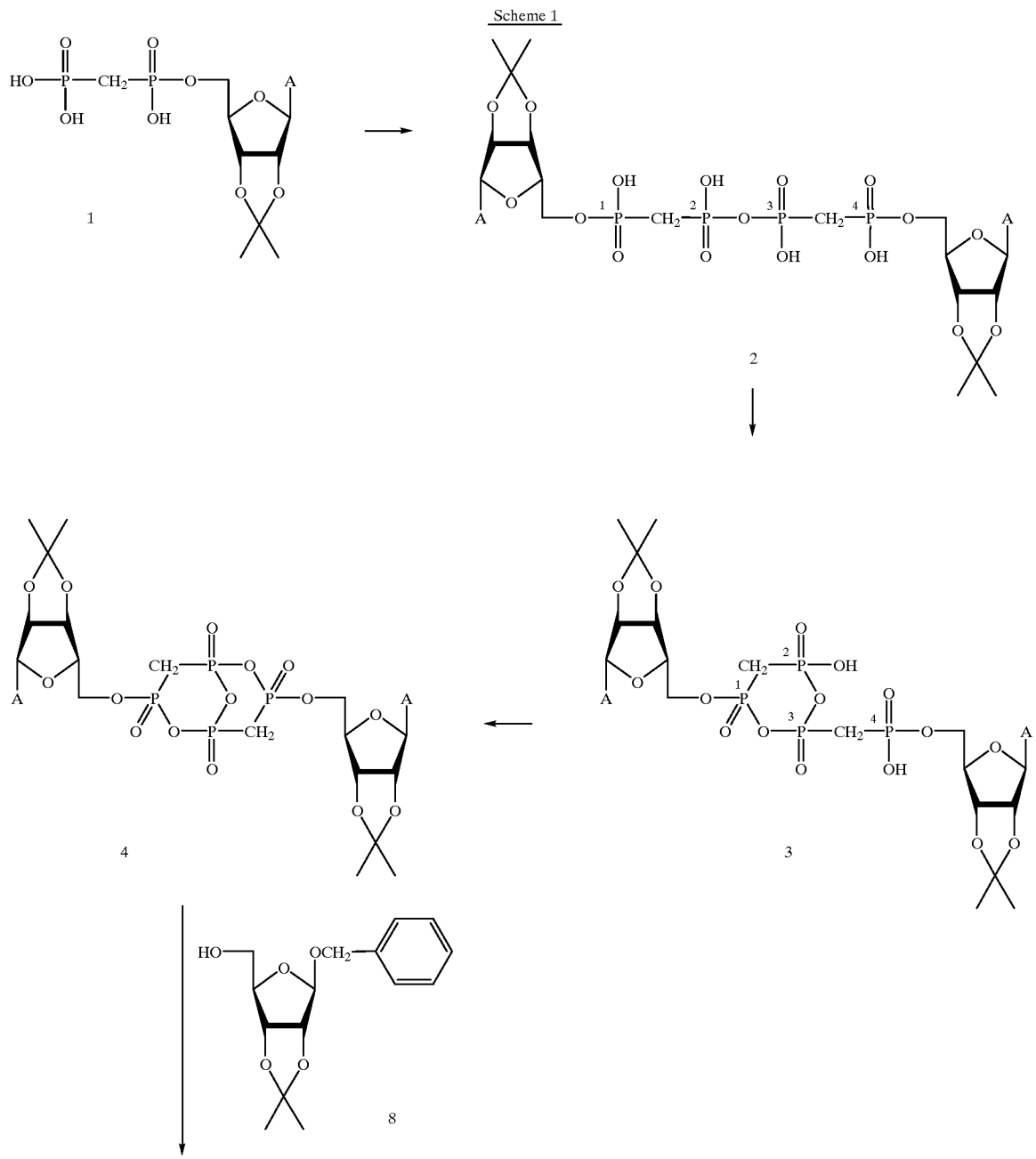

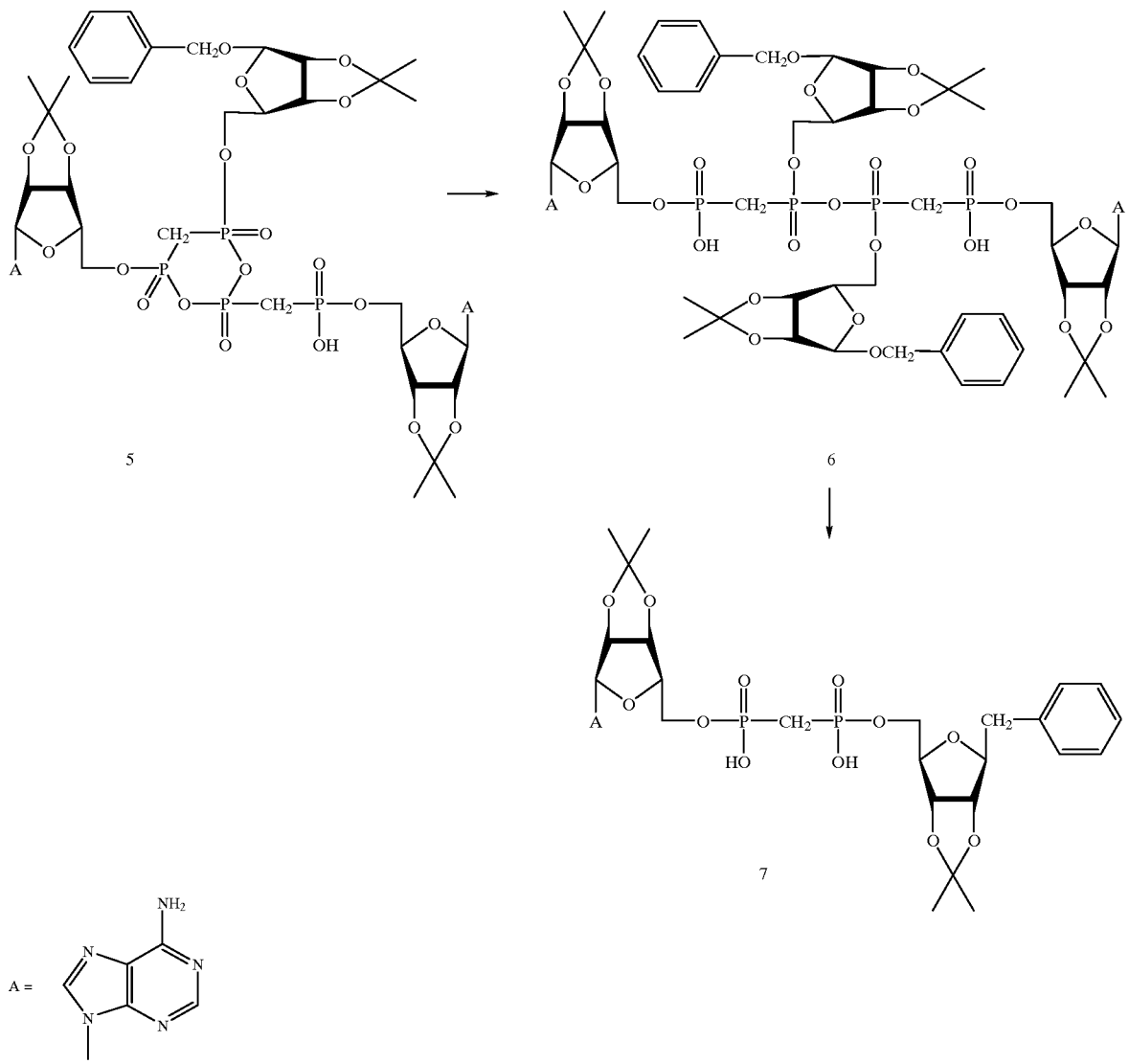

Reaction of (1, Ap$_2$) with DCC afforded bis(2',3'—O-isopropylidene-adenosine-5'-phosphonomethylenephosphonyl) anhydride (2), an analogue of P$^1$,P$^4$-diadenosine tetraphosphate (Ap$_4$A) which was reported by Blackburn et al. (Blackburn, G. M.; Guo, M-J.; McLennan, A. G. in "Ap$_4$A and Other Dinucleoside Polyphosphates", McLennan, A. G. ed., CRC Press, Inc., Boca Raton, 1994, Chapter 11, pp. 313–314). However, when 3–4 equivalents of DCC were used, it was discovered that P$^1$,P$^3$-dehydration of 2 took place leading to the formation of cyclic anhydride 3. Moreover, further dehydration between P$^2$ and P$^4$ occurred surprisingly to give rise to bicyclic trisanhydride (BTA) 4. Such BTA could be also prepared from isolated Ap$_4$A analogue 2. The uncharged BTA 4 could not be isolated due to its susceptibility to hydrolysis. However, its presence could be detected by $^{31}$P NMR. Thus, the $^{31}$P NMR spectrum of 4 contained multisignal resonances in three broad regions of d −0.5–2.2, 6.0–8.0, and 12.8–17.6 ppm. Since all four phosphorus atoms in the structure of 4 are chiral, such multisignal resonances should be expected. The non-equivalence of phosphorus atoms P$^1$ and P$^4$ in the bicyclic structure of 4 is further extended due to substitution on P$^1$ and P$^4$ by the chiral adenosyl moiety. All these characteristics contribute to such complicated phosphorus NMR feature.

The assignment of the structure of BTA 4 was further confirmed by its hydrolysis with H$_2$$^{18}$O to the corresponding Ap$_4$A analogue 2 and further to the starting monoester of methylenebis(phosphonic) acid 1. These compounds were separated by preparative HPLC and subjected to MS (ES) analyses. The molecular weight of 2 was established as 916 by the presence of the M−H ion at m/z 915 and doubly charged (M−2H)$^{-2}$ at m/z 457. Thus, the conversion of 4 into 2 resulted, as expected, in incorporation of two H$_2$$^{18}$O molecules. The MS of monoester of methylenebis (phosphonic acid) 1 indicated the incorporation of one or two $^{18}$O atoms by the presence of M−H ion at m/z 466 and 468.

The chemical reactivity of BTA 4 also confirmed its structure assignments. Reaction of 4 with benzyl 2,3-O-isopropylidene-β-D-ribofuranoside 8 occurred smoothly due to the uncharged BTA 4. Thus, the corresponding ester of P$^1$, P$^2$, P$^3$, P$^4$-bis(methylenebisphosphonate) analogue of Ap$_4$A (6) was detected as a single product by $^{31}$P NMR. The multisignal resonances of 4 collapsed into two broad signals of 6 showing the characteristic AA'XX' system of Ap$_4$A analogues. Such reactivity can be explained by the greater susceptibility of phosphorus atoms $P^2$ and $P^3$ than $P^1$ and $P^4$ in the bicyclic structure of 4 to nucleophilic attack. Indeed, this should be expected since not only do adenosine moieties provide steric hindrance for $P^1$ and $P^4$ but also electronic effects favor attacking the $P^2$ and $P^3$ atoms rather than $P^1$ and $P^4$. The $P^2$ and $P^3$ phosphorus atoms of 4 are connected through the pyrophosphate bond to each other and to the $P^4$ and $P^1$, respectively, through the second pyrophosphate linkage. Therefore, the $P^2$ and $P^3$, which participate in the formation of such phosphorus bisanhydride, are more electron deficient (i.e., more susceptible to nucleophilic attack) than the corresponding $P^1$ and $P^4$ atoms linked to adenosine via ester bond. The stoichiometry of 4 to 6 conversion shows that substitution of phosphorus $P^2$ (alternatively $P^3$) should result in the formation of intermediate 5 by breaking the $P^2$—O—$P^4$ (or $P^1$—O—$P^3$) pyrophosphate bond rather than $P^2$—O—$P^3$ linkage. The pyrophosphate bond $P^2$—O—$P^3$ in 5 is left intact to allow the second nucleophilic attack of 8 on still uncharged phosphorus atom $P^3$ of 5 to give derivative 6. Alternatively, the concerted attack on $P^2$ and $P^3$ atoms would also give derivative 6 (see Scheme 1).

After hydrolysis with water, two equivalents of the desired ADP-ribose derivative 7 were obtained from one molecule of 6 in almost quantitative yield. Gram amounts of ADP-ribose derivative 7 can be obtained by this procedure since the crude product does not require HPLC purification.

The same ADP-ribose 7 can be obtained by activation of benzyl 2,3-O-isopropylidene β-D-ribofuranosid-5-yl-phosphonomethylenephosphonic acid (9) with DCC followed by reaction with 2',3'-O-isopropylidene-adenosine (11). The active intermediate is now BTA 10.

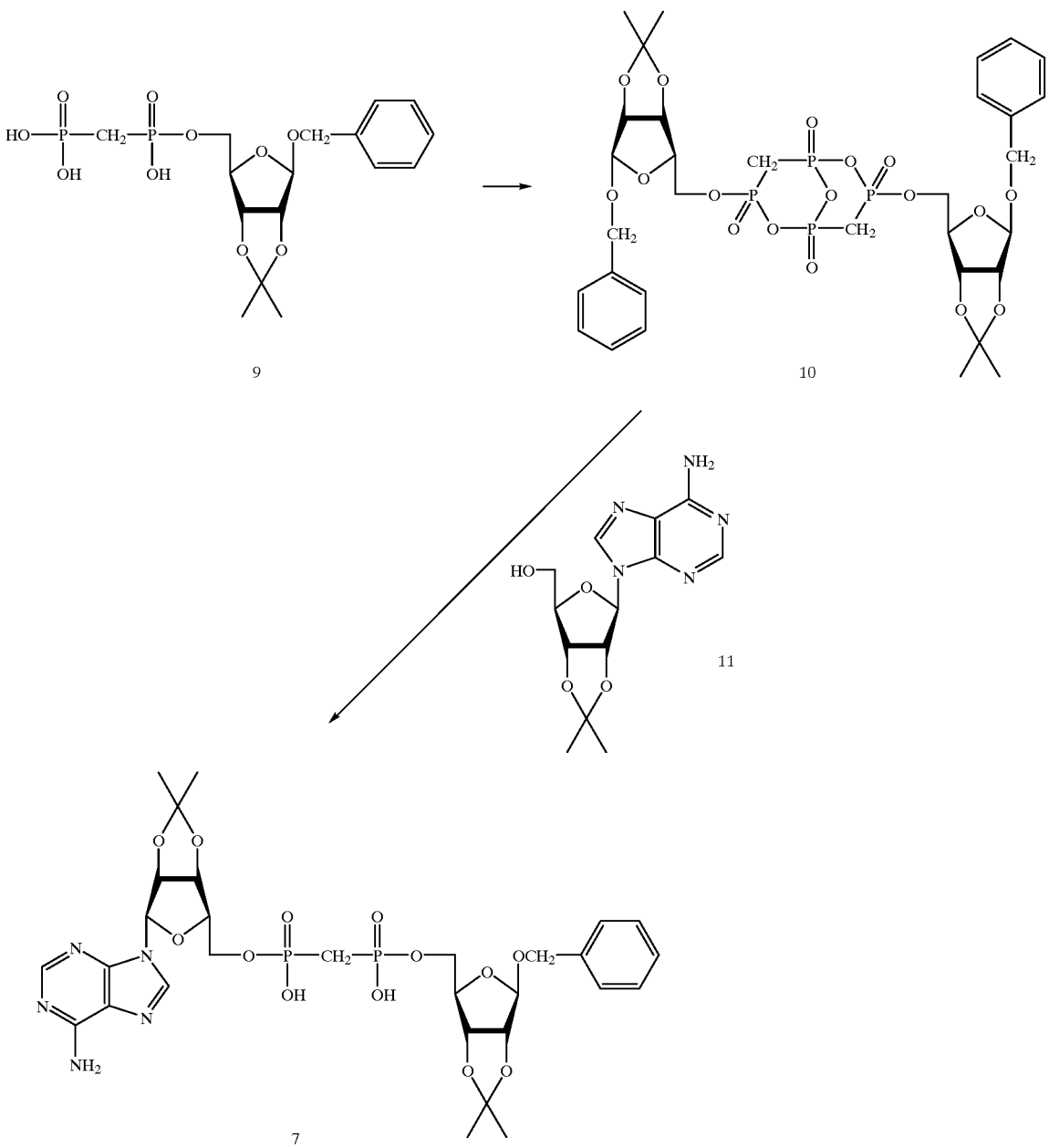

In a similar manner the reaction of BTA 4 with 2,3-O-isopropylidene D-ribonolactone 12 afforded the methylene-bis(phosphonate) analogue of ADP-ribonolactone 13. ADP-ribonolactone is the known transition state inhibitor of ADP-ribosylation.

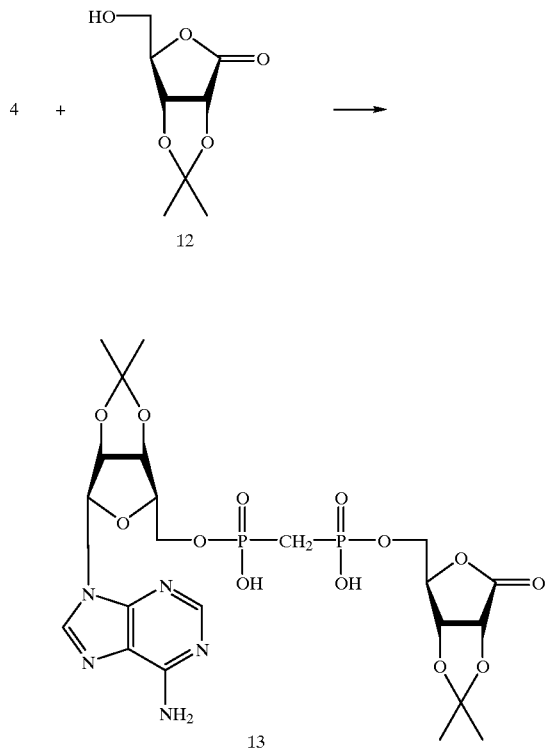

In a similar manner riboflavine (14) reacted with BTA 4 to give the corresponding methylenebis(phosphonate) analogue of flavin adenine dinucleotide (FAD).

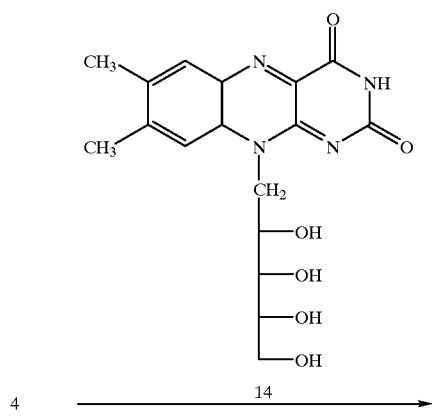

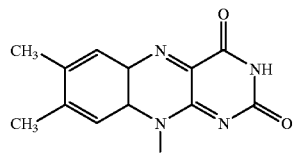

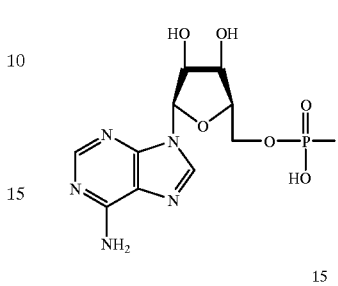

Similarly, reaction of BTA 4 with pantothenic acid derivative (16) afforded the methylenebis(phosphonate) analogue related to dephospho CoA (17).

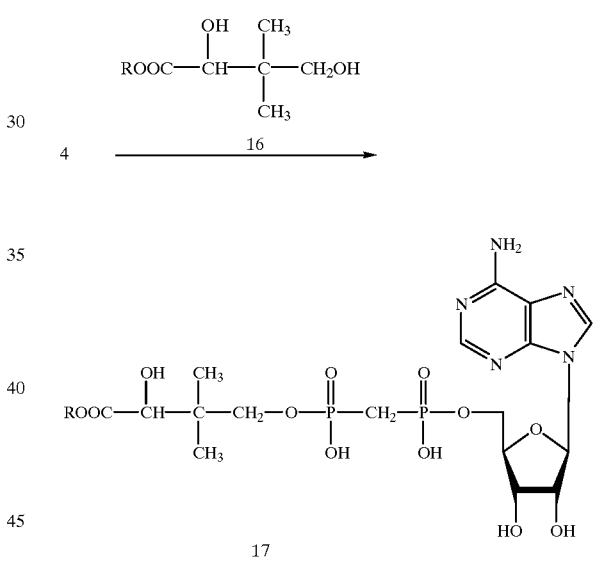

The formation of such BTAs is not limited to 4 or 10. Virtually any monosubstituted methylenebis(phosphonate) $Zp_2$ (wherein Z can be alkyl, alkyloxy, carbohydrate, nucleoside, terpene, etc.) or the tetraphosphate analogue $Zp_4Z$ (Z defined above) can be converted into the corresponding BTA. For example, 2',3'-O-isopropylidene-N-acetylcytidin-5'-yl-methylenebis(phosphonate) (18) was converted into the corresponding BTA (19) which upon reaction with N-acetylethanolamine (20) afforded the methylenebis(phosphonate) analo of CDP-ethanolamine 21.

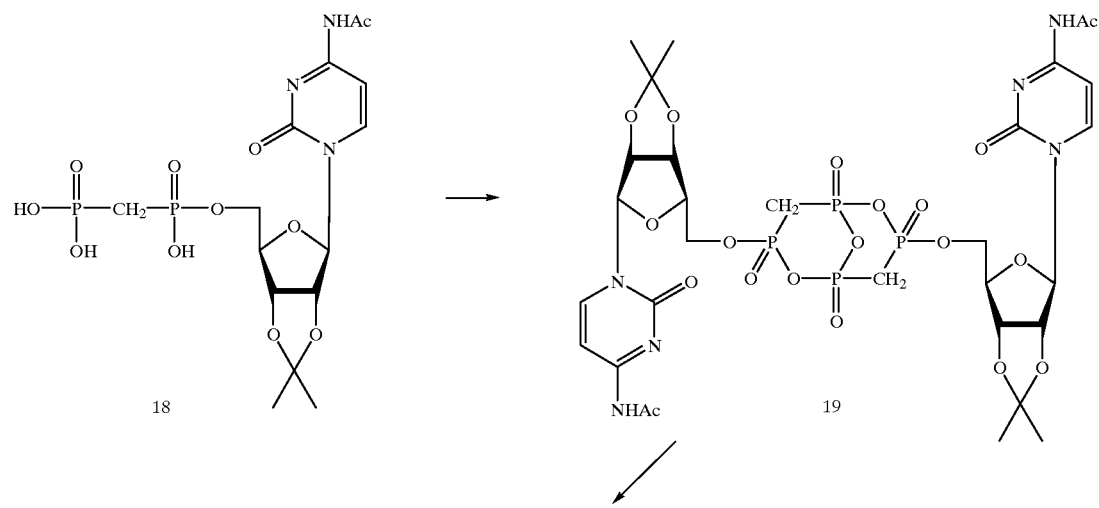
Similar reaction of BTA 19 with diacylglycerol 22 yielded the corresponding CDP-diacylglycerol analogue 23.
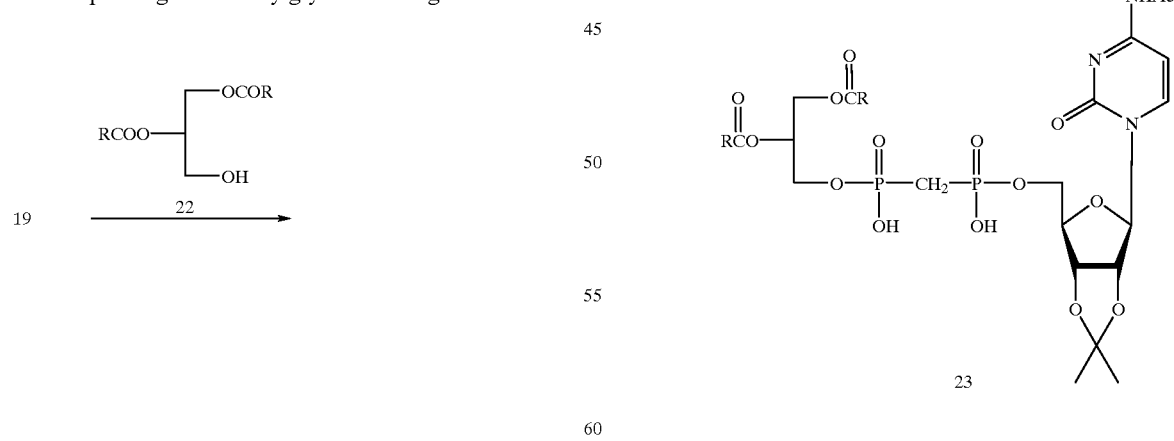
-continued The formation of BTAs is not limited to methylene bisphosphonates. A similar dehydratation was found to occur with difluoromethylenebis(phosphonate)s. For example, 2',3'-O-isopropylidene-tiazofurin-5'-yl-difluoromethylenebis(phosphonate) (24) was converted into the corresponding BTA 25, which on treatment with adenosine derivative 11 produced the analogue of TAD 26.

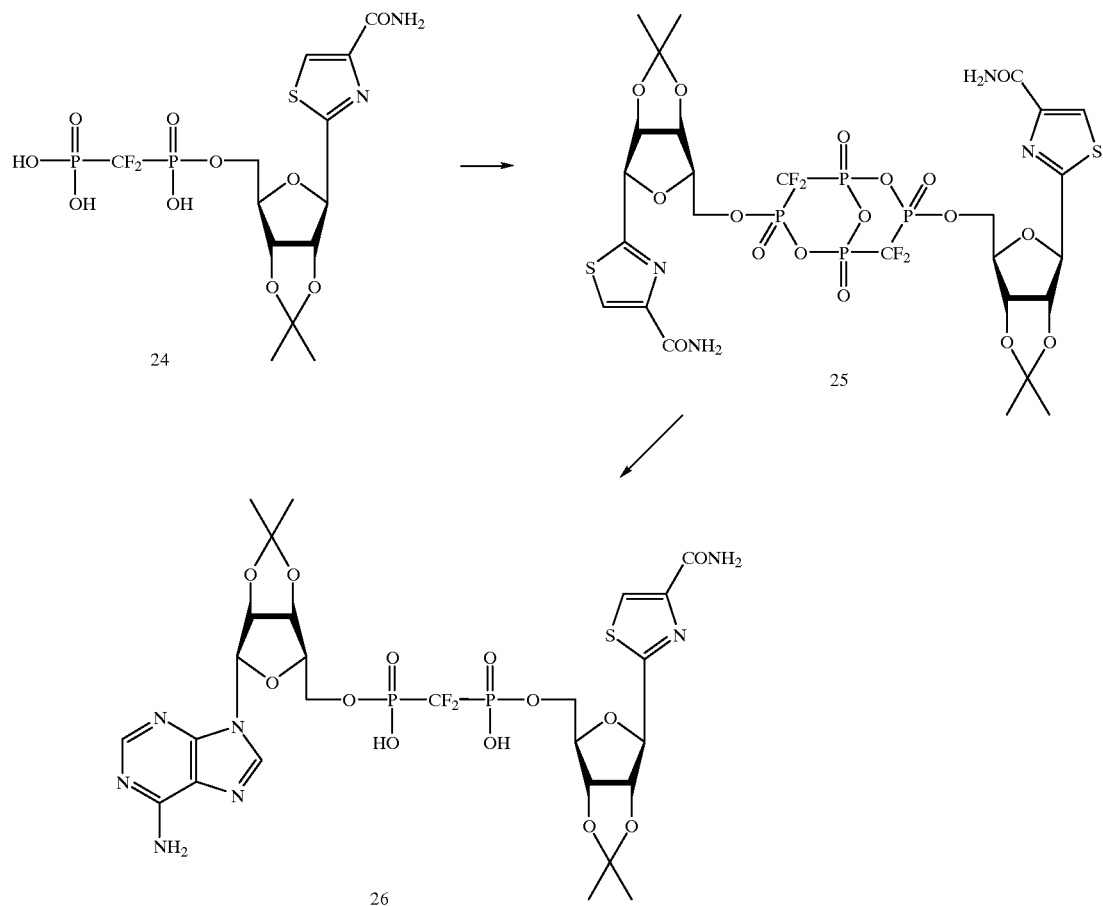

Utilization of BTAs is not limited to reactions with a variety of compounds containing hydroxyl group (R—OH), leading to the formation of methylene- or difluoromethylenebisphosphonates of biological interest as will be shown in the examples. Virtually, any nucleophilic reagent, such as Ph—OH, Ph—SH, R—SH, R—NH$_2$, R$_2$NH, etc. reacts with BTAs to give the corresponding P$^1$,P$^2$-disubstituted bis(phosphonate)s.

Also, reaction of BTAs with phosphoric, phosphonic, and phosphinic acid derivatives give the corresponding triphospate analogues:

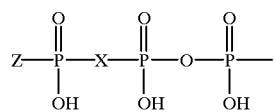

Utilization of BTAs is not limited to intermolecular reactions. Intramolecularly attached nucleophilic groups can also participate in formation of cyclic derivatives according to the principle of this invention. This is further demonstrated in Scheme 2 by the synthesis of analogues of cyclic IDP-ribose in which the ribose at N$^1$ is replaced by butanol. Thus, 2',3'-O-isopropylideneinosine (27) was alkylated with 4-bromobutyl acetate in the presence of DBU to give a 9:1 mixture of N$^1$- and O$^6$-substituted products 28 and 31, respectively. Compounds 28 and 31 were separated on a column of silica gel and then mesylated to give 5'-mesylates 29 and 32. Upon treatment with the tetrabutylammonium salt of methylenebis-(phosphonic) acid followed by deacetylation, 29 and 32 were converted into their corresponding methylenebis(phosphonate)s 30 and 33 from which the corresponding BTAs 34 and 35 were prepared as described in Example 1. Formation of BTAs was found to be much faster than the subsequent reaction with butanol attached to N$^1$ or O$^6$ of 34 and 35, respectively. Yield of the desired analogues of cyclic IDP ribose 36 and by-product 37 was 10–14%.

Scheme 2

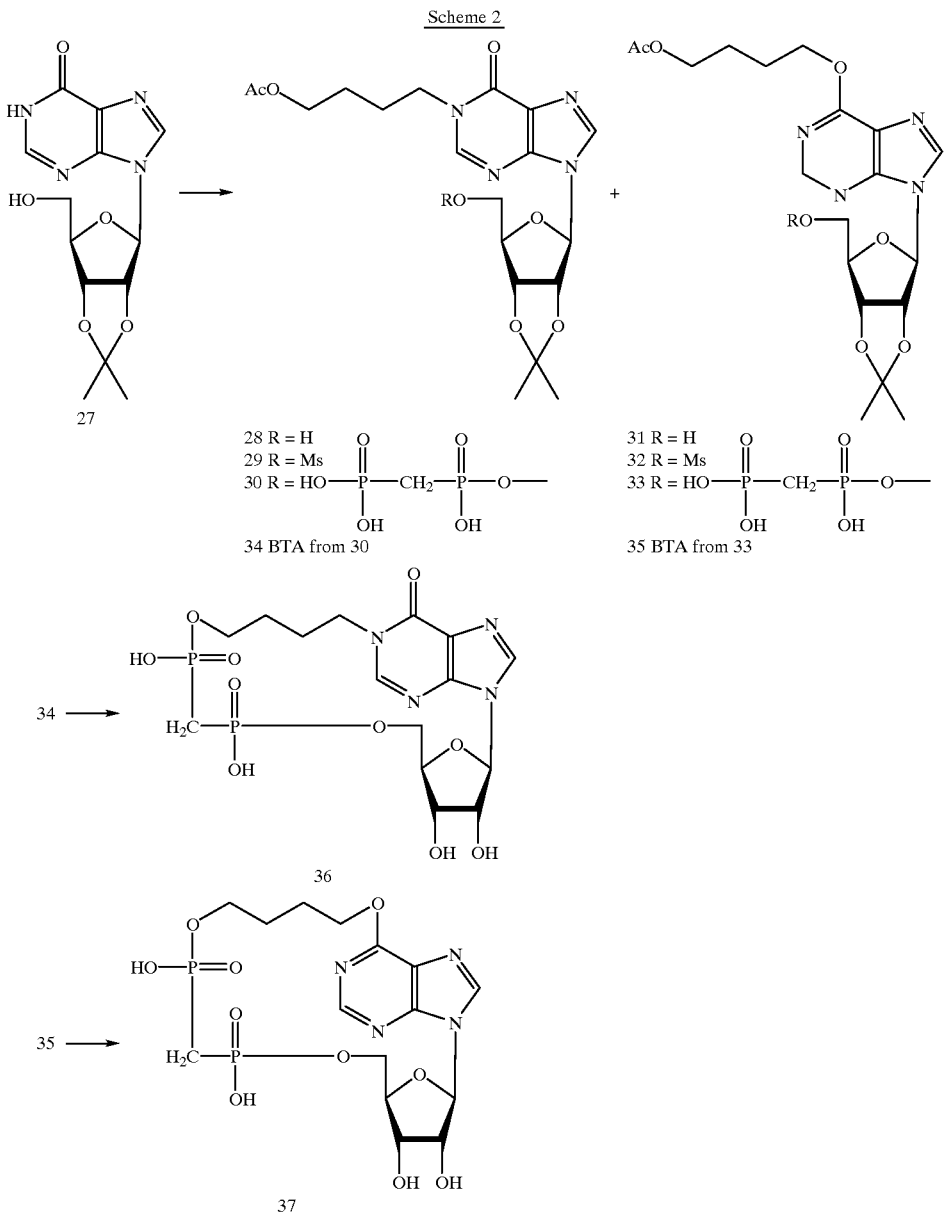

Particularly preferred compounds with the present invention include analogs of mycophenolic purine dinucleotide having the following general structure (A):

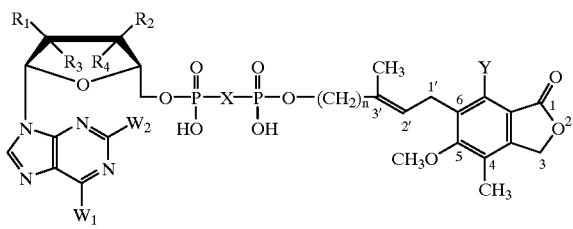

wherein
each of $R_1$, $R_2$, $R_3$, and $R_4$ is independently H, OH or F;
X is O, S, mono- or di-halomethylene, or NR wherein R is H or alkyl, or $CH_2$;
Y is OH, SH or F; and
each of $W_1$ and $W_2$ is independently H, OH, =O, OR, SH, SR, $NH_2$, NHR or $NR_2$, wherein R is $C_1$–$C_5$ alkyl and n is an integer from 1 to 5.

The mycophenolic acid derivatives (structure (A) above) of the present invention have inhibitory activity against IMPDH-II, and are resistant to inactivation by glucuronidation with various glucuronyltransferases in vitro, and also stable in plasma at room temperature for at least several days. They may thus be used as immunosuppressants, and to treat conditions associated with elevated levels of IMPDH, such as cancer, especially certain leukemias including lymphocytic leukemia or chronic granulocytic leukemia.

The structure (A) compounds of the present invention may be synthesized by linking a nucleoside-5'-methylenebis (phosphonate) to various mycophenolic alcohols (MPols) of general structure 2

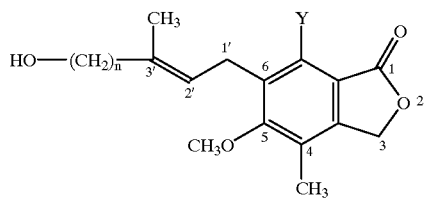

using methods disclosed herein.

Treatment of 2',3'-O-isopropylidene nucleoside 5'-methylenebis(phosphonate)s in general and the adenosine derivative 3 (Scheme 3 below) in particular with diisopropylcarbodiimide (DIC) leads to the formation of $P^1$, $P^4$-bis(adenosin-5'-yl)tetraphosphonate 4, which upon further dehydration with DIC is converted into an active intermediate 5 having the structure of bicyclic trisanhydride (Pankiewicz, K. W. et al., J. Am. Chem. Soc., 1997, 119, 3691–3695). Reaction of the bicyclic intermediate 5 with an MP-n-ol 2 gives the corresponding $P^2$, $P^3$-bis(mycophenolic alcohol-6-yl)-$P^1$, $P^4$-di-(2,3-O-isopropylidene-adenosin-5'-yl)tetraphosphonates 6 which upon hydrolysis with water and deisopropylidenation with acid afford the desired $P^1$-adenosine-5-yl, $P^2$-mycophenolic alcohol-6-yl methylenebis(phosphonate) (β-methylene MAD 1).

The structure of 1 (n=3, for example) is established by $^1H$ and $^{31}P$ NMR and MS (see Experimental Details). The resonance signal of 6' $CH_2$ of the MP-n-ol (n=3) moiety in the proton NMR of 1 at 3.79 appeared as a quartet ($J_{H-P}$=6.3 Hz and $J_{H-H}$=6.3 Hz) showing the coupling with the phosphorus atom. A heteronuclear shift correlation experiment also confirmed the phosphorus-6'$CH_2$ coupling.

Scheme 3

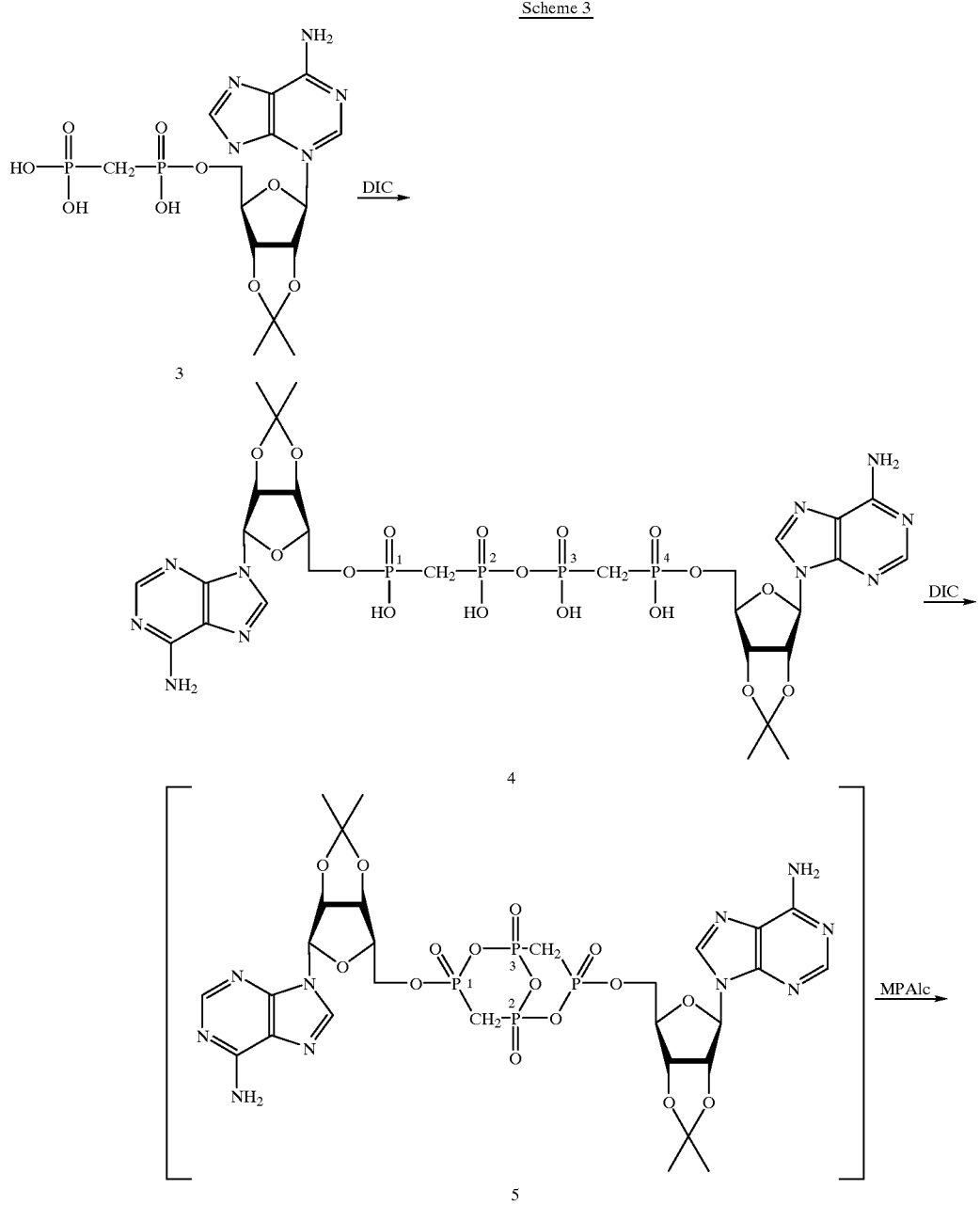

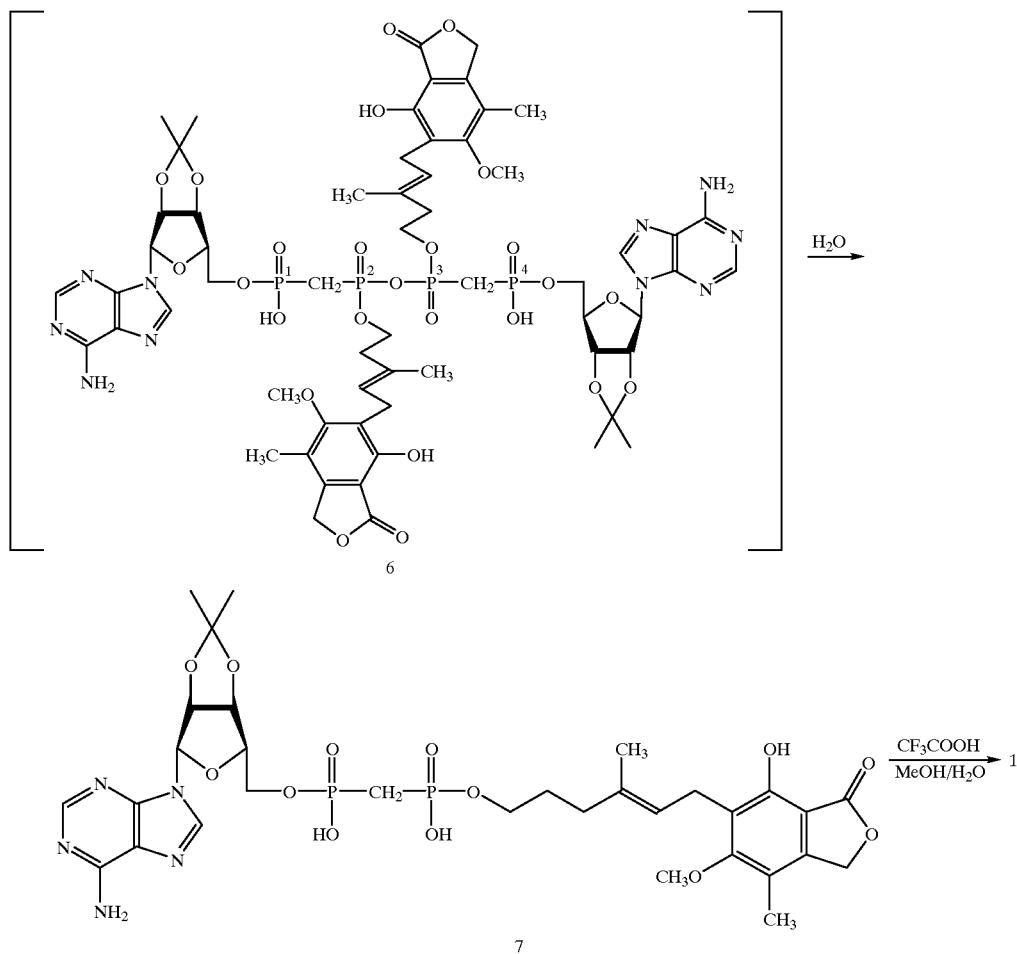

R = MPAlc-6'-yl

The compounds of structure 1 are stable in plasma at room temperature for at least several days. It is assayed for both inhibitory activity against human IMPDH type II and for anti-proliferative activity against K562 erythroleucemic cells. The $IC_{50}$ values are measured in the presence of 100 $\mu$M NAD, 50 $\mu$M IMP, 100 nM Tris-HCl, 100 mM KCl, 3 mM EDTA, and 25 nM enzyme at pH 8.0. The ability to induce differentiation in K562 cells is also estimated by determining the fraction of benzidine positive cells converted following incubation with β-methylene-MAD. It is found that this compound is a potent inhibitor of IMPDH type II with $K_i$=0.3 $\mu$M as well as growth of K562 cells with $IC_{50}$=6 $\mu$M. In addition, this compound was found to be completely resistant to glucuronidation by various glucuronosyltransferases in contrast to mycophenolic acid which is effectively glucuronidated in parallel experiments.

Compounds within the present invention will have biological activity and thus may be administered to patients in need thereof. For therapeutic or prophylactic treatment, the compounds of the present invention may be formulated in a pharmaceutical composition, which may include, in addition to an effective amount of active ingredient, pharmaceutically acceptable carriers, thickeners, diluents, buffers, preservatives, surface active agents and the like. Pharmaceutical compositions may also include one or more other active ingredients if necessary or desirable.

The pharmaceutical compositions of the present invention may be administered in a number of ways as will be apparent to one of ordinary skill. Administration may be done topically, orally, by inhalation, or parenterally, for example.

Topical formulations may include ointments, lotions, creams, gels, drops, suppositories, sprays, liquids and powders. Oral formulations include powders, granules, suspensions or solutions in water or non-aqueous media, capsules or tablets, for example. Thickeners, flavorings, diluents, emulsifiers, dispersing aids or binders may be used as needed.

Parenteral formulations may include sterile aqueous solutions which may also contain buffers, diluents and other suitable additives.

The dose regimen will depend on a number of factors which may readily be determined, such as severity and responsiveness of the condition to be treated, but will normally be one or more doses per day, with a course of treatment lasting from several days to several months, or until a cure is effected or a diminution of disease state is achieved. One of ordinary skill may readily determine optimum dosages, dosing methodologies and repetition rates. In general, it is contemplated that unit dosage form compositions according to the present invention will contain from about 0.01 mg to about 500 mg of active ingredient, preferably about 0.1 mg to about 10 mg of active ingredient. Topical formulations (such as creams, lotions, solutions, etc.) may have a concentration of active ingredient of from about 0.01% to about 50%, preferably from about 0.1% to about 10%.

The following examples are illustrative of the processes and products of the present invention, but are not to be construed as limiting.

EXAMPLE 1

General Procedure for Preparation of Bicyclic Trisanhydrides (BTAS) from $Zp_2$ This Example illustrates a general method of preparing BTAs from $P^1$-substituted phosphonomethylene-phosphonic acids ($Z$—$P^1$—$CH_2$—$P^2$—OH or $Zp_2$) wherein Z is previously defined.

The mixture of monosubstituted suitably protected methylenebis (phosphonate) ($Zp_2$, 1.0 mmol, bis(triethyl)-ammonium salt) and dicyclohexylcarbodiimide (DCC, 3–4 mmol) in anhydrous pyridine (10 ml) is kept for 6 hours at room temperature and the progress of the reaction is followed by $^{31}P$ NMR. The reaction was considered completed when signals of the starting methylenediphosphonate disappeared and the spectrum showed 3 characteristic groups of multisignal resonances at –0.5–2.0 ppm, at 6.0–8.0 ppm and at 12.8–17.6 ppm. These three sets of multisignal resonances are consistent with the structure of bicyclic trisanhydride (BTA). No further changes in the $^{31}P$ NMR spectrum are observed after addition of DCC and incubating the mixture at 60° C. for several hours. The product, BTA in solution, is too unstable to isolate in the pure state, but can be stored for several days at room temperature or several weeks in a refrigerator without change if protected from moisture.

In this manner, the following BTAs are prepared:

BTA from 2',3'-O-isopropylideneadenosin-5'-ylphosphonomethylenephosphonate.

BTA from 2',3'-O-isopropylideneinosin-5'-ylphosphonomethylenephosphonate.

BTA from 2',3'-O-isopropylideneguanosin-5'-ylphosphonomethylenephosphonate.

BTA from 2',3'-O-isopropylideneuridin-5'-ylphosphonomethylenephosphonate.

BTA from 2',3'-O-isopropylidenecytidine-5'-ylphosphonomethylenephosphonate.

BTA from 3'-O-(tetrahydropyranyl)thymidin-5'-ylphosphonomethylenephosphonate.

BTA from 2',3'-O-isopropylidenetiazofurin-5'-ylphosphonomethylenephosphonate.

BTA from 2',3'-O-isopropylidene- 3-ribofuranosylbenzamid-5'-ylphosphonomethylenephosphonate.

BTA from 2',3'-O-isopropylidene-ψ-uridin-5'-ylphosphonomethylenephosphonate.

BTA from 2',3'-O-isopropylidene-ψ-isocytidin-5'-ylphosphonomethylene-phosphonate.

BTA from 9-(2'-deoxy-2'-fluoro-3'-O-tetrahydro-pyranyl-β-D-arabinofuranosyl)adenine-5-ylphosphono-methylene-phosphonate.

BTA from 9-(3'-deoxy-3'-fluoro-2'-O-tetrahydropyranyl-β-D-xylofuranosyl)adenine-5-ylphosphonomethylenephosphonate.

BTA from 2'-deoxy-2'-fluoro-3'-O-tetrahydropyranyl-adenosin-5-ylphosphonomethylenephosphonate.

BTA from 3'-deoxy-3'-fluoro-2'-O-tetrahydropyranyl-adenosin-5-yl-phosphonomethylenephosphonate.

BTA from 2',3'-O-isopropylidene-9-deazaadenosin-5'-ylphosphonomethylene-phosphonate.

BTA from 2',3'-O-isopropylidene-9-deazainosin-5'-ylphosphonomethylenephosphonate.

BTA from 2',3'-O-isopropylidene-9-deazaguanosin-5'-ylphosphonomethylenephosphonate.

BTA from 2',3'-O-isopropylideneadenosin-5'-ylphosphonodifluoromethylenephosphonate.

BTA from 2',3'-O-isopropylideneinosin-5'-ylphosphonodifluoromethylenephosphonate.

BTA from 2',3'-O-isopropylideneguanosin-5'-ylphosphonodifluoromethylenephosphonate.

BTA from 3'-O-(tetrahydropyranyl)thymidin-5'-ylphosphonodifluoromethylenephosphonate.

BTA from 2',3'-O-isopropylidenetiazofurin-5'-ylphosphonodifluoromethylenephosphonate.

BTA from 2',3'-O-isopropylidene-3-ribosylbenzamid-5'-ylphosphonodifluoromethylenephosphonate.

BTA from 2',3'-O-isopropylidene-ψ-uridin-5'-ylphosphonodifluoromethylenephosphonate.

BTA from 2',3'-O-isopropylidene-y-isocytidin-5'-ylphosphonodifluoromethylenephosphonate.

BTA from 9-(2'-deoxy-2'-fluoro-3'-O-tetrahydropyranyl-β-D-arabinofuranosyl)adenine-5-ylphosphonodifluoromethylenephosphonate.

BTA from 9-(3'-deoxy-3'-fluoro-2'-O-tetrahydropyranyl-β-D-xylofuranosyl)adenine-5-ylphosphonodifluoromethylenephosphonate.

BTA from 2'-deoxy-2'-fluoro-3'-O-tetrahydropyranyl-adenosin-5-ylphosphonodifluoromethylenephosphonate.

BTA from 3'-deoxy-3'-fluoro-2'-O-tetrahydropyranyl-adenosin-5-ylphosphonodifluoromethylenephosphonate.

BTA from 2',3'-O-isopropylidene-9-deazaadenosin-5'-ylphosphonodifluoromethylenephosphonate.

BTA from 2',3'-O-isopropylidene-9-deazainosin-5'-ylphosphonodifluoromethylenephosphonate.

BTA from 2',3'-O-isopropylidene-9-deazaguanosin-5'-ylphosphonodifluoromethylenephosphonate.

EXAMPLE 2

General Procedure for Preparation of Bicyclic Trisanhydrides from $Zp_4Z_1$

This Example illustrates another general method for the synthesis of BTAs from P1,P4-disubstituted phosphonomethylene(phosphonic)P2,P3-anhydride ($Zp^1$—$CH_2$—$P^2$—O—$P^3$—$CH_2$—$P^4$—$Z^1$ or $Zp^4Z_1$) wherein Z and $Z_1$ may be the same or different and are defined previously.

A mixture of the methylenediphosphonic anhydride [$Zp_4Z$, 1.0 mmol, bis(triethylammonium salt)] and dicyclohexyl-carbodiimide (DCC, 3.0 mmol) in anhydrous pyridine (10 ml) is kept for 4 hours at room temperature and the reaction is monitored by $^{31}P$ NMR. The reaction is completed when signals of the starting methylenediphosphonate anhydride ($Zp_4Z$) disappears and the spectrum shows 3 characteristic groups of multisignal resonances at –0.5–2.0 ppm, at 6.0–8.0 ppm, and at 12.8–17.6 ppm.

In this manner, the following BTAs are prepared:

BTA from $P^1,P^4$-di(adenosin-5'-yl) phosophonomethylenephosphonic $P^2,P^3$-anhydride.

BTA from $P^1,P^4$-di[9-(2'-deoxy-2'-fluoro-β-D-arabonofuranosyl)adenine-5-yl] phosphonomethylenephosphonic $P^2,P^3$-anhydride.

BTA from $P^1,P^4$-di[9-(3'-deoxy-3'-fluoro-β-D-xylofuranosyl)adenine-5'-yl] phosphonomethylenephosphonic $P^2,P^3$-anhydride.

BTA from $P^1,P^4$-di(2'-deoxy-2'-fluoroadenosin-5-yl) phosphonomethylenephosphonic $P^2,P^3$-anhydride.
BTA from $P^1,P^4$-di(3'-deoxy-3'-fluoroadenosin-5-yl) phosphonomethylenephosphonic $P^2,P^3$-anhydride.
BTA from $P^1,P^4$-di(inosin-5'-yl) phosophonomethylenephosphonic $P^2,P^3$-anhydride.
BTA from $P^1,P^4$-di(guanosin-5'-yl) phosophonomethylenephosphonic $P^2,P^3$-anhydride.
BTA from $P^1,P^4$-di(uridin-5'-yl) phosophonomethylenephosphonic $P^2,P^3$-anhydride.
BTA from $P^1,P^4$-di($N^4$-acetylcytidin-5'-yl) phosphonomethylenephosphonic $P^2,P^3$-anhydride.
BTA from $P^1,P^4$-di(thymidin-5'-yl) phosphonomethylenephosphonic $P^2,P^3$-anhydride.
BTA from $P^1,P^4$-di(tiazifurin-5'-yl) phosphonomethylenephosphonic $P^2,P^3$-anhydride.
BTA from $P^1,P^4$-di(3-ribosylbenzamid-5'-yl) phosphonomethylenephosphonic $P^2,P^3$-anhydride.
BTA from $P^1,P^4$-di($\psi$-uridin-5'-yl) phosphonomethylenephosphonic $P^2,P^3$-anhydride.
BTA from $P^1,P^4$-di($\psi$-isocytidin-5'-yl) phosphonomethylenephosphonic $P^2,P^3$-anhydride.
BTA from $P^1,P^4$-di(9-deazaadenosin-5'-yl) phosphonomethylenephosphonic $P^2,P^3$-anhydride.
BTA from $P^1,P^4$-di(9-deazainosin-5'-yl) phosphonomethylenephosphonic $P^2,P^3$-anhydride.
BTA from $P^1,P^4$-di(9-deazaguanosin-5'-yl) phosphonomethylenephosphonic $P^2,P^3$-anhydride.
BTA from $P^1,P^4$-di(adenosin-5'-yl) phosphonodifluoromethylenephosphonic $P^2,P^3$-anhydride.
BTA from $P^1,P^4$-di(inosin-5'-yl) phosphonodifluoromethylenephosphonic $P^2,P^3$-anhydride.
BTA from $P^1,P^4$-di(guanosin-5'-yl) phosphonodifluoromethylenephosphonic $P^2,P^3$-anhydride.
BTA from $P^1,P^4$-di(thymidin-5'-yl) phosphonodifluoromethylenephosphonic $P^2,P^3$-anhydride.
BTA from $P^1,P^4$-di(tiazofurin-5'-yl) phosphonodifluoromethylenephosphonic $P^2,P^3$-anhydride.
BTA from $P^1,P^4$-di(3-ribosylbenzamid-5'-yl) phosphonodifluoromethylenephosphonic $P^2,P^3$-anhydride.
BTA from $P^1,P^4$-di($\psi$-uridin-5'-yl) phosphonodifluoromethylenephosphonic $P^2,P^3$-anhydride.
BTA from $P^1,P^4$-di($\psi$-isocytidin-5'-yl) phosphonodifluoromethylenephosphonic $P^2,P^3$-anhydride.
BTA from $P^1,P^4$-di(9-deazaadenosin-5'-yl) phosphonodifluoromethylenephosphonic $P^2,P^3$-anhydride.
BTA from $P^1,P^4$-di(9-deazainosin-5'-yl) phosphonodifluoromethylenephosphonic $P^2,P^3$-anhydride.
BTA from $P^1,P^4$-di(9-deazaguanosin-5'-yl) phosphonodifluoromethylenephosphonic $P^2,P^3$-anhydride.

EXAMPLE 3

Synthesis of $P^1$-(2',3'-O-Isopropylideneadenosin-5'-yl)-$P^2$-(2',3'-O-isopropylidene-$\beta$-D-ribofuranosylbenzen-3-carboxamide-5'-yl) methylenebis(phosphonate), an Analogue of Protected Nicotinamide Adenine Dinucleotide This Example illustrates the synthesis of an important analogue by using a BTA which is reacted with a nucleoside.

(2',3'-O-Isopropylidene-$\beta$-D-ribofuranosylbenzene-carboxamide-5'-yl)phosphonomethylenephosphonic acid (565 mg, 1.0 mmol) as bistriethylammonium salt is dissolved in pyridine (15 ml) containing DCC (720 mg, 3.5 mmol), and the mixture is stirred at room temperature for 20 hours. $^{31}$P NMR analysis shows disappearance of resonance signals ($\delta$ 15.46, singlet in pyridine) with concomitant formation of BTA with characteristic multisignal resonances. At this time 2',3'-O-isopropylideneadenosine (552 mg, 1.15 mmol) is added and the reaction mixture is kept at 65° C. until the $^{31}$P spectrum of the reaction indicates the formation of intermediate (broad signals centered at 8 and 18 ppm). Water is added and the mixture is stirred at room temperature for 3 hours. After concentration in vacuo, the residue is chromatographed on an HPLC column to give $P^1$-(2,3-O-isopropylidene-$\beta$-D-ribofuranosylbenzene-3-carboxamide-5'-yl)-$P^2$-(2',3'-O-isopropylideneadenosin-5'-yl)methylenebis(phosphonate) as the bistriethylammonium salt (850 mg, 97.7%). $^1$H NMR (D$_2$O) $\delta$ 1.27–1.31 (t, 18H, Et$_3$N), 1.40 (s, 3H, iPr), 1.46 (s, 3H, iPr), 1.64 (s, 3H, iPr), 1.68 (s, 3H, iPr), 2.05–2.20 (m, 2H, P—CH$_2$—P), 3.21 (q, 12H, Et$_3$N), 4.09–4.12 [m, 4H, H5',H5" (B) and (A)], 4.26–4.28 [m, 1H, H4'(B)], 4.59–4.64 [m, 2H, H4'(A), H2'(B)], 4.80 [1H, H1'(B)], 4.88 [dd, 1H, H3'(B), $J_{1',2'}$= 5.7 Hz, $J_{2',3'}$=6.5 Hz), 5.20 [m, 1H, H3' (A)], 5.30 [dd, 1H, H2' (A), $J_{1',2'}$=3.0 Hz, $J_{2',3'}$=6.5 Hz], 6.12 [d, 1H, H1' (A)], 7.39 [pseudo t, 1H, H5(B)], 7.46 d, 1H, H4(B), $J_{4,5}$=7.8 Hz], 7.64 [d, 1H, H6(B), $J_{5,6}$=7.8 Hz], 7.67 (s, 1H, H2(B)], 8.15, 8.40 [two 1H singlets, H2(A), H8(A)].

The following $P^1,P^2$-disubstituted methylenebis (phosphonate) analogues are synthesized by following the same procedure but using the corresponding BTA and nucleophiles:

$P^1$-(2',3'-O-Isopropylideneadenosin-5'-yl)-$P^2$-(2',3'-O-isopropylideneadenosin-5'-yl)methylenebis (phosphonate).

$P^1$-(2',3'-O-Isopropylideneadenosin-5'-yl)-$P^2$-(2',3'-O-isopropylideneguanosin-5'-yl)methylenebis (phosphonate).

$P^1$-(2',3'-O-Isopropylideneadenosin-5'-yl)-$P^2$-(2',3'-O-isopropylideneuridin-5'-yl)methylenebis (phosphonate).

$P^1$-(2',3'-O-Isopropylideneadenosin-5'-yl)-$P^2$-(2',3'-O-isopropylidene-$N^4$-acetylcytidin-5'-yl)methylenebis (phosphonate).

$P^1$-(2',3'-O-Isopropylideneadenosin-5'-yl)-$P^2$-(2',3'-O-isopropylideneinosin-5'-yl)methylenebis (phosphonate).

$P^1$-(2',3'-O-Isopropylideneadenosin-5'-yl)-$P^2$-(2',3'-O-isopropylidenetiazofurin-5'-yl)methylenebis (phosphonate).

$P^1$-(2',3'-O-Isopropylideneadenosin-5'-yl)-$P^2$-(2',3'-O-isopropylidene-$\beta$-D-ribofuranosylbenzene-3-carboxamide-5'-yl)methylenebis(phosphonate).

$P^1$-(2',3'-O-Isopropylideneadenosin-5'-yl)-$P^2$-(2', 3'-O-isopropylidene-$\psi$-uridin-5'-yl)methylenebis (phosphonate).

$P^1$-(2',3'-O-Isopropylideneadenosin-5'-yl)-$P^2$-[5-(2',3'-O-isopropylidene-$\beta$-D-ribofuranosyl)nicotinamide-5'-yl]-methylenebis(phosphonate).

$P^1$-(2',3'-O-Isopropylideneadenosin-5'-yl)-$P^2$-[6-(2',3'-O-isopropylidene-$\beta$-D-ribofuranosyl)picolinamide-5'-yl] methylenebis(phosphonate).

$P^1$-(2',3'-O-Isopropylideneguanosin-5'-yl)-$P^2$-(2',3'-O-isopropylideneguanosin-5'-yl)methylenebis (phosphonate).

P¹-(2',3'-O-Isopropylideneguanosin-5'-yl)-P²-(2',3'-O-isopropylideneuridin-5'-yl)methylenebis(phosphonate).

P¹-(2',3'-O-Isopropylideneguanosin-5'-yl)-P²-(2',3'-O-isopropylidene-N⁴-acetylcytidin-5'-yl)methylenebis(phosphonate).

P¹-(2',3'-O-Isopropylideneguanosin-5'-yl)-P²-(2',3'-O-isopropylideneinosin-5'-yl)methylenebis(phosphonate).

P¹-(2',3'-O-Isopropylideneguanosin-5'-yl)-P²-(2',3'-O-isopropylidenetiazofurin-5'-yl)methylenebis(phosphonate).

P¹-(2',3'-O-Isopropylideneguanosin-5'-yl)-P²-(2',3'-O-isopropylidene-β-D-ribofuranosylbenzene-3-carboxamide-5'-yl)methylenebis(phosphonate).

P¹-(2',3'-O-Isopropylideneguanosin-5'-yl)-P²-(2',3'-O-isopropylidene-ψ-uridin-5'-yl)methylenebis(phosphonate).

P¹-(2',3'-O-Isopropylideneguanosin-5'-yl)-P²-[5'-(2',3'-isopropylidene-β-D-ribofuranosyl)nicotinamide-5'-yl]-methylenebis(phosphonate).

P¹-(2',3'-O-Isopropylideneguanosin-5'-yl)-P²-[6-(2',3'-O-isopropylidene-β-D-ribofuranosyl)picolinamide-5'-yl]-methylenebis(phosphonate).

P¹-(2',3'-O-Isopropylideneinosin-5'-yl)-P²-(2',3'-O-isopropylideneuridin-5'-yl)methylenebis(phosphonate).

P¹-(2',3'-O-Isopropylideneinosin-5'-yl)-P²-(2',3'-O-isopropylidene-N⁴-acetylcytidin-5'-yl)methylenebis(phosphonate).

P¹-(2',3'-O-Isopropylideneinosin-5'-yl)-P²-(2',3'-O-isopropylideneinosin-5'-yl)methylenebis(phosphonate).

P¹-(2',3'-O-Isopropylideneinosin-5'-yl)-P²-(2',3'-O-isopropylidenetiazofurin-5'-yl)methylenebis(phosphonate).

P¹-(2',3'-O-Isopropylideneinosin-5'-yl)-P²-(2',3'-O-isopropylidene-β-D-ribofuranosylbenzene-3-carboxamide- 5'-yl)methylenebis(phosphonate).

P¹-(2',3'-O-Isopropylideneuridin-5'-yl)-P²-(2',3'-O-isopropylideneguanosin-5'-yl)methylenebis(phosphonate).

P¹-(2',3'-O-Isopropylideneuridin-5'-yl)-P²-(2',3'-O-isopropylidene-N⁴-acetylcytidin-5'-yl)methylenebis(phosphonate).

P¹-(2',3'-O-Isopropylideneuridin-5'-yl)-P²-(2',3'-O-isopropylideneuridin-5'-yl)methylenebis(phosphonate).

P¹-(2',3'-O-Isopropylideneuridin-5'-yl)-P²-(2',3'-O-isopropylidenetiazofurin-5'-yl)methylenebis(phosphonate).

P¹-(2',3'-O-Isopropylidene-N⁴-acetylcytidin-5'-yl)-P²-(2', 3'-O-isopropylidene-N⁴-aetylcytidin-5'-yl)methylenebis(phosphonate).

P¹-(2',3'-O-Isopropylidene-N⁴-acetylcytidin-5'-yl)-P²-(2', 3'-O-isopropylidenetiazofurin-5'-yl)methylenebis(phosphonate).

P¹-(2',3'-O-Isopropylidene-N⁴-acetylcytidin-5'-yl)-P²-(2', 3'-O-isopropylidene-β-D-ribofuranosylbenzene-3-carboxamide-5'-yl)methylenebis(phosphonate).

P¹-(2',3'-O-Isopropylidene-tiazofurin-5'-yl)-P²-(2'-O-acety-3'-deoxy-3'-fluoroadenosin-5'-yl)methylenebis(phosphonate).

P¹-(2',3'-O-Isopropylidene-tiazofurin-5'-yl)-P²-(3'-O-acety-2'-deoxy-2'-fluoroadenosin-5'-yl)methylenebis(phosphonate).

P¹-(2',3'-O-Isopropylidene-tiazofurin-5'-yl)-P²-[9-(3'-O-acetyl-2'-deoxy-2'-fluoro-β-D-arabinofuranosyl)adenin-5'-yl]methylenebis(phosphonate).

P¹-(2',3'-O-Isopropylidene-tiazofurin-5'-yl)-P²-[9-(2'-O-acetyl-3'-deoxy-3'-fluoro-β-D-xylofuranosyl)adenin-5'-yl]methylenebis(phosphonate).

P¹-(2',3'-O-Isopropylidene-β-D-ribofuranosylbenzene-3-carboxamide-5'-yl)-P²-[9-(3'-O-acetyl-2'-deoxy-2'-fluoroadenosin-5'-yl]methylenebis(phosphonate).

P¹-(2',3'-O-Isopropylidene-β-D-ribofuranosylbenzene-3-carboxamide-5'-yl)-P²-[9-(2'-O-acetyl-3'-deoxy-3'-fluoroadenosin-5'-yl]methylenebis(phosphonate).

P¹-(2',3'-O-Isopropylidene-β-D-ribofuranosylbenzene-3-carboxamide-5'-yl)-P²-[9-(2'-acetyl-3'-deoxy-3'-fluoro-β-D-arabinofuranosyl)adenin-5'-yl]methylenebis(phosphonate).

P¹-(2',3'-O-Isopropylidene-β-D-ribofuranosylbenzene-3-carboxamide-5'-yl)-P²-[9-(2'-O-acetyl-3'-deoxy-3'-fluoro-β-D-xylofuranosyl)adenin-5'-yl]methylenebis(phosphonate).

EXAMPLE 4

Synthesis of P¹-(adenosin-5'-yl)-P²-(β-D-ribofuranosylbenzen-3-carboxamide-5'-yl)methylenebis(phosphonate), an Analogue of Nicotinamide Adenine Dinucleotide P¹-(2',3'-O-Isopropylideneadenosin-5'-yl)-P²-(2',3'-O-isopropylidene-β-D-ribofuranosylbenzen-3-carboxamide-5'-yl)methylenebis(phosphonic acid) bistriethylammonium salt (850 mg) is treated with Dowex 50WX8/H⁺ in water and purified by passing through the column of Dowex 50WX8/H⁺ to give the desired product as the free acid (790 mg, 96%).

¹H NMR (D₂O) δ 2.27–2.27 (pseudo t, 2H, P—CH₂—P), 4.05 [dd, 1H, H2' (B), $J_{1',2'}$=7.0 Hz, $J_{2',3'}$=5.1 Hz], 4.17–4.20 [m, 4H, H5',5" (A) and (B)], 4.25–4.27 [m, 2H, H3' (B), H4' (B)], 4.37 [pseudo t, 1H, H3' (A)], 4.66 [pseudo t, H2' (A)], 4.80 [d, 1H, H1' (B)], 6.06 [d, 1H, H1' (A), $J_{1',2'}$=4.9 Hz], 7.41 [pseudo t, 1H, H5(B)], 7.56 d, 1H, H4(B), $J_{4,5}$=7.8 Hz], 7.63 [d, 1H, H6(B), $J_{5,6}$=7.8 Hz], 7.69 (s, 1H, H2(B)], 8.32, 8.57 [two 1H singlets, H2(A), H8(A)], ³¹P NMR (D₂O) δ 20.86 and 21.13 (AB system $J_{AB}$=10.3 Hz). MS (ES) m/z 659 (M–H)⁺.

The following P¹,P²-disubstituted methylenebis(phosphonate) analogues as free acids are synthesized by following the same procedure but using the corresponding BTA and nucleophiles:

P¹-(Adenosin-5'-yl)-P²-(adenosin-5'-yl)methylenebis(phosphonate).

P¹-(Adenosin-5'-yl)-P²-(guanosin-5'-yl)methylenebis(phosphonate).

P¹-(Adenosin-5'-yl)-P²-(uridin-5'-yl)methylenebis(phosphonate).

P¹-(Adenosin-5'-yl)-P²-(cytidin-5'-yl)methylenebis(phosphonate).

P¹-(Adenosin-5'-yl)-P²-(inosin-5'-yl)methylenebis(phosphonate).

P¹-(Adenosin-5'-yl)-P²-(tiazofurin-5'-yl)methylenebis(phosphonate).

P¹-(Adenosin-5'-yl)-P²-(β-D-ribofuranosyl-benzene-3-carboxamide-5'-yl)methylenebis(phosphonate).

P$^1$-(Adenosin-5'-yl)-P$^2$-(ψ-uridin-5'-yl)methylenebis(phosphonate).

P$^1$-(Adenosin-5'-yl)-P$^2$-[5-(β-D-ribofuranosyl)-nicotinamide-5'-yl]methylenebis(phosphonate).

P$^1$-(Adenosin-5'-yl)-P$^2$-[6-(β-D-ribofuranosyl)-picolinamide-5'-yl]methylenebis(phosphonate).

P$^1$-(Guanosin-5'-yl)-P$^2$-(guanosin-5'-yl)methylenebis(phosphonate).

P$^1$-(Guanosin-5'-yl)-P$^2$-(uridin-5'-yl)methylenebis(phosphonate).

P$^1$-(Guanosin-5'-yl)-P$^2$-(cytidin-5'-yl)methylenebis(phosphonate).

P$^1$-(Guanosin-5'-yl)-P$^2$-(inosin-5'-yl)methylenebis(phosphonate).

P$^1$-(Guanosin-5'-yl)-P$^2$-(tiazofurin-5'-yl)methylenebis(phosphonate).

P$^1$-(Guanosin-5'-yl)-P$^2$-(β-D-ribofuranosyl-benzene-3-carboxamide-5'-yl)methylenebis(phosphonate).

P$^1$-(Guanosin-5'-yl)-P$^2$-(ψ-uridin-5'-yl)methylenebis(phosphonate).

P$^1$-(Guanosin-5'-yl)-P$^2$-[5-(β-D-ribofuranosyl)nicotinamide-5'-yl]methylenebis(phosphonate).

P$^1$-(Guanosin-5'-yl)-P$^2$-[6-(β-D-ribofuranosyl)picolinamide-5'-yl]methylenebis(phosphonate).

P$^1$-(Inosin-5'-yl)-P$^2$-(uridin-5'-yl)methylenebis(phosphonate).

P$^1$-(Inosin-5'-yl)-P$^2$-(cytidin-5'-yl)methylenebis(phosphonate).

P$^1$-(Inosin-5'-yl)-P$^2$-(inosin-5'-yl)methylenebis(phosphonate).

P$^1$-(Inosin-5'-yl)-P$^2$-(tiazofurin-5'-yl)methylenebis(phosphonate).

P$^1$-(Inosin-5'-yl)-P$^2$-(β-D-ribofuranosylbenzene-3-carboxamide-5'-yl)methylenebis(phosphonate).

P$^1$-(Uridin-5'-yl)-P$^2$-(guanosin-5'-yl)methylenebis(phosphonate).

P$^1$-(Uridin-5'-yl)-P$^2$-(cytidin-5'-yl)methylenebis(phosphonate).

P$^1$-(Uridin-5'-yl)-P$^2$-(uridin-5'-yl)methylenebis(phosphonate).

P$^1$-(Uridin-5'-yl)-P$^2$-(tiazofurin-5'-yl)methylenebis(phosphonate).

P$^1$-(Cytidin-5'-yl)-P$^2$-(cytidin-5'-yl)methylenebis(phosphonate).

P$^1$-(Cytidin-5'-yl)-P$^2$-(tiazofurin- 5'-yl)methylenebis(phosphonate).

P$^1$-(Cytidin-5'-yl)-P$^2$-(β-D-ribofuranosylbenzene-3-carboxamide-5'-yl)methylenebis(phosphonate).

P$^1$-(Tiazofurin-5-yl)-P$^2$-(3'-deoxy-3'-fluoroadenosin-5'-yl)methylenebis(phosphonate).

P$^1$-(Tiazofurin-5-yl)-P$^2$-(2'-deoxy-2'-fluoroadenosin-5'-yl)methylenebis(phosphonate).

P$^1$-(Tiazofurin-5-yl)-P$^2$-[9-(2'-deoxy-2'-fluoro-β-D-arabinofuranosyl)adenin-5'-yl]methylenebis(phosphonate).

P$^1$-(Tiazofurin-5-yl)-P$^2$-[9-(3'-deoxy-3'-fluoro-β-D-xylofuranosyl)adenin-5'-yl]methylenebis(phosphonate).

P$^1$-(β-D-Ribofuranosylbenzene-3-carboxamide-5'-yl)-P$^2$-[9-(2'-deoxy-2'-fluoroadenosin-5'-yl]methylenebis(phosphonate).

P$^1$-(β-D-Ribofuranosylbenzene-3-carboxamide-5'-yl)-P$^2$-[9-(3'-deoxy-3'-fluoroadenosin-5'-yl]methylenebis(phosphonate).

P$^1$-(β-D-Ribofuranosylbenzene-3-carboxamide-5'-yl)-P$^2$-[9-(3'-deoxy-3'-fluoro-β-D-arabinofuranosyl)adenin-5'-yl]-methylenebis(phosphonate).

P$^1$-(β-D-Ribofuranosylbenzene-3-carboxamide-5'-yl)-P$^2$-[9-(3'-deoxy-3'-fluoro-β-D-xylofuranosyl)adenin-5'-yl]methylenebis(phosphonate).

EXAMPLE 5

Preparation of P$^1$-(2',3'-O-isopropylidenetiazofurin-5'-yl)-P$^2$-(2',3'-O-isopropylideneadenosin-5'-yl) difluoromethylenebis(phosphonate)

This Example illustrates that BTAs derived from nucleoside 5'-phosphonyldifluoromethylenephosphonates can serve as a synthon for the synthesis of analogues of P$^1$,P$_2$-dinucleoside diphosphate analogues.

The bicyclic trisanhydride prepared from 2',3'-O-isopropylidene-tiazofurin-5'-yl-difluoromethylenebisphosphonate (1 mmol in 10 ml of pyridine) is treated with 2',3'-O-isopropylideneadenosine (1.2 mmol) and the mixture is kept at 55° C. for 7 hours. HPLC purification affords pure product (retention time 45 minutes, yield 35.5%) $^{31}$P NMR (D$_2$O), δ 4.25 dt, J$_{P,P}$=11.0 Hz, J$_{P,F}$=83.0 Hz), $^{19}$F NMR (D$_2$O), δ 117.5 (t, J$_{P,F}$=83.1 Hz), $^1$H NMR (D$_2$O), δ 1.21 (t, 18H, Et$_3$N), 1.32, 1.41, 1.56, 1.64 [four 3H singlets, iPr (A), iPr(T)], 3.09 (q, 12H, Et$_3$N), 4.00–4.10 and 4.16–4.24 [two 2H multiplets, H5',5" (A), H5',5" (T)], 4.32–4.38 and 4.55–4.60 [two 1H muliplets, H4' (A), H4' (T)], 4.86–4.93 [m, 2H, H2',H3' (T)], 5.12 [d, 1H, H1' (T), J$_{1',2'}$=3.3 Hz], 5.18 [dd, 1H, H3' (A), J$_{2',3'}$=6.1 Hz, J$_{3',4'}$=1.8 Hz], 5.30 [dd, 1H, H2' (A), J$_{1',2'}$=2.5 Hz], 6.17 [d, 1H, H1' (A)], 8.05, 8.13, 8.37 (three 1H singlets, H2, H8, H5).

The following P$^1$,P$^2$-disubstituted difluoromethylenebis(phosphonate) analogues are synthesized by following the same procedure but using the corresponding BTA and nucleophiles:

P$^1$-(2',3'-O-Isopropylideneadenosin-5'-yl)-P$^2$-(2',3'-O-isopropylideneadenosin-5'-yl)difluoromethylenebis(phosphonate).

P$^1$-(2',3'-O-Isopropylideneadenosin-5'-yl)-P$^2$-(2',3'-O-isopropylideneguanosin-5'-yl)difluoromethylenebis(phosphonate).

P$^1$-(2',3'-O-Isopropylideneadenosin-5'-yl)-P$^2$-(2',3'-O-isopropylideneuridin-5'-yl)difluoromethylenebis(phosphonate).

P$^1$-(2',3'-O-Isopropylideneadenosin-5'-yl)-P$^2$-(2',3'-O-isopropylidene-N$^4$-acetylcytidin-5'-yl)difluoromethylenebis(phosphonate).

P$^1$-(2',3'-O-Isopropylideneadenosin-5'-yl)-P$^2$-(2',3'-O-isopropylideneinosin-5'-yl)difluoromethylenebis(phosphonate).

P$^1$-(2',3'-O-Isopropylideneadenosin-5'-yl)-P$^2$-(2',3'-O-isopropylidenetiazofurin-5'-yl)difluoromethylenebis(phosphonate).

P$^1$-(2',3'-O-Isopropylideneadenosin-5'-yl)-P$^2$-(2',3'-O-isopropylidene-β-D-ribofuranosylbenzene-3-carboxamide-5'-yl)-difluoromethylenebis(phosphonate).

P$^1$-(2',3'-O-Isopropylideneadenosin-5'-yl)-P$^2$-(2',3'-O-isopropylidene-ψ-uridin-5'-yl)difluoromethylenebis(phosphonate).

P$^1$-(2',3'-O-Isopropylideneadenosin-5'-yl)-P$^2$-[5-(2',3'-O-isopropylidene-β-D-ribofuranosyl)nicotinamide-5'-yl]difluoromethylenebis(phosphonate).

P$^1$-(2',3'-O-Isopropylideneadenosin-5'-yl)-P$^2$-[6-(2',3'-O-isopropylidene-β-D-ribofuranosyl)picolinamide-5'-yl]difluoromethylenebis(phosphonate).

P$^1$-(2',3'-O-Isopropylideneguanosin-5'-yl)-P$^2$-(2',3'-O-isopropylideneguanosin-5'-yl)difluoromethylenebis(phosphonate).

P$^1$-(2',3'-O-Isopropylideneguanosin-5'-yl)-P$^2$-(2',3'-O-isopropylideneuridin-5'-yl)difluoromethylenebis(phosphonate).

P$^1$-(2',3'-O-Isopropylideneguanosin-5'-yl)-P$^2$-(2',3'-O-isopropylidene-N$^4$-acetylcytidin-5'-yl)difluoromethylenebis(phosphonate).

P$^1$-(2',3'-O-Isopropylideneguanosin-5'-yl)-P$^2$-(2',3'-O-isopropylideneinosin-5'-yl)difluoromethylenebis(phosphonate).

P$^1$-(2',3'-O-Isopropylideneguanosin-5'-yl)-P$^2$-(2',3'-O-isopropylidenetiazofurin-5'-yl)difluoromethylenebis(phosphonate).

P$^1$-(2',3'-O-Isopropylideneguanosin-5'-yl)-P$^2$-( 2',3'-O-isopropylidene-β-D-ribofuranosyl-benzene-3-carboxamide-5'-yl)difluoromethylenebis(phosphonate).

P$^1$-(2',3'-O-Isopropylideneguanosin-5'-yl)-P$^2$-(2',3'-O-isopropylidene-ψ-uridin-5'-yl)difluoromethylenebis(phosphonate).

P$^1$-(2',3'-O-Isopropylideneguanosin-5'-yl)-P$^2$-[5-(2',3'-O-isopropylidene-β-D-ribofuranosyl)nicotinamide-5'-yl]-difluoromethylenebis(phosphonate).

P$^1$-(2',3'-O-Isopropylideneguanosin-5'-yl)-P$^2$-[6-(2',3'-O-isopropylidene-β-D-ribofuranosyl)picolinamide-5'-yl]-difluoromethylenebis(phosphonate).

P$^1$-(2',3'-O-Isopropylideneinosin-5'-yl)-P$^2$-(2',3'-O-isopropylideneuridin-5'-yl)difluoromethylenebis(phosphonate).

P$^1$-(2',3-O-Isopropylideneinosin-5'-yl)-P$^2$-(2',3'-O-isopropylidene-N$^4$-acetylcytidin-5'-yl)difluoromethylenebis(phosphonate).

P$^1$-(2',3'-O-Isopropylideneinosin-5'-yl)-P$^2$-(2',3'-O-isopropylideneinosin-5'-yl)difluoromethylenebis(phosphonate).

P$^1$-(2',3'-O-Isopropylideneinosin-5'-yl)-P$^2$-(2',3'-O-isopropylidenetiazofurin-5'-yl)difluoromethylenebis(phosphonate).

P$^1$-(2',3'-O-Isopropylideneinosin-5'-yl)-P$^2$-(2',3'-O-isopropylidene-β-D-ribofuranosyl-benzene-3-carboxamide-5'-yl)-difluoromethylenebis(phosphonate).

P$^1$-(2',3'-O-Isopropylideneuridin-5'-yl)-P$^2$-(2',3'-O-isopropylideneguanosin-5'-yl)difluoromethylenebis(phosphonate).

P$^1$-(2',3'-O-Isopropylideneuridin-5'-yl)-P$^2$-(2',3'-O-isopropylidene-N$^4$-acetylcytidin-5'-yl)difluoromethylenebis(phosphonate).

P$^1$-(2',3'-O-Isopropylideneuridin-5'-yl)-P$^2$-( 2',3'-O-isopropylideneuridin-5'-yl)difluoromethylenebis(phosphonate).

P$^1$-(2',3'-O-Isopropylideneuridin-5'-yl)-P$^2$-(2',3'-O-isopropylidenetiazofurin-5'-yl)difluoromethylenebis(phosphonate).

P$^1$-(2',3'-O-Isopropylidene-N$^4$-acetylcytidin-5'-yl)-P$^2$-(2',3'-O-isopropylidene-N$^4$-aetylcytidin-5'-yl)difluoromethylenebis(phosphonate).

P$^1$-(2',3'-O-Isopropylidene-N$^4$-acetylcytidin-5'-yl)-P$^2$-(2',3'-O-isopropylidenetiazofurin-5'-yl)difluoromethylenebis(phosphonate).

P$^1$-(2',3'-O-Isopropylidene-N$^4$-acetylcytidin-5'-yl)-P$^2$-(2',3'-O-isopropylidene-β-D-ribofuranosyl-benzene-3-carboxamide-5'-yl)difluoromethylenebis(phosphonate).

P$^1$-(2',3'-O-Isopropylidene-tiazofurin-5'-yl)-P$^2$-(2'-O-acety-3'-deoxy-3'-fluoroadenosin-5'-yl)difluoromethylenebis(phosphonate).

P$^1$-(2',3'-O-Isopropylidene-tiazofurin-5'-yl)-P$^2$-(3'-O-acety-2'-deoxy-2'-fluoroadenosin-5'-yl)difluoromethylenebis(phosphonate).

P$^1$-(2',3'-O-Isopropylidene-tiazofurin-5-yl)-P$^2$-[9-(3'-O-acetyl-2'-deoxy-2'-fluoro-β-D-carabinofuranosyl)-adenin-5'-yl]-difluoromethylenebis(phosphonate).

P$^1$-(2',3'-O-Isopropylidene-tiazofurin-5'-yl)-P$^2$-[9-(2'-O-acetyl-3'-deoxy-3'-fluoro-β-D-xylofuranosyl)adenin-5'-yl]difluoromethylenebis(phosphonate).

P$^1$-(2',3'-O-Isopropylidene-β-D-ribofuranosyl-benzene-3-carboxamide-5'-yl)-P$^2$-[9-(3'-O-acetyl-2'-deoxy-2'-fluoroadenosin-5'-yl]difluoromethylenebis(phosphonate).

P$^1$-(2',3'-O-Isopropylidene-β-D-ribofuranosyl-benzene-3-carboxamide-5'-yl)-P$^2$-[9-(2'-O-acetyl-3'-deoxy-3'-fluoroadenosin-5'-yl]difluoromethylenebis(phosphonate).

P$^1$-(2',3'-O-Isopropylidene-β-D-ribofuranosyl-benzene-3-carboxamide-5'-yl)-P$^2$-9-(2'-O-acetyl-3'-deoxy-3'-fluoro-β-D-arabinofuranosyl)adenin-5'-yl]difluoromethylenebis(phosphonate).

P$^1$-(2',3'-O-Isopropylidene-β-D-ribofuranosyl-benzene-3-carboxamide-5'-yl)-P$^2$-[9-(2'-O-acetyl-3'-deoxy-3'-fluoro-β-D-xylofuranosyl)adenin-5'-yl]difluoromethylenebis(phosphonate).

EXAMPLE 6

Preparation of P$^1$-(tiazofurin-5'-yl)-P$^2$-(adenosin-5'-yl)difluoromethylenebis(phosphonate).

A treatment of P$^1$-(2',3'-O-isopropylidenetiazofurin-5-yl)-P$^2$-(2',3'-O-isopropylideneadenosin-5-yl)difluoromethylenebis(phosphonic acid) bistriethylamine salt with Dowex 50WX8/H$^+$ affords the deprotected product as the free acid in almost quantitative yield. $^{31}$P NMR (D$_2$O) 4.02, 4.36 (AB part of ABX$_2$ system, J$_{AB}$=55.3, J$_{AX}$=83.1, J$_{BX}$=83.5 Hz, X=F), $^1$H NMR (D$_2$O) δ 4.22–4.44 [8H, m, adenosine (A) and tiazofurin (T) H-3', H4', H5', H5")], 4.51 [1H, dd, H2' (T), J$_{1',2'}$=4.9, J$_{2',3'}$=4.0 Hz], 4.67 [1H, dd, H2' (A), J$_{1',2'}$=5.5, J$_{2',3'}$=5.2 Hz], 5.10 [1H, d, H1' (T), J$_{1',2'}$=4.9 Hz], 6.10 [1H, d, H1' (A), J$_{1',2'}$=5.5 Hz], 8.00 (1H, s, H5), 8.20 and 8.48 (two 1H singlets, H2, H8).

The following P$^1$,P$^2$-disubstituted difluoromethylenebis(phosphonate) analogues as the free acids are synthesized by following the same procedure but using the corresponding BTA and nucleophiles:

P$^1$-(Adenosin-5'-yl)-P$^2$-(adenosin-5'-yl)difluoromethylenebis(phosphonate).

P$^1$-(Adenosin-5'-yl)-P$^2$-(guanosin-5'-yl)difluoromethylenebis(phosphonate).

P$^1$-(Adenosin-5'-yl)-P$^2$-(uridin-5'-yl)difluoromethylenebis(phosphonate).

P$^1$-(Adenosin-5'-yl)-P$^2$-(cytidin-5'-yl)difluoromethylenebis(phosphonate).

P$^1$-(Adenosin-5'-yl)-P$^2$-(inosin-5'-yl)difluoromethylenebis(phosphonate).

P$^1$-(Adenosin-5'-yl)-P$^2$-(tiazofurin-5'-yl)difluoromethylenebis(phosphonate).

P¹-(Adenosin-5'-yl)-P²-(β-D-ribofuranosyl-benzene-3-carboxamide-5'-yl)difluoromethylenebis(phosphonate).

P¹-(Adenosin-5'-yl)-P²-(ψ-uridin-5'-yl)difluoromethylenebis(phosphonate).

P¹-(Adenosin-5'-yl)-P²-[5-(β-D-ribofuranosyl)nicotinamide-5'-yl]difluoromethylenebis(phosphonate).

P¹-(Adenosin-5'-yl)-P²-[6-(β-D-ribofuranosyl)picolinamide-5'-yl]difluoromethylenebis(phosphonate).

P¹-(Guanosin-5'-yl)-P²-(guanosin-5'-yl)difluoromethylenebis(phosphonate).

P¹-(Guanosin-5'-yl)-P²-(uridin-5'-yl)difluoromethylenebis(phosphonate).

P¹-(Guanosin-5'-yl)-P²-(cytidin-5'-yl)difluoromethylenebis(phosphonate).

P¹-(Guanosin-5'-yl)-P²-(inosin-5'-yl)difluoromethylenebis(phosphonate).

P¹-(Guanosin-5'-yl)-P²-(tiazofurin-5'-yl)difluoromethylenebis(phosphonate).

P¹-(Guanosin-5'-yl)-P²-(β-D-ribofuranosyl-benzene-3-carboxamide-5'-yl)difluoromethylenebis(phosphonate).

P¹-(Guanosin-5'-yl)-P²-(ψ-uridin-5'-yl)difluoromethylenebis(phosphonate).

P¹-(Guanosin-5'-yl)-P²-[5-(β-D-ribofuranosyl)nicotinamide-5'-yl]difluoromethylenebis(phosphonate).

P¹-(Guanosin-5'-yl)-P²-[6-(β-D-ribofuranosyl)picolinamide-5'-yl]difluoromethylenebis(phosphonate).

P¹-(Inosin-5'-yl)-P²-(uridin-5'-yl)difluoromethylenebis(phosphonate).

P¹-(Inosin-5'-yl)-P²-(cytidin-5'-yl)difluoromethylenebis(phosphonate).

P¹-(Inosin-5'-yl)-P²-(inosin-5'-yl)difluoromethylenebis(phosphonate).

P¹-(Inosin-5'-yl)-P²-(tiazofurin-5'-yl)difluoromethylenebis(phosphonate).

P¹-(Inosin-5'-yl)-P²-(β-D-ribofuranosyl-benzene-3-carboxamide-5'-yl)difluoromethylenebis(phosphonate).

P¹-(Uridin-5'-yl)-P²-(guanosin-5'-yl)difluoromethylenebis(phosphonate).

P¹-(Uridin-5'-yl)-P²-(cytidin-5'-yl)difluoromethylenebis(phosphonate).

P¹-(Uridin-5'-yl)-P²-(uridin-5'-yl)difluoromethylenebis(phosphonate).

P¹-(Uridin-5'-yl)-P²-(tiazofurin-5'-yl)difluoromethylenebis(phosphonate).

P¹-(Cytidin-5'-yl)-P²-(cytidin-5'-yl)difluoromethylenebis(phosphonate).

P¹-(Cytidin-5'-yl)-P²-(tiazofurin-5'-yl)difluoromethylenebis(phosphonate).

P¹-(Cytidin-5'-yl)-P²-(β-D-ribofuranosyl-benzene-3-carboxamide-5'-yl)difluoromethylenebis(phosphonate).

P¹-(Tiazofurin-5'-yl)-P²-(3'-deoxy-3'-fluoroadenosin-5'-yl)difluoromethylenebis(phosphonate).

P¹-(Tiazofurin-5'-yl)-P²-(2'-deoxy-2'-fluoroadenosin-5'-yl)difluoromethylenebis(phosphonate).

P¹-(Tiazofurin-5-yl)-P²-[9-(2'-deoxy-2'-fluoro-β-D-arabinofuranosyl)adenin-5'-yl]difluoromethylenebis(phosphonate).

P¹-(Tiazofurin-5'-yl)-P²-[9-(3'-deoxy-3'-fluoro-β-D-xylofuranosyl)adenin-5'-yl]difluoromethylenebis(phosphonate).

P¹-(β-D-Ribofuranosylbenzene-3-carboxamide-5'-yl)-P²-[9-(2'-deoxy-2'-fluoroadenosin-5'-yl]difluoromethylenebis(phosphonate).

P¹-(β-D-Ribofuranosylbenzene-3-carboxamide-5'-yl)-P²-[9-(deoxy-3'-fluoroadenosin-5'-yl]difluoromethylenebis(phosphonate).

P¹-(β-D-Ribofuranosylbenzene-3-carboxamide-5'-yl)-P²-[9-(3'-deoxy-3'-fluoro-β-D-arabinofuranosyl)adenin-5'-yl]difluoromethylenebis(phosphonate).

P¹-(β-D-Ribofuranosylbenzene-3-carboxamide-5'-yl)-P²-[9-(3'-deoxy-3'-fluoro-β-D-xylofuranosyl)adenin-5'-yl]-difluoromethylenebis(phosphonate).

EXAMPLE 7

Preparation of P³-(2',3'-isopropylideneadenosin-5'-yl)-P²-(benzyl 2,3-isopropylidene-β-D-ribosid-5-yl) methylenebis(phosphonate)

This Example illustrates the reaction of a BTA with a carbohydrate giving an analogue of the nucleoside diphosphate carbohydrate type.

Benzyl 2,3-O-isopropylidene-D-ribofuranoside (420 mg, 1.5 mmol) is added to a solution of BTA prepared from adenosin-5'-yl phosphonomethylenephosphonic acid (1.0 mmol in 5 ml of pyridine) as described in Example 1. The mixture is kept at 55° C. for three hours until the $^{31}$P NMR spectrum of the reaction mixure shows two broad multiplets at δ 8–9 and 18–21 ppm characteristic for a P¹,P²,P³,P⁴ tetrasubstituted methylenebis(phosphonic acid) anhydride intermediate. The reaction is quenched by addition of ater (1 ml), and the mixture is left for additional 1–2 hour at room temperature until the $^{31}$P NMR spectrum shows the presence of the desired product (one broad singlet at 17 ppm). The whole mixture is diluted with 5 ml of water and extracted with ethyl ether. The aqueous layer is separated, and the product purified by HPLC. After HPLC purification, P¹-(2', 3'-isopropylidene-adenosin-5'-yl)-P²-(benzyl 2,3-isopropylidene-β-D-ribosid-5-yl) methylenebis(phosphonate) is obtained (72%, retention time 52 min).

$^{31}$P NMR (D$_2$O) δ: 17.47 (doublet, J$_{PCP}$=10.8 Hz), 17.73 (doublet, J$_{PCP}$=10.8 Hz). $^1$H NMR (D$_2$O) δ: 1.21 and 3.12 (Et$_3$NH⁺), 1.23, 1.37, 1.40 and 1.62 (3H each, Meisopropylidene), 2.09 (2H, t, P—CH$_2$—P, J$_{P-H}$=20.0 Hz,), 3.8 (2H, m, H5, 5', ribose), 4.05 (2H, t, H5', 5", J$_{4',5'}$=J$_{4',5"}$=4.6 Hz, Ado), 4.27 (1H, t, H4, ribose, J$_{4,5}$=J$_{4,5'}$=7.7, Hz), 4.30 and 4.50 (2H, two d, PhCH$_2$, J=11.4 Hz), 4.55 (1H, m, H-4', Ado), 4.56 (1H, d, H-3, J$_{2,3}$=6.0 Hz, ribose), 4.78 (1H, d, H-2, ribose), 5.06 (1H, s, H-1, ribose), 5.12 (1H, dd, H-3', J$_{3',4'}$=2.2 Hz, Ado), 5.25 (1H, dd, H-2', J$_{2',3}$=6.2 Hz, Ado ), 6.09 (1H, d, H-1', J$_{1',2'}$=3.5 Hz, Ado ), 7.22 (5H, m, phenyl), 8.06 (1H, s, H-8, Ado), 8.37 (lH, s, H-2, Ado).

In a similar manner, the same compound was obtained in 82% yield by treatment of BTA derived from benzyl 2,3-O-isopropylidene-β-D-ribofuranosid-5-ylphosphonomethylenephosphonic acid with 2',3'-O-isopropylideneadenosine.

The following protected P¹,P²-disubstituted methylenebis (phosphonate) analogues are synthesized by following the same procedure but using the corresponding BTA and nucleophiles:

P$^1$-(2',3'-O-Isopropylideneadenosin-5'-yl)-P$^2$-( 2,3-O-isopropylidene-D-ribonolacton-5-yl)methylenebis(phosphonate).

P$^1$-(2',3'-O-Isopropylideneguanosin-5'-yl)-P$^2$-(2,3,4,6-tetra-O-acetyl-α-D-mannopyranosyl)methylenebis(phosphonate).

P$^1$-(2',3'-O-Isopropylideneinosin-5'-yl)-P$^2$-(2,3-O-isopropylidene-D-ribonolacton-5-yl)methylenebis(phosphonate).

P$^1$-(2',3'-O-Isopropylideneguanosin-5'-yl)-P$^2$-(2,3-O-isopropylidene-D-ribonolacton-5-yl)methylenebis(phosphonate).

P$^1$-(2',3'-O-Isopropylideneuridin-5'-yl) P$^2$-(2,3-O-isopropylidene-D-ribonolacton-5-yl)methylenebis(phosphonate).

P$^1$-(2',3'-O-Isopropylideneuridin-5'-yl)-P$^2$-(2,3,4,6-tetra-O-acetyl-β-D-gluocopyranosyl)methylenebis(phosphonate).

P$^1$-(2',3'-O-Isopropylideneuridin-5'-yl)-P$^2$-(2,3,4,6-tetra-O-acetyl-α-D-glucopyranosyl)methylenebis(phosphonate).

P$^1$-(2',3'-O-Isopropylideneuridin-5'-yl)-P$^2$-(2-acetamido-3,4,6-tri-O-acetyl-2-deoxy-β-D-gluocopyranosyl)methylenebis(phosphonate).

P$^1$-(2',3'-O-Isopropylideneuridin-5'-yl)-P$^2$-(2-acetamido-3,4,6-tri-O-acetyl-2-deoxy-α-D-glucopyranosyl)methylenebis(phosphonate).

P$^1$-(2',3'-O-Isopropylideneuridin-5'-yl)-P$^2$-(2,3,4,6-tetra-O-acetyl-β-D-galactopyranosyl)methylenebis(phosphonate).

P$^1$-(2',3'-O-Isopropylideneuridin-5'-yl)-P$^2$-(2,3,4,6-tetra-O-acetyl-α-D-galactopyranosyl)methylenebis(phosphonate).

P$^1$-(2',3'-O-Isopropylideneuridin-5'-yl)-P$^2$-(2-acetamido-3,4,6-tri-O-acetyl-2-deoxy-β-D-galactopyranosyl)methylenebis(phosphonate).

P$^1$-(2',3'-O-Isopropylideneuridin-5'-yl)-P$^2$-(2-acetamido-3,4,6-tri-O-acetyl-2-deoxy-α-D-galactopyranosyl)methylenebis(phosphonate).

P$^1$-(2',3'-O-Isopropylideneuridin-5'-yl)-P$^2$-(2,3,4,6-tetra-O-acetyl-β-D-gluocopyranosyl)difluoromethylenebis(phosphonate).

P$^1$-(2',3'-O-Isopropylideneuridin-5'-yl)-P$^2$-(2,3,4,6-tetra-O-acetyl-α-D-glucopyranosyl)difluoromethylenebis(phosphonate).

P$^1$-(2',3'-O-Isopropylideneadenosin-5'-yl)-P$^2$-(2,3-O-isopropylidene-D-ribonolacton-5-yl)difluoromethylenebis(phosphonate).

P$^1$-(2',3'-O-Isopropylideneguanosin-5'-yl)-P$^2$-(2,3-O-isopropylidene-D-ribonolacton-5-yl)difluoromethylenebis(phosphonate).

P$^1$-(2',3'-O-Isopropylideneguanosin-5'-yl)-P$^2$-(2,3,4,6-tetra-O-acetyl-α-D-mannopyranosyl)difluoromethylenebis(phosphonate).

P$^1$-(2',3'-O-Isopropylideneinosin-5'-yl)-P$^2$-(2,3-O-isopropylidene-D-ribonolacton-5-yl)difluoromethylenebis(phosphonate).

P$^1$-(2',3'-O-Isopropylideneuridin-5'-yl)-P$^2$-(2,3-O-isopropylidene-D-ribonolacton-5-yl)difluoromethylenebis(phosphonate).

P$^1$-(2',3'-O-Isopropylideneuridin-5'-yl)-P$^2$-(2-acetamido-3,4,6-tri-O-acetyl-2-deoxy-β-D-gluocopyranosyl)difluoromethylenebis(phosphonate).

P$^1$-(2',3'-O-Isopropylideneuridin-5'-yl)-P$^2$-(2-acetamido-3,4,6-tri-O-acetyl-2-deoxy-α-D-glucopyranosyl)difluoromethylenebis(phosphonate).

P$^1$-(2',3'-O-Isopropylideneuridin-5'-yl)-P$^2$-(2,3,4,6-tetra-O-acetyl-β-D-galactopyranosyl)difluoromethylenebis(phosphonate).

P$^1$-(2',3'-O-Isopropylideneuridin-5'-yl)-P$^2$-(2,3,4,6-tetra-O-acetyl-α-D-galactopyranosyl)difluoromethylenebis(phosphonate).

P$^1$-(2',3'-O-Isopropylideneuridin-5'-yl)-P$^2$-(2-acetamido-3,4,6-tri-O-acetyl-2-deoxy-β-D-galactopyranosyl)difluoromethylenebis(phosphonate).

P$^1$-(2',3'-O-Isopropylideneuridin-5'-yl)-P$^2$-(2-acetamido-3,4,6-tri-O-acetyl-2-deoxy-α-D-galactopyranosyl)difluoromethylenebis(phosphonate)

EXAMPLE 8

P$^1$-(Adenosin-5'-yl)-P$^2$-(D-ribose-5-yl)methylenebis(phosphonate) An Analogue of ADP-ribose P$^1$-(2',3'-Isopropylideneadenosin-5'-yl)-P$^2$-(benzyl 2,3-O-isopropylidene-β-D-ribosid-5-yl)methylenebis(phosphonate) is deprotected as described in Example 4. The free acid thus obtained is a 1:2 mixture of α and β anomers which is further converted into the Na salt by passing through a column of Dowex 50WX8 (Na$^+$). The overall yield is 91.3%. $^{31}$P NMR (D$_2$O) 18.0 ppm (brs); $^1$H NMR (D$_2$O) δ 2.18 (0.7H, t, CH$_2$P, J$_{P,CH}$= 19.9 Hz, α-anomer), 2.20 (1.3H, t, CH$_2$P, J$_{P,CH}$=19.9 Hz, β-anomer), 3.8–4.8 (10H, all H's of sugars except H1 of ribose and H1' of adenosine), 5.18 (0.66H, d, H1 of β-ribose, J$_{1,2}$=1.6 Hz), 5.30 (0.33H, d, H1 of α-ribose, J$_{1,2}$=4.0 Hz), 6.05 (0.66H, d, H1' of β-anomer J$_{1',2'}$=5.1 Hz), 6.0 (0.33H, d, H1' α-anomer, J$_{1',2'}$=4.1 Hz), 8.16 and 8.50 (2×1H signals, H2 and H8 of adenine).

The following P$^1$,P$^2$-disubstituted methylenebis(phosphonate) analogues are synthesized by following the same procedure but using the corresponding BTA and nucleophiles:

P$^1$-(Adenosin-5'-yl)-P$^2$-(D-ribonolacton-5-yl)methylenebis(phosphonate).

P$^1$-(Guanosin-5'-yl)-P$^2$-(α-D-mannopyranosyl)methylenebis(phosphonate).

P$^1$-(Inosin-5'-yl)-P$^2$-(D-ribonolacton-5-yl)methylenebis(phosphonate).

P$^1$-(Guanosin-5'-yl)-P$^2$-(D-ribonolacton-5-yl)methylenebis(phosphonate).

P$^1$-(Uridin-5'-yl)-P$^2$-(D-ribonolacton-5-yl)methylenebis(phosphonate).

P$^1$-(Uridin-5'-yl)-P$^2$-(β-D-gluocopyranosyl)methylenebis(phosphonate).

P$^1$-(Uridin-5'-yl)-P$^2$-(α-D-glucopyranosyl)methylenebis(phosphonate). P$^1$-(Uridin-5'-yl)-P$^2$-(2-acetamido-2-deoxy-β-D-gluocopyranosyl)methylenebis(phosphonate).

P$^1$-(Uridin-5'-yl)-P$^2$-(2-acetamido-2-deoxy-α-D-glucopyranosyl)methylenebis(phosphonate).

P$^1$-(Uridin-5'-yl)-P$^2$-(β-D-galactopyranosyl)methylenebis(phosphonate).

P$^1$-(Uridin-5'-yl)-P$^2$-(α-D-galactopyranosyl)methylenebis(phosphonate).

P$^1$-(Uridin-5'-yl)-P$^2$-(2-acetamido-2-deoxy-β-D-galactopyranosyl)methylenebis(phosphonate).

P$^1$-(Uridin-5'-yl)-P$^2$-(2-acetamido- 2-deoxy-α-D-galactopyranosyl)methylenebis(phosphonate).

P$^1$-(Uridin-5'-yl)-P$^2$-(β-D-gluocopyranosyl)difluoromethylenebis(phosphonate).

P$^1$-(Uridin-5'-yl)-P$^2$-(α-D-glucopyranosyl)difluoromethylenebis(phosphonate).

P$^1$-(Adenosin-5'-yl)-P$^2$-(D-ribonolacton-5-yl)difluoromethylenebis(phosphonate).

P$^1$-(Guanosin-5'-yl)-P$^2$-(-D-ribonolacton-5-yl)difluoromethylenebis(phosphonate).

P$^1$-(Guanosin-5'-yl)-P$^2$-(α-D-mannopyranosyl)difluoromethylenebis(phosphonate).

P$^1$-(Inosin-5'-yl)-P$^2$-(D-ribonolacton-5-yl)difluoromethylenebis(phosphonate).

P$^1$-(Uridin-5'-yl)-P$^2$-(D-ribonolacton-5-yl)difluoromethylenebis(phosphonate).

P$^1$-(Uridin-5'-yl)-P$^2$-(2-acetamido-2-deoxy-β-D-gluocopyranosyl)difluoromethylenebis(phosphonate).

P$^1$-(Uridin-5'-yl)-P$^2$-(2-acetamido-2-deoxy-α-D-glucopyranosyl)difluoromethylenebis(phosphonate).

P$^1$-(Uridin-5'-yl)-P$^2$-(β-D-galactopyranosyl)difluoromethylenebis(phosphonate).

P$^1$-(Uridin-5'-yl)-P$^2$-(α-D-galactopyranosyl)difluoromethylenebis(phosphonate).

P$^1$-(Uridin-5'-yl)-P$^2$-(2-acetamido-2-deoxy-β-D-galactopyranosyl)difluoromethylenebis(phosphonate).

P$^1$-(Uridin-5'-yl)-P$^2$-(2-acetamido-2-deoxy-α-D-galactopyranosyl)difluoromethylenebis(phosphonate).

EXAMPLE 9

P$^1$-(N$^4$-Acetyl-2',3'-O-isopropylidenecytidin-5'-yl)-P$^2$-(N-acetylaminoethyl)methylenebis(phosphonate)

This Example illustrates the synthesis of an important intermediate in lipid metabolism by reaction of a proper BTA with an N-protected aminoalkanol.

A mixture of BTA prepared from N$^4$-acetylcytidin-5'-ylphosphonomethylenephosphonic acid (1 mmol in 10 ml of dry pyridine) and N-acetylethanolamine (155 mg, 1.5 mmol) is kept at 55° C. for 4 hours. The mixture is processed as described in Example 3. P$^1$-(N$^4$-acetyl-2',3'-O-isopropylidenecytidin-5'-yl)-P$^2$-(N-acetylaminoethyl)methylenebisphosphonate is obtained in 75% yield after HPLC purification (retention time 38 min) $^{31}$P NMR (D$_2$O) δ [ppm]: 17.73 (broad singlet). $^1$H NMR(D$_2$O) δ [ppm]: 1.23 and 3.15 (Et$_3$NH$^+$), 1.37 and 1.57 (3H each, isopropylidene CH$_3$), 1.89 (3H, s, N-Ac), 2.05 (2H, t, J$_{PCH}$=19.8 Hz, CH$_2$—P), 2.19 (3H, s, N$^4$-Ac), 3.31 (2H, m, CH$_2$—N, ethanoloamine), 3.89 (2H, m, CH$_2$—O—P, ethanoloamine), 4.07 (1H, dd, H5', J$_{5',5''}$=11.5 Hz, J$_{4',5'}$=2.0 Hz), 4.14 (1H, d, H-5'', J$_{5',5''}$=11.6 Hz), 4.69 (1H, bs, H-4'), 4.95 (1H, dd, H-2' J$_{2',3'}$=6.1 Hz,), 5.01 (1H, dd, H-3', J$_{3',4'}$=1.4 Hz), 5.85 (1H, d, H-1', J$_{1',2'}$=2.2 Hz), 7.31, 8.29 (1H each, d, H-5, H-6, J=7.6 Hz,).

By following the same procedure but using the corresponding BTA and N-protected alkanolamine, the following derivatives are prepared:

P$^1$-(2',3'-O-Isopropylideneadenosin-5'-yl)-P$^2$-(N-acetylaminoethyl)methylenebis(phosphonate).

P$^1$-(2',3'-O-Isopropylideneguanosin-5'-yl)-P$^2$-(N-acetylaminoethyl)methylenebis(phosphonate).

P$^1$-(2',3'-O-Isopropylideneinosin-5'-yl)-P$^2$-(N-acetylaminoethyl)methylenebis(phosphonate).

P$^1$-(2',3'-O-Isopropylideneuridin-5'-yl)-P$^2$-(N-acetylaminoethyl)methylenebis(phosphonate).

P$^1$-(2',3'-O-Isopropylidene-N$^4$-acetylcytidin-5'-yl)-P$^2$-(N-acetylaminopropyl)methylenebis(phosphonate).

P$^1$-(2',3'-O-Isopropylideneadenosin-5'-yl)-P$^2$-(N-acetylaminopropyl)methylenebis(phosphonate).

P$^1$-(2',3'-O-Isopropylideneguanosin-5'-yl)-P$^2$-(N-acetylaminopropylmethylenebis(phosphonate).

P$^1$-(2',3'-O-Isopropylideneinosin-5'-yl)-P$^2$-(N-acetylaminopropyl)methylenebis(phosphonate).

P$^1$-(2',3'-O-Isopropylideneuridin-5'-yl)-P$^2$-(N-acetylaminopropyl)methylenebis(phosphonate).

P$^1$-(2',3'-O-Isopropylidene-N$^4$-acetylcytidin-5'-yl)-P$^2$-(N-acetylaminobutyl)methylenebis(phosphonate).

P$^1$-(2',3'-O-Isopropylideneadenosin-5'-yl)-P$^2$-(N-acetylaminobutyl)methylenebis(phosphonate).

P$^1$-(2',3'-O-Isopropylideneguanosin-5'-yl)-P$^2$-(N-acetylaminobutyl)methylenebis(phosphonate).

P$^1$-(2',3'-O-Isopropylideneinosin-5'-yl)-P$^2$-(N-acetylaminobutyl)methylenebis(phosphonate).

P$^1$-(2',3'-O-Isopropylideneuridin-5'-yl)-P$^2$-(N-acetylaminobutyl)methylenebis(phosphonate).

P$^1$-(2',3'-O-Isopropylidene-N$^4$-acetylcytidin-5'-yl)-P$^2$-(N-benzyloxycarbonylaminoethyl)methylenebis(phosphonate).

P$^1$-(2',3'-O-Isopropylideneadenosin-5'-yl)-P$^2$-(N-benzyloxycarbonylaminoethyl)methylenebis(phosphonate).

P$^1$-(2',3'-O-Isopropylideneguanosin-5'-yl)-P$^2$-(N-benzyloxycarbonylaminoethyl)methylenebis(phosphonate).

P$^1$-(2',3'-O-Isopropylideneinosin-5'-yl)-P$^2$-(N-benzyloxycarbonylaminoethyl)methylenebis(phosphonate).

P$^1$-(2',3'-O-Isopropylideneuridin-5'-yl)-P$^2$-(N-benzyloxycarbonylaminoethyl)methylenebis(phosphonate).

P$^1$-(2',3'-O-Isopropylidene-N$^4$-acetylcytidin-5'-yl)-P$^2$-(N-benzyloxycarbonylaminopropyl)methylenebis(phosphonate).

P$^1$-(2',3'-O-Isopropylideneadenosin-5'-yl)-P$^2$-(N-benzyloxycarbonylaminopropyl)methylenebis(phosphonate).

P$^1$-(2',3'-O-Isopropylideneguanosin-5'-yl)-P$^2$-(N-benzyloxycarbonylaminopropyl)methylenebis(phosphonate).

P$^1$-(2',3'-O-Isopropylideneinosin-5'-yl)-P$^2$-(N-benzyloxycarbonylaminopropyl)methylenebis(phosphonate).

P$^1$-(2',3'-O-Isopropylideneuridin-5'-yl)-P$^2$-(N-benzyloxycarbonylaminopropyl)methylenebis(phosphonate).

P$^1$-(2',3'-O-Isopropylidene-N$^4$-acetylcytidin-5'-yl)-P$^2$-(N-benzyloxycarbonylaminobutyl)methylenebis(phosphonate).

P$^1$-(2',3'-O-Isopropylideneadenosin-5'-yl)-P$^2$-(N-benzyloxycarbonylaminobutyl)methylenebis(phosphonate).

P$^1$-(2',3'-O-Isopropylideneguanosin-5'-yl)-P$^2$-(N-benzyloxycarbonylaminobutyl)methylenebis(phosphonate).

P$^1$-(2',3'-O-Isopropylideneinosin-5'-yl)-P$^2$-(N-benzyloxycarbonylaminobutyl)methylenebis(phosphonate).

P¹-(2',3'-O-Isopropylideneuridin-5'-yl)-P²-(N-benzyloxycarbonylaminobutyl)methylenebis(phosphonate).

P¹-(2',3'-O-Isopropylidene-N⁴-acetylcytidin-5'-yl)-P²-(N-butoxycarbonylaminoethyl)methylenebis(phosphonate).

P¹-(2',3'-O-Isopropylideneadenosin-5'-yl)-P²-(N-butoxycarbonylaminoethyl)methylenebis(phosphonate).

P¹-(2',3'-O-Isopropylideneguanosin-5'-yl)-P²-(N-butoxycarbonylaminoethyl)methylenebis(phosphonate).

P¹-(2',3'-O-Isopropylideneinosin-5'-yl)-P²-(N-butoxycarbonylaminoethyl)methylenebis(phosphonate).

P¹-(2',3'-O-Isopropylideneuridin-5'-yl)-P²-(N-butoxycarbonylaminoethy)methylenebis(phosphonate).

P¹-(2',3'-O-Isopropylidene-N⁴-acetylcytidin-5'-yl)-P²-(N-butoxycarbonylaminopropyl)methylenebis(phosphonate).

P¹-(2',3'-O-Isopropylideneadenosin-5'-yl)-P²-(N-butoxycarbonylaminopropyl)methylenebis(phosphonate).

P¹-(2',3'-O-Isopropylideneguanosin-5'-yl)-P²-(N-butoxycarbonylaminopropyl)methylenebis(phosphonate).

P¹-(2',3'-O-Isopropylideneinosin-5'-yl)-P²-(N-utoxycarbonylaminopropyl)methylenebis(phosphonate).

P¹-(2',3'-O-Isopropylideneuridin-5'-yl)-P²-(N-butoxycarbonylaminopropyl)methylenebis(phosphonate).

P¹-(2',3'-O-Isopropylideiie-N⁴-acetylcytidin-5'-yl)-P²-(N-butoxycarbonylaminobutyl)methylenebis(phosphonate).

P¹-(2',3'-O-Isopropylideneadenosin-5'-yl)-P²-(N-butoxycarbonylaminobutyl)methylenebis(phosphonate).

P¹-(2',3'-O-Isopropylideneguanosin-5'-yl)-P²-(N-butoxycarbonylaminobutyl)methylenebis(phosphonate).

P¹-(2',3'-O-Isopropylideneinosin-5'-yl)-P²-(N-butoxycarbonylaminobutyl)methylenebis(phosphonate).

P¹-(2',3'-O-Isopropylideneuridin-5'-yl)-P²-(N-butoxycarbonylaminobutyl)methylenebis(phosphonate).

EXAMPLE 10

P¹-(Cytidin-5'-yl)-P²-(N-acetylaminoethyl)methylenebis(phosphonate)

P¹-(N⁴-Acetyl-2',3'-O-isopropylidene-cytidin-5'-yl)-P²-(N-acetylaminoethyl)methylenebis-(phosphonate) is deprotected as described in Example 8, and the product isolated as the Na salt in 95% yield. ³¹P NMR (D₂O) 18.01 and 18.05 ppm (AB system $J_{AB}$=10.8 Hz). ¹H NMR (D₂O) δ 1.97 (3H, s, NAc), 2.18 (2H, t, PCH₂P, $J_{P,CH}$=19.8 Hz), 3.38 (2H, t, CH₂N, J=5.4 Hz), 3.95 (2H, m, CH₂OP), 4.10–4.36 (5H, m, H2',3',4',5',5"), 5.96 (1H, d, H1', $J_{1',2'}$=3.6 Hz), 6.10 (1H, d, H6, $J_{5,6}$=7.6 Hz), 8.00 (1H, d, H5, $J_{5,6}$=7.6 Hz).

By following the same procedure the following derivatives are prepared:

P¹-(Adenosin-5'-yl)-P²-(N-acetylaminoethyl)methylenebis(phosphonate).

P¹-(Guanosin-5'-yl)-P²-(N-acetylaminoethyl)methylenebis(phosphonate).

P¹-(Inosin-5'-yl)-P²-(N-acetylaminoethyl)methylenebis(phosphonate).

P¹-(Uridin-5'-yl)-P²-(N-acetylaminoethyl)methylenebis(phosphonate).

P¹-(Cytidin-5'-yl)-P²-(N-acetylaminopropyl)methylenebis(phosphonate).

P¹-(Adenosin-5'-yl)-P²-(N-acetylaminopropyl)methylenebis(phosphonate).

P¹-(Guanosin-5'-yl)-P²-(N-acetylaminopropyl)methylenebis(phosphonate).

P¹-(Inosin-5'-yl)-P²-(N-acetylaminopropyl)methylenebis(phosphonate).

P¹-(Uridin-5'-yl)-P²-(N-acetylaminopropyl)methylenebis(phosphonate).

P¹-(Cytidin-5'-yl)-P²-(N-acetylaminobutyl)methylenebis(phosphonate).

P¹-(Adenosin-5'-yl)-P²-(N-acetylaminobutyl)methylenebis(phosphonate).

P¹-(Guanosin-5'-yl)-P²-(N-acetylaminobutyl)methylenebis(phosphonate).

P¹-(Inosin-5'-yl)-P²-(N-acetylaminobutyl)methylenebis(phosphonate).

P¹-(Uridin-5'-yl)-P²-(N-acetylaminobutyl)methylenebis(phosphonate).

P¹-(Cytidin-5'-yl)-P²-(N-benzyloxycarbonylaminoethyl)methylenebis(phosphonate).

P¹-(Adenosin-5'-yl)-P²-(N-benzyloxycarbonylaminoethyl)methylenebis(phosphonate).

P¹-(Guanosin-5'-yl)-P²-(N-benzyloxycarbonylaminoethyl)methylenebis(phosphonate).

P¹-(Inosin-5'-yl)-P²-(N-benzyloxycarbonylaminoethyl)methylenebis(phosphonate).

P¹-(Uridin-5'-yl)-P²-(N-benzyloxycarbonylaminoethyl)methylenebis(phosphonate).

P¹-(Cytidin-5'-yl)-P²-(N-benzyloxycarbonylaminopropyl)methylenebis(phosphonate).

P¹-(Adenosin-5'-yl)-P²-(N-benzyloxycarbonylaminopropyl)methylenebis(phosphonate).

P¹-(Guanosin-5'-yl)-P²-(N-benzyloxycarbonylaminopropyl)methylenebis(phosphonate).

P¹-(Inosin-5'-yl)-P²-(N-benzyloxycarbonylaminopropyl)methylenebis(phosphonate).

P¹-(Uridin-5'-yl)-P²-(N-benzyloxycarbonylaminopropyl)methylenebis(phosphonate).

P¹-(Cytidin-5'-yl)-P²-(N-benzyloxycarbonylaminobutyl)methylenebis(phosphonate).

P¹-(Adenosin-5'-yl)-P²-(N-benzyloxycarbonylaminobutyl)methylenebis(phosphonate).

P¹-(Guanosin-5'-yl)-P²-(N-benzyloxycarbonylaminobutyl)methylenebis(phosphonate).

P¹-(Inosin-5'-yl)-P²-(N-benzyloxycarbonylaminobutyl)methylenebis(phosphonate).

P$^1$-(Uridin-5'-yl)-P$^2$-(N-benzyloxycarbonylaminobutyl) methylenebis(phosphonate).

P$^1$-(Cytidin-5'-yl)-P$^2$-(N-butoxycarbonylaminoethyl) methylenebis(phosphonate).

P$^1$-(Adenosin-5'-yl)-P$^2$-(N-butoxycarbonylaminoethyl) methylenebis(phosphonate).

P$^1$-(Guanosin-5'-yl)-P$^2$-(N-butoxycarbonylaminoethyl) methylenebis(phosphonate).

P$^1$-(Inosin-5'-yl)-P$^2$-(N-butoxycarbonylaminoethyl) methylenebis(phosphonate).

P$^1$-(Uridin-5'-yl)-P$^2$-(N-butoxycarbonylaminoethy) methylenebis(phosphonate).

P$^1$-(Cytidin-5-yl)-P$^2$-(N-butoxycarbonylaminopropyl) methylenebis(phosphonate).

P$^1$-(Adenosin-5'-yl)-P$^2$-(N-butoxycarbonylaminopropyl) methylenebis(phosphonate).

P$^1$-(Guanosin-5'-yl)-P$^2$-(N-butoxycarbonylaminopropyl) methylenebis(phosphonate).

P$^1$-(Inosin-5'-yl)-P$^2$-(N-butoxycarbonylaminopropyl) methylenebis(phosphonate).

P$^1$-(Uridin-5'-yl)-P$^2$-(N-butoxycarbonylaminopropyl) methylenebis(phosphonate).

P$^1$-(Cytidin-5'-yl)-P$^2$-(N-butoxycarbonylaminobutyl) methylenebis(phosphonate).

P$^1$-(Adenosin-5'-yl)-P$^2$-(N-butoxycarbonylaminobutyl) methylenebis(phosphonate).

P$^1$-(Guanosin-5'-yl)-P$^2$-(N-butoxycarbonylaminobutyl) methylenebis(phosphonate).

P$^1$-(Inosin-5'-yl)-P$^2$-(N-butoxycarbonylaminobutyl) methylenebis(phosphonate).

P$^1$-(Uridin-5'-yl)-P$^2$-(N-butoxycarbonylaminobutyl) methylenebis(phosphonate).

EXAMPLE 11

Preparation of Protected Methylenebis (phosphonate) Analogue of Flavin Adenine Dinucleotide (FAD).

This Example illustrates that BTA can react with the primary hydroxyl group of polyhydroxy carbohydrate derivatives such as riboflavin type to form analogues of the coenzyme flavin adenine dinucleotide, FAD.

Riboflavin (0.14 mmol, 50 mg) is added to an NMR tube containing the solution of BTA derived from 2',3'-O-isopropylideneadenosine 5'-phosphonylmethylenephosphonate (0.05 mmol in 0.7 ml of Py-d$_5$). The mixture is kept for 10 hours at 60° C., 12 hours at 36° C. and 3 days at room temperature until a $^{31}$P NMR spectrum shows only two groups of signals at 5–10 ppm and 40–45 ppm. Water is added to a final concentration of 20% and the mixture is left for additional hour at room temperature. $^{31}$P NMR shows a presence of multiple AB signals centered at 17 ppm. The mixture is diluted with 10 ml of water, extracted with ethyl ether and evaporated to dryness. The residue is resuspended in 3 ml of water, filtered and the solution is purified by HPLC. Three components are collected: riboflavin (retention time 45 minutes) and two other (47 and 48 minutes) containing both riboflavin and adenosine residues. The slowest migrating product is the desired methylenebisphosphonate analogue of 2',3'-O-isopropylidene FAD. It is converted into the sodium salt by passing through a column of Dowex 50WX8 Na$^+$-form. Yield is 5 mg (12.5%). $^1$H NMR (D$_2$O), δ 1.40 (s, 3H, iPr), 1.63 (s, 3H, iPr), 2.21 (t, 2H, P—CH$_2$—P, J$_{P,H}$=19.8 Hz), 2.32 (s, 3H, CH$_3$), 2.39 (s, 3H, CH$_3$), 3.89–4.06 (m, 3H, H4", H5",H5"), 4.13–4.24 (m, 3H, H3".H5',H5'), 4.30–4.38 (m, 1H, H2"), 4.42 (d, 1H, H1", J$_{1",1"}$=13.9 Hz), 4.57 (m, 1H, H4'), 4.97 (dd, 1H, H1", J$_{1",1"}$=13.9 Hz, J$_{1",2"}$=11.4 Hz), 5.11–5.18 (m, 2H, H2',H3'), 5.93 (d, 1H, H1', J$_{1',2'}$=2.9 Hz), 7.55, 7.61 (two 1H singlets, flavin), 7.86, 8.28 (two 1H singlets, H2, H8 adenine), $^{31}$P NMR (D$_2$O) δ 18.11, 18.63, AB system, J$_{P,P}$=11.7 Hz).

By following the same procedure but using the corresponding BTA and O-unprotected polyhydroxyl derivative, the following derivatives are prepared:

P$^1$-(2',3'-O-Isopropylideneadenosin-5'-yl)-P$^2$-(ethyl 2,4-dihydroxy-3,3-dimethylbutyrate-4-yl)methylenebis (phosphonate).

P$^1$-(2',3'-O-Isopropylideneadenosin-5'-yl)-P$^2$-(2,4-dihydroxy-3,3-dimethylbutyryl-β-alanyl-β-aminoethanethiol-S-acetyl-4-yl)methylenebis (phosphonate).

P$^1$-(2',3'-O-Isopropylideneguanosin-5'-yl)-P$^2$-(riboflavin-5'-yl)methylenebis(phosphonate).

P$^1$-(2',3'-O-Isopropylideneguanosin-5'-yl)-P$^2$-(ethyl 2,4-dihydroxy-3,3-dimethylbutyrate-4-yl)methylenebis (phosphonate).

P$^1$-(2',3'-O-Isopropylideneguanosin-5'-yl)-P$^2$-(2,4-dihydroxy-3,3-dimethylbutyryl-β-alanyl-β-aminoethanethiol-S-acetyl-4-yl)methylenebis (phosphonate).

P$^1$-(2',3'-O-Isopropylideneinosin-5'-yl)-P$^2$-(riboflavin-5'-yl)methylenebis(phosphonate).

P$^1$-(2',3'-O-Isopropylideneinosin-5'-yl)-P$^2$-(ethyl 2,4-dihydroxy-3,3-dimethylbutyrate-4-yl)methylenebis (phosphonate).

P$^1$-(2',3'-O-Isopropylideneinosin-5'-yl)-P$^2$-(2,4-dihydroxy-3,3-dimethylbutyryl-β-alanyl-β-aminoethanethiol-S-acetyl-4-yl)methylenebis (phosphonate).

P$^1$-(2',3'-O-Isopropylideneuridin-5'-yl)-P$^2$-(riboflavin-5'-yl)methylenebis(phosphonate).

P$^1$-(2',3'-O-Isopropylideneuridin-5'-yl)-P$^2$-(ethyl 2,4-dihydroxy-3,3-dimethylbutyrate-4-yl)methylenebis (phosphonate).

P$^1$-(2',3'-O-Isopropylideneuridin-5'-yl)-P$^2$-(2,4-dihydroxy-3,3-dimethylbutyryl-β-alanyl-β-aminoethanethiol-S-acetyl-4-yl)methylenebis (phosphonate).

P$^1$-(2',3'-O-Isopropylidene-N$^4$-acetylcytidin-5'-yl)-P$^2$-(riboflavin-5'-yl)methylenebis(phosphonate).

P$^1$-(2',3'-O-Isopropylidene-N$^4$-acetylcytidin-5'-yl)-P$^2$-(ethyl 2,4-dihydroxy-3,3-dimethylbutyrate-4-yl) methylenebis(phosphonate).

P$^1$-(2',3'-O-Isopropylidene-N$^4$-acetylcytidin-5'-yl)-P$^2$-(2,4-dihydroxy-3,3-dimethylbutyryl-β-alanyl-β-aminoethanethiol-S-acetyl-4-yl)methylenebis (phosphonate).

EXAMPLE 12

The Methylenebis(phosphonate) Analogue of FAD

P$^1$-(2',3'-O-Isopropylideneadenosin-5-yl)-P$^2$-(riboflavin-5-yl)methylenebis(phosphonate) is deblocked by the procedure described in Example 8 to give P$^1$-(adenosin-5'-yl)-P2-(riboflavin-5'-yl)methylenebis(phosphonate) in 80% yield.

31P NMR (D$_2$O) 18.17 and 18.77 (AB system, J$_{AB}$=12.3 Hz) 1H NMR (D$_2$O) d 2.30 (2H, t, PCH$_2$P, J$_p$, CH$_2$=19.9

Hz), 2.35 (3H, s, CH$_3$), 2.41 (3H, s, CH$_3$), 3.80–5.00 (12H, m, ribitol and ribose protons), 5.81 (1H, d, H1', J$_{1',2'}$=5.1 Hz), 7.56 and 7.67 (two 1H singlets, flavin ring), 7.82 and 8.39 (two 1H singlets, H2, H8).

By following the same procedure but using the corresponding protected analogues, the following derivatives are prepared:

P$^1$-(Adenosin-5'-yl)-P$^2$-(ethyl-2,4-dihydroxy-3,3-dimethylbutyrate-4-yl)methylenebis(phosphonate).

P$^1$-(Adenosin-5'-yl)-P$^2$-(ethyl-2,4-dihydroxy-3,3-dimethylbutyryl-β-alanyl-β-aminoethanethiol-S-acetyl-4-yl)methylenebis(phosphonate).

P$^1$-(Guanosin-5'-yl)-P$^2$-(riboflavin-5'-yl)methylenebis(phosphonate).

P$^1$-(Guanosin-5'-yl)-P$^2$-(ethyl-2,4-dihydroxy-3,3-dimethylbutyrate-4-yl)methylenebis(phosphonate).

P$^1$-(Guanosin-5'-yl)-P$^2$-(2,4-dihydroxy-3,3-dimethylbutyryl-β-alanyl-β-aminoethanethiol-S-acetyl-4-yl)methylenebis(phosphonate).

P$^1$-(Inosin-5'-yl)-P$^2$-(riboflavin-5'-yl)methylenebis(phosphonate).

P$^1$-(Inosin-5'-yl)-P$^2$-(ethyl-2,4-dihydroxy-3,3-dimethylbutyrate-4-yl)methylenebis(phosphonate).

P$^1$-(Inosin-5'-yl)-P$^2$-(2,4-dihydroxy- 3,3-dimethylbutyryl-β-alanyl-β-aminoethanethiol-S-acetyl-4-yl)methylenebis(phosphonate).

P$^1$-(Uridin-5'-yl)-P$^2$-(riboflavin-5'-yl)methylenebis(phosphonate).

P$^1$-(Uridin-5'-yl)-P$^2$-(ethyl-2,4-dihydroxy-3,3-dimethylbutyrate-4-yl)methylenebis(phosphonate).

P$^1$-(Uridin-5'-yl)-P$^2$-(2,4-dihydroxy-3,3-dimethylbutyryl-β-alanyl-β-aminoethanethiol-4-yl)methylenebis(phosphonate).

P$^1$-(Cytidin-5'-yl)-P$^2$-(riboflavin-5'-yl)methylenebis(phosphonate).

P$^1$-(Cytidin-5'-yl)-P$^2$-(ethyl-2,4-dihydroxy-3,3-dimethylbutyrate-4-yl)methylenebis(phosphonate).

P$^1$-(Cytidin-5'-yl)-P$^2$-(2,4-dihydroxy-3,3-dimethylbutyryl-β-alanyl-β-aminoethanethiol-4-yl)methylenebis(phosphonate).

EXAMPLE 13

P$^1$-5'-O-(2',3'-O-Isopropylidene-N$^4$-acetylcytidin-5-yl)-P$^2$-O-(1,2-dipalmitoyl-sn-glycer-1-yl)methylenebis(phosphonate)

This Example illustrates that BTAs can react with a large lipophilic molecule such as 1,2-diacyl-sn-glycerol to give an analogue of protected cytidine diacylglycerol diphosphate, an important intermediate for the biosynthesis of lipids.

1,2-Dipalmitoyl-sn-glycerol is added to an NMR tube containing the trisanhydride solution (0.095 mmol in 1 ml of Py-d$_5$). The mixture is kept for 10 hours at 60° C. until the $^{31}$P NMR spectrum shows the presence of only two groups of signals: at 7–9 ppm and 19–21 ppm. The reaction is quenched by addition of water (0.2 ml), and the mixture is left for an additional hour at room temperature. The $^{31}$P NMR spectrum changes to a broad signal at 17 ppm. The mixture is diluted with 5 ml of water before evaporation to dryness. The residue is extracted with methanol (2 ml), and the extract is purified on a Sephadex LH-20 column (1×30 cm) with methanol as the eluent to give the product. Yield 397 OD$_{248}$ (19%). $^1$H NMR (CD$_3$OD) δ: 0.89 (t, 6H, $^3$J$_{HH}$=6.6 Hz, CH$_3$-palmitoyl), 1.28 (m, 76H, CH$_2$-palmitoyl, CH$_3$-triethylammonium), 1.34 and 1.55 (s, 3H each, CH$_3$-isopropylidene), 1.5 (m, 4H, CH$_2$CH$_2$COO—), 2.15 (t, 2H, $^2$J$_{PH}$=19.8 Hz, PCH$_2$P), 2.17 (s, 3H, acetyl), 2.28 and 2.30 (t, 2H each, $^3$J$_{HH}$=7.3 and 7.6 Hz, CH$_2$COO), 3.18 (q, 12H, $^3$J$_{HH}$=7.3, CH$_2$N), 4.07 (m, 2H, CH$_2$-3 glycerol), 4.19 (m, 3H, H-5', H-5", CH$_2$-1 glycerol), 4.48 (m, 2H, H-4', CH$_2$-1 glycerol), 4.89 (dd, 1H, $^3$J$_{HH}$=2.5 and 6.1, H-3'), 5.01 (dd, 1H, $^3$J$_{HH}$=2.5 and 6.1 Hz, H-2'), 5.24 (m, 1H, CH-2 glycerol), 6.01 (d, 1H, $^3$J$_{HH}$=2.7 Hz, H-1'), 7.45 (d, 1H, $^3$J$_{HH}$=7.5 Hz, H-5), 8.41 (d, 1H, $^3$J$_{HH}$=7.5 Hz, H-6). $^{31}$P NMR (CD$_3$OD) δ: 16.56 and 16.58, AB system, J$_{PP}$=3.5 Hz.

By following the same procedure but using the corresponding BTA and 1,2-diacyl-sn-glycerol, the following derivatives are prepared:

P$^1$-(2',3'-O-Isopropylideneadenosin-5'-yl)-P$^2$-(2,3-di-O-palmitoylglycer-1-yl)methylenebis(phosphonate).

P$^1$-(2',3'-O-Isopropylideneguanosin-5'-yl)-P$^2$-(2,3-di-O-palmitoylglycer-1-yl)methylenebis(phosphonate).

P$^1$-(2',3'-O-Isopropylideneinosin-5'-yl)-P$^2$-(2,3-di-O-palmitoylglycer-1-yl)methylenebis(phosphonate).

P$^1$-(2',3'-O-Isopropylideneuridin-5'-yl)-P$^2$-(2,3-di-O-palmitoylglycer-1-yl)methylenebis(phosphonate).

P$^1$-(2',3'-O-Isopropylideneadenosin-5'-yl)-P$^2$-(2,3-di-O-laurylglycer-1-yl)methylenebis(phosphonate).

P$^1$-(2',3'-O-Isopropylideneguanosin-5'-yl)-P$^2$-(2,3-di-O-laurylglycer-1-yl)methylenebis(phosphonate).

P$^1$-(2',3'-O-Isopropylideneinosin-5'-yl)-P$^2$-(2,3-di-O-laurylglycer-1-yl)methylenebis(phosphonate).

P$^1$-(2',3'-O-Isopropylideneuridin-5'-yl)-P$^2$-(2,3-di-O-laurylglycer-1-yl)methylenebis(phosphonate).

P$^1$-(2',3'-O-Isopropylidene-N$^4$-acetylcytidin-5'-yl)-P$^2$-(2,3-di-O-laurylglycer-1-yl)methylenebis(phosphonate).

P$^1$-(2',3'-O-Isopropylideneadenosin-5'-yl)-P$^2$-(2,3-di-O-myristoylglycer-1-yl)methylenebis(phosphonate).

P$^1$-(2',3'-O-Isopropylideneguanosin-5'-yl)-P$^2$-(2,3-di-O-myristoylglycer-1-yl)methylenebis(phosphonate).

P$^1$-(2',3'-O-Isopropylideneinosin-5'-yl)-P$^2$-(2,3-di-O-myristoylglycer-1-yl)methylenebis(phosphonate).

P$^1$-(2',3'-O-Isopropylideneuridin-5'-yl)-P$^2$-(2,3-di-O-myristoylglycer-1-yl)methylenebis(phosphonate).

P$^1$-(2',3'-O-Isopropylidene-N$^4$-acetylcytidin-5'-yl)-P$^2$-(2,3-di-O-myristoylglycer-1-yl)methylenebis(phosphonate).

P$^1$-(2',3'-O-Isopropylideneadenosin-5'-yl)-P$^2$-(2,3-di-O-stearylglycer-1-yl)methylenebis(phosphonate).

P$^1$-(2',3'-O-Isopropylideneguanosin-5'-yl)-P$^2$-(2,3-di-O-stearylglycer-1-yl)methylenebis(phosphonate).

P$^1$-(2',3'-O-Isopropylideneinosin-5'-yl)-P$^2$-(2,3-di-O-stearylglycer-1-yl)methylenebis(phosphonate).

P$^1$-(2',3'-O-Isopropylideneuridin-5'-yl)-P$^2$-(2,3-di-O-stearylglycer-1-yl)methylenebis(phosphonate).

P$^1$-(2',3'-O-Isopropylidene-N$^4$-acetylcytidin-5'-yl)-P$^2$-(2,3-di-O-stearylglycer-1-yl)methylenebis(phosphonate).

P$^1$-(2',3'-O-Isopropylideneadenosin-5'-yl)-P$^2$-(2,3-di-O-oleylglycer-1-yl)methylenebis(phosphonate).

P$^1$-(2',3'-O-Isopropylideneguanosin-5'-yl)-P$^2$-(2,3-di-O-oleylglycer-1-yl)methylenebis(phosphonate).

P$^1$-(2',3'-O-Isopropylideneinosin-5'-yl)-P$^2$-( 2,3-di-O-oleylglycer-1-yl)methylenebis(phosphonate).

P$^1$-(2',3'-O-Isopropylideneuridin-5'-yl)-P$^2$-(2,3-di-O-oleylglycer-1-yl)methylenebis(phosphonate).

P$^1$-(2',3'-O-Isopropylidene-N$^4$-acetylcytidin-5'-yl)-P$^2$-(2,3-di-O-oleylglycer-1-yl)methylenebis(phosphonate).

P$^1$-(2',3'-O-Isopropylideneadenosin-5'-yl)-P$^2$-(2,3-di-O-linoleylglycer-1-yl)methylenebis(phosphonate).

P$^1$-(2',3'-O-Isopropylideneguanosin-5'-yl)-P$^2$-(2,3-di-O-linoleylglycer-1-yl)methylenebis(phosphonate).

P$^1$-(2',3'-O-Isopropylideneinosin-5'-yl)-P$^2$-(2,3-di-O-linoleylglycer-1-yl)methylenebis(phosphonate).

P$^1$-(2',3'-O-Isopropylideneuridin-5'-yl)-P$^2$-(2,3-di-O-linoleylglycer-1-yl)methylenebis(phosphonate).

P$^1$-(2',3'-O-Isopropylidene-N$^4$-acetylcytidin-5'-yl)-P$^2$-(2,3-di-O-linoleylglycer-1-yl)methylenebis(phosphonate).

P$^1$-(2',3'-O-Isopropylideneadenosin-5'-yl)-P$^2$-(2,3-di-O-linolenylglycer-1-yl)methylenebis(phosphonate).

P$^1$-(2',3'-O-Isopropylideneguanosin-5'-yl)-P$^2$-(2,3-di-O-linolenylglycer-1-yl)methylenebis(phosphonate).

P$^1$-(2',3'-O-Isopropylideneinosin-5'-yl)-P$^2$-(2,3-di-O-linolenylglycer-1-yl)methylenebis(phosphonate).

P$^1$-(2',3'-O-Isopropylideneuridin-5'-yl)-P$^2$-(2,3-di-O-linolenylglycer-1-yl)methylenebis(phosphonate).

P$^1$-(2',3'-O-Isopropylidene-N$^4$-acetylcytidin-5'-yl)-P$^2$-(2,3-di-O-linolenylglycer-1-yl)methylenebis(phosphonate).

EXAMPLE 14

Preparation of N$^1$-(n-butan-4-yl)-2',3'-O-isopropylideneinosin-5'-yl cyclic P$^1$,P$^2$-methylenebis(phosphonate), an analogue of cyclic Inosin Diphosphate Ribose This Example illustrates an intramolecular nucleophilic reaction to form a cyclic derivative of biological importance.

A mixture of 2',3'-O-isopropylideneinosine (3.08 g, 10.0 mmol) and 4-bromobutyl acetate (3 ml) in dimethylformamide (75 ml) containing DBU (2.4 ml) is heated to 65° C. and then left at room temperature for 2 hours. The mixture is neutralized with concentrated hydrochloric acid and concentrated in vacuo. The residue is dissolved in chloroform, washed with water, dried over sodium sulfate and concentrated. The residue is chromatographed on a column of silica gel with CHCl$_3$, CHCl$_3$-EtOH (2%) to give a faster migrating, O-alkylated product (500 mg, 0.12%), $^1$H NMR (CDCl$_3$) δ 1.35 (s, 3H, iPr), 1.63 (s, 3H, iPr), 1.80–1.86 (m, 2H, H3"), 1.94–1.97 (m, 2H, H2"), 2.03 (s, 3H, Oac), 3.76 (dd, 1H, H5', J$_{4',5'}$=2.0 Hz, J$_{5',5"}$=13.0 Hz), 3.96 (dd, 1H, H5", J$_{4',5"}$=0.6 Hz), 4.12 (pseudo t, 2H, H4", J$_{3",4"}$=6.2 Hz), 4.52–4.53 (m, 1H, H4'), 4.63 (pseudo t, 2H, H1", J$_{1",2"}$=5.2 Hz), 5.10 (dd, 1H, H3', J$_{2',3'}$=5.9 Hz; J$_{3',4'}$=0.98 Hz), 5.18 (pseodo t, 1H, H2'), 5.88 (d, 1H, H1', J$_{1',2'}$=4.9 Hz), 7.95, 8.48 (two 1H singlets, H2, H8), and slower migrating N$^1$-alkylated product (3.37 g, 80%), $^1$H NMR (CDCl$_3$) δ 1.35 (s, 1H, iPr), 1.62 (s, 1H, iPr), 1.65–1.70 (m, 2H, H3"), 1.80–1.85 (m, 2H, H2"), 2.02 (s, 3H, OAc), 3.77 (d, 1H, H5', J$_{5',5"}$=12.6 Hz), 3.94 (dd, 1H, H5", J$_{4',5"}$=1.7 Hz), 4.07 (pseudo t, 4H, H1",4"), 4.49 (d, 1H H4'), 5.05–5.10 (m, 2H, H2',3'), 5.86 (d, 1H, H1', J$_{1',2'}$=4.2 Hz), 7.90, 7.99 (two 1H singlets, H2, H8). The N$^1$ alkylated product (422 mg, 1 mmol) is dissolved in pyridine (10 ml). Mesyl chloride (315 μl) is added and the mixture is kept at room temperature 20 minutes. Ethanol is added and the reaction mixture is concentrated in vacuo to give the desired mesylate in quantitative yield, $^1$H NMR (CDCl$_3$) δ 1.37 (s, 3H, iPr), 1.60 (s, 3H, iPr), 1.68–1.71 (m, 2H. H3"), 1.83–1.88 (m, 2H, H2"), 2.02 (s, 3H, Oac), 2.92 (s, 3H, Ms), 4.06–4.11 (m, 4H, H1", H4"), 4.39–4.41 (m, 2H, H5', H5"), 4.47–4.49 (m, 1H, H4'), 5.07 (DD, 1H, H3, J$_{2',3'}$=6.4 Hz, J$_{3',4'}$=3.5 Hz), 5.32 (dd, 1H, H2', J$_{1',2'}$=2.2 Hz), 6.07 (d, 1H, H1'), 7.86, 7.98 (two 1H singlets, H2, H8).

In a similar manner the O-alkylated derivative is mesylated to give the product. $^1$H NMR (CDCl$_3$) δ 1.38 (s, 3H, iPr), 1.61 (s, 3H, iPr), 1.84–1.86 (m, 2H, H3"), 1.94–1.99 (m, 2H, H2"), 2.03 (s, 3H, Oac), 2.89 (s, 3H, Ms), 4.12 (t, 2H, H4"), 4.39 (d, 1H, H5', J$_{5',5"}$=10.8 Hz), 4.47 (d, 1H, H5"), 4.48–4.50 (m, 1H, H4'), 4.61 (t, 2H, H1"), 5.15 (dd, 1H, H3', J$_{2',3'}$=6.4 Hz, J$_{3',4'}$=3.2 Hz), 5.43 (dd, 1H, H2', J$_{1',2'}$=2.2 Hz), 6.15 (d, 1H, H1'), 8.00, 8.51 (two 1H singlets, H2, H8).

The mesyl derivative of N$^1$ alkylated inosine (1 mmol) is treated with tetrabutylammonium salt of methylenebis (phosphonic) acid (1.3 mmol) in DMSO-d$_6$. The progress of the reaction is followed by $^{31}$P NMR. When the ratio of the singlet of the starting phosphonic acid to the two doublets of phosphonylmethylenephosphonic acid at 15.50 and 18.68 ppm (J$_{P,P}$=7.5 Hz) becomes constant, the reaction is completed and the product is purified by HPLC (retention time 40.7 min., 50.5% yield). $^1$H NMR (D$_2$O) δ 1.21 (t, 18H, Et$_3$N), 1.37 (s, 3H, iPr), 1.58 (s, 3H, iPr), 1.99 (s, 3H, OAc), 2.05 (t, 2H, P—CH$_2$—P, J$_{P,H}$=19.2 Hz), 3.11 (q, 12H, Et$_3$N), (4.02–4.06 (m, 6H, H1",H4', H5',5"), 4.55–4.57 (m, 1H, H4'), 5.16 (dd, 1H, H3', J$_{2',3'}$=6.1 Hz, J$_{3',4'}$=2.0 Hz), 5.32 (dd, 1H, H2', J$_{1',2'}$=3.1 Hz), 6.14 (d, 1H, H1'), 8.29, 8.36 (two 1H singlets, H2, H8).

This product is then heated with a mixture of Et3N-MeOH-water 3:3:1) for 30 minutes at 60° C. and then kept at room temperature for 3 days. The reaction mixture is concentrated in vacuo, and the product is purified by HPLC. The product (44 mg, 0.059 mmol) is then treated with DCC as described in Example 1. When $^{31}$P NMR of the reaction mixture shows the multisignal resonances chracteristic for BTAs formation, the mixture is heated at 60° C. for 2 hours. After addition of water the mixture is concentrated in vacuo and the residue was chromatographed on an HPLC column to give cyclic IMP-ribose analogue (6.1 mg, 9.5%, retention time 43.5 min.) as the triethylammonium salt. $^1$H NMR (D$_2$O) δ 1.20 (m, 18H, Et$_3$N), 1.45 (s, 3H, iPr), 1.48–1.60 (m, 2H, H2"), 1.55 (s, 3H, iPr), 3.05–3.2 (m, 12H, Et$_3$N), 3.38–3.55 (m, H4"), 3.85–3.95 (m, 3H, H1", H5'), 4,42–4.52 (m, 1H, H5"), 4.71–4.82 (m, 1H, H4'), 5.18 (d, 1H, H3', J$_{2',3'}$=5.8 Hz), 5.78 (d, 1H, H2'), 6.20 (s, 1H, H1'), 8.19, 8.38 (two 1H singlets, H2, H8), $^{31}$P NMR (D$_2$O) δ 16.84 (s), 18.08 (s).

In a similar manner the mesylate from O-alkylated inosine gives the corresponding phosphonylmethylenephosphonic acid (rt=46.1 minutes). $^1$H NMR (D$_2$O) δ 1.19 (t, 18H, Et$_3$N), 1.38 (s, 3H, iPr), 1.61 (s, 3H, iPr), 1.75–1.89 (m, 4H, H2", H3"), 1.97 (s, 3H, OAc), 2.03 (t, 2H, P—CH$_2$—P, J$_{P,H}$=19.9 Hz), 3.09 (q, 12H, Et$_3$N), 4.02–4.10 (m, 4H, H1", H4"), 4.41–4.46 (m, 2H, H5', H5"), 4.56–4,58 (m 1H, H4'), 5.16 (dd, 1H, H3', J$_{2',3'}$=6.0 Hz, J$_{3',4'}$=2.0 Hz), 5.33 (dd, 1H, H2', J$_{1',2'}$=3.2 Hz), 6.16 (d, 1H, H1'), 8.31, 8.51 (two 1H singlets, H2, H8). After deacetylation, further DCC treatment affords the corresponding cyclic diphosphonate (rt=49.9 minutes). $^1$H NMR (D$_2$O) δ 1.16–1.25 (m, 19H, Et$_3$N), 1.39 (s, 3H, iPr), 1.53–1.61 (m, 2H, H3"), 1.64 (s, 3H, iPr), 1.70–1.77 (m, 2H, H2"), 2.16 (P—CH$_2$—P, J$_{P,H}$=19.2 Hz)3.00–3.20 (q, 12H, Et$_3$N), 3.81–3.95 (m, 4H, H1", H4"), 4.04–4.25 (m, 3H, H4',H5', H5"), 5.14–5.24 (m, 2H, H2', H3'), 6.27 (d, 1H, H1', J$_{1',2'}$=3.4 Hz), 8.18, 8.65 (two 1H singlets, H2, H8). $^{31}$P NMR, 17.62 (d), 18.02 (d), J$_{P,P}$=10.3 Hz.

In a similar manner, the following nucleoside cyclic methylenebis(phosphonate)s are prepared:

$N^1$-(n-Butan-4-yl)-2',3'-O-isopropylideneadeosin-5'-yl cyclic $P^1,P^2$-methylenebis(phosphonate).

$N^1$-(n-Butan-4-yl)-2',3'-O-isopropylideneguanosin-5'-yl cyclic $P^1,P^2$-methylenebis(phosphonate).

$N^1$-(n-Butan-4-yl)-2',3'-O-isopropylideneuridin-5'-yl cyclic $P^1,P^2$-methylenebis(phosphonate)

$N^1$-(n-Butan-4-yl)-2',3'-O-isopropylidene-$N^4$-acetylcytidin-5'-yl cyclic $P^1,P^2$-methylenebis(phosphonate).

$N^1$-(2,3-Dihydroxy-4-hydroxymethylcyclopentan-6-yl)-2',3'-O-isopropylideneadeosin-5'-yl cyclic $P^1,P^2$-methylenebis(phosphonate).

$N^1$-(2,3-Dihydroxy-4-hydroxymethylcyclopentan-6-yl)-2',3'-O-isopropylideneguanosin-5'-yl cyclic $P^1,P^2$-methylenebis(phosphonate).

$N^1$-(2,3-Dihydroxy-4-hydroxymethylcyclopentan-6-yl)-2',3'-O-isopropylideneinosin-5'-yl cyclic $P^1,P^2$-methylenebis(phosphonate).

$N^1$-(2,3-Dihydroxy-4-hydroxymethylcyclopentan-6-yl)-2',3'-O-isopropylideneuridin-5'-yl cyclic $P^1,P^2$-methylenebis(phosphonate).

$N^1$-(2,3-Dihydroxy-4-hydroxymethylcyclopentan-6-yl)-2',3'-O-isopropylidene-$N^4$-acetylcytidin-5'-yl cyclic $P^1,P^2$-methylenebis(phosphonate).

$N^1$-(Ethoxymethan-2-yl)-2',3'-O-isopropylideneadeosin-5'-yl cyclic $P^1,P^2$-methylenebis(phosphonate).

$N^1$-(Ethoxymethan-2-yl)-2',3'-O-isopropylideneguanosin-5'-yl cyclic $P^1,P^2$-methylenebis(phosphonate).

$N^1$-(Ethoxymethan-2-yl)-2',3'-O-isopropylideneinosin-5'-yl cyclic $P^1,P^2$-methylenebis(phosphonate).

$N^1$-(Ethoxymethan-2-yl)-2',3'-O-isopropylideneuridin-5'-yl cyclic $P^1,P^2$-methylenebis(phosphonate).

$N^1$-(Ethoxymethan-2-yl)-2',3'-O-isopropylidene-$N^4$-acetylcytidin-5'-yl cyclic $P^1,P^2$-methylenebis(phosphonate).

EXAMPLE 15

Synthesis and use of $P^1$-(cytidin-5'-yl)-$P^2$-(trimethylammoniummethyl)methylenebis(phosphonate)

$P^1$-(cytidin-5'-yl)-$P^2$-(trimethylammoniumethyl) methylenebis(phosphonate) is an analog of cytidyl diphosphocholine (citicholine), an important intermediate in lipid metabolism and a drug under development for treatment for ischemic stroke. The analog may be prepared by the reaction of the appropriate BTA with a p-toluenosulfonate salt of choline. Thus, a mixture of the BTA prepared from $N^4$-acetylcytidin-5'-ylphosphonomethylenephosphonic acid (1 mmol in 10 ml of dry pyridine) and p-toluenosulfonate salt of choline (412 mg, 1.5 mmol) is kept at 55° C. for 4 hours. The mixture is processed as described in Example 3. $P^1$-($N^4$-acetyl-2',3'-O-isopropylidenecytidin-5'-yl)-$P^2$-(trimethylammoniumethyl)methylenebisphosphonate is obtained, and deprotected with Dowex 50WX8/$H^+$ to give the desired compound.

The compound may be administered to patients suffering from ischemic stroke, preferably as soon as possible following onset of symptoms. The optimal dosage regimen for a particular patient or situation can be readily determined by one of ordinary skill, but in general, administration of between approximately 500 to 2000 milligrams daily for approximately six weeks will be appropriate.

EXAMPLE 16

$P^1$-(2',3'-O-isopropylideneadenosin-5'-yl)-$P^2$-[mycophenol-6-(3'-methylhex-2'-ene-6'-yl) methylenebis(phosphonate) (compound 7, Scheme 3, n=3)

To a solution of compound 3 in Scheme 3 (140 mg, 0.2 mmol) in pyridine (0.8 mL) is added DIC (156 mL, 1 mmol) and the mixture is left (approximately for 6 hours) at room temperature until intermediate 5 is formed (multisignal resonances in $^{31}$P NMR; Pankiewicz, et al. 1997). MPol (n=3) (75 mg, 0.25 mmol) is then added and the reaction mixture is heated at 55–60° C. for 24 hours when the $^{31}$P NMR spectrum of the reaction mixture exhibits two broad signals at 8 ppm and 25 ppm characteristic for the presence of intermediate 6. Then a mixture of water (200 gL) and $Et_3N$ (100 gL) is added, and the reaction mixture kept at 80–85° C. for 30 hours. HPLC purification on a Dynamax-300A C18-83-243-C column with a flow rate of 20 mL/min of 0.05 M $Et_3N$ $H_2CO_3$ (TEAB) followed by a linear gradient of 0.05 M TEAB-aq.MeCN (70%) affords compound 7 (62 mg, 32%) as the triethylammonium salt. $^1$H NMR: ($D_2O$) d 1.24 (t, 18 H, $Et_3N$), 1.37 and 1.61 (s, 3H each, isopropylidene), 1.63 [m, 2H, $CH_2$5' (MPAlc)], 1.67 (s, 3H, $CH_3$), 1.93 (s, 3H, $CH_3$), 1.95 [m, 2H, $CH_2$4' (MPAlc)], 2.07 (t, 2H, P—$CH_2$—P, J=19.9 Hz), 3.09 [d, 1H, $CH_2$1' (MPAlc)], 3.16 (q, 12H, $Et_3N$), 3.60 (s, 3H, $OCH_3$), 3.79 [q, 2H, 6° $CH_2$ (MPAlc), $J_{H-P}$=6.3 Hz, $J_{H-H}$=6.3 Hz)], 4.05 [m, 2H, H5',5" (Ado)], 4.52 [m, 1H, H4' (Ado)], 4.94, [dd, 1H, CH1' (MPAlc), J=6.0 Hz, J=6.5 Hz], 5.13 (s, 2H, $CH_2$3 (MPAlc)], 5.15 [dd, 1H, H3' (Ado), $J_{3',4'}$=1.7 Hz, $J_{2',3'}$=6.0 Hz], 5.20 [dd, 1H, H2' (Ado), $J_{1',2'}$=3.0 Hz], 6.00 [d, 1H, H1' (Ado)], 8.03 and 8.29 [two 1H singlets, H2, H8 (Ado)]; $^{31}$P NMR ($D_2O$) AB system 17.70 and 18.02 (J=11.4 Hz).

By following the same procedure but using the corresponding mycophenolic alcohol and protected nucleosides, the following compounds are also prepared:

$P^1$-(2',3'-O-isopropylideneadenosin-5'-yl)-$P^2$-[7-hydroxy-5-methoxy-4-methyl-phthalan-1-on-6-yl-(3'-methylbut-2'-ene-4'-yl)]methylenebis(phosphonate), $P^1$-(2',3'-O-isopropylideneadenosin-5'-yl)-$P^2$-[7-hydroxy-5-methoxy-4-methyl-phthalan-1-on-6-yl-(3'-methylpent-2'-ene-5'-yl)]methylenebis(phosphonate), $P^1$-(2',3'-O-isopropylideneadenosin-5'-yl)-$P^2$-[7-hydroxy-5-methoxy-4-methyl-phthalan-1-on-6-yl-(3'-methylhept-2'-ene-7'-yl)]methylenebis(phosphonate), $P^1$-(2',3'-O-isopropylideneadenosin-5'-yl)-$P^2$-[7-hydroxy-5-methoxy-4-methyl-phthalan-1-on-6-yl-(3'-methylocta-2'-ene-8'-yl)]methylenebis(phosphonate), $P^1$-(3'-O-acetyl-2'-fluoro-2'-deoxyadenosin-5'-yl)-$P^2$-[7-hydroxy-5-methoxy-4-methyl-phthalan-1-on-6-yl-(3'-methylbut-2'-ene-4'-yl)]methylenebis(phosphonate), $P^1$-(3'-O-acetyl-2'-fluoro-2'-deoxyadenosin-5'-yl)-$P^2$-[7-hydroxy-5-methoxy-4-methyl-phthalan-1-on-6-yl-(3'-methylpent-2'-ene-5'-yl)]methylenebis(phosphonate), $P^1$-(3'-O-acetyl-2'-fluoro-2'-deoxyadenosin-5'-yl)-$P^2$-[7-hydroxy-5-methoxy-4-methyl-phthalan-1-on-6-yl-(3'-methylhex-2'-ene-6'-yl)]methylenebis(phosphonate), $P^1$-(3'-O-acetyl-2'-fluoro-2'-deoxyadenosin-5'-yl)-$P^2$-(7-hydroxy-5-methoxy-4-methyl-phthalan-1-on-6-yl-(3'-methylhept-2'-ene-7'-yl)]methylenebis(phosphonate), $P^1$-(3'-O-acetyl-2'-fluoro-2'-deoxyadenosin-5'-yl)-$P^2$-[7-hydroxy-5-methoxy-4-methyl-phthalan-1-on-6-yl-(3'-methyloct-2'-ene-8'-yl)]methylenebis(phosphonate), P$^1$-(2'-O-acetyl-3'-fluoro-3'-deoxyadenosin-5'-yl)-P$^2$-[7-hydroxy-5-methoxy-4-methyl-phthalan-1-on-6-yl-(3'-methylbut-2'-ene-4'-yl)]methylenebis(phosphonate), P$^1$-(2'-O-acetyl-3'-fluoro-3'-deoxyadenosin-5'-yl)-P$^2$-[7-hydroxy-5-methoxy-4-methyl-phthalan-1-on-6-yl-(3'-methylpent-2'-ene-5'-yl)]methylenebis(phosphonate), P$^1$-(2'-O-acetyl-3'-fluoro-3'-deoxyadenosin-5'-yl)-P$^2$-[7-hydroxy-5-methoxy-4-methyl-phthalan-1-on-6-yl-(3'-methylhex-2'-ene-6'-yl)]methylenebis(phosphonate), P$^1$-(2'-O-acetyl-3'-fluoro-3'-deoxyadenosin-5'-yl)-P$^2$-(7-hydroxy-5-methoxy-4-methyl-phthalan-1-on-6-yl-(3'-methylhept-2'-ene-7'-yl)]methylenebis(phosphonate), P$^1$-(2'-O-acetyl-3'-fluoro-3'-deoxyadenosin-5'-yl)-P$^2$-[7-hydroxy-5-methoxy-4-methyl-phthalan-1-on-6-yl-(3'-methyloct-2'-ene-8'-yl)]methylenebis(phosphonate), P$^1$-[9-(3'-O-acetyl-2'-fluoro-2'-deoxy-β-D-arabinofuranosyl)adenin-5'-yl]-P$^2$-[7-hydroxy-5-methoxy-4-methyl-phthalan-1-on-6-yl-(3'-methylbut-2'-ene-4'-yl)]methylenebis(phosphonate), P$^1$-[9-(3'-O-acetyl-2'-fluoro-2'-deoxy-β-D-arabinofuranosyl)adenin-5'-yl]-P$^2$-[7-hydroxy-5-methoxy-4-methyl-phthalan-1-on-6-yl-(3'-methylpent-2-ene-5'-yl)]methylenebis(phosphonate), P$^1$-[9-(3'-O-acetyl-2'-fluoro-2'-deoxy-β-D-arabinofuranosyl)adenin-5'-yl]-P$^2$-[7-hydroxy-5-methoxy-4-methyl-phthalan-1-on-6-yl-(3'-methylhex-2'-ene-6'-yl)]methylenebis(phosphonate), P$^1$-[9-(3'-O-acetyl-2'-fluoro-2'-deoxy-β-D-arabinofuranosyl)adenin-5'-yl]-P$^2$-[7-hydroxy-5-methoxy-4-methyl-phthalan-1-on-6-yl-(3'-methylhept-2-ene-7'-yl)]methylenebis(phosphonate), P$^1$-[9-(3'-O-acetyl-2'-fluoro-2'-deoxy-β-D-arabinofuranosyl) adenin-5'-yl]-P$^2$-[7-hydroxy-5-methoxy-4-methyl-phthalan-1-on-6-yl-(3'-methyloct-ene- 8'-yl)]methylenebis(phosphonate), P$^1$-[9-(2'-O-acetyl-3'-fluoro-3'-deoxy-β-D-arabinofuranosyl)adenin-5'-yl]-P$^2$-[7-hydroxy-5-methoxy-4-methyl-phthalan-1-on-6-yl-(3'-methylbut-2-ene-4'-yl)]methylenebis(phosphonate), P$^1$-[9-(2'-O-acetyl-3'-fluoro-3'-deoxy-β-D-arabinofuranosyl)adenin-5'-yl]-P$^2$-[7-hydroxy-5-methoxy-4-methyl-phthalan-1-on-6-yl-(3'-methylpent-2-ene-5'-yl)]methylenebis(phosphonate), P$^1$-[9-(2'-O-acetyl-3'-fluoro-3'-deoxy-β-D-arabinofuranosyl) adenin-5'-yl]-P$^2$-[7-hydroxy-5-methoxy-4-methyl-phthalan-1-on-6-yl-(3'-methylhex-2'-ene-6'-yl)]methylenebis(phosphonate), P$^1$-[9-(2'-O-acetyl-3'-fluoro-3'-deoxy-β-D-arabinofuranosyl)adenin-5'-yl]-P$^2$-[7-hydroxy-5-methoxy-4-methyl-phthalan-1-on-6-yl-(3'-methylhept-2'-ene-7'-yl)]methylenebis(phosphonate), P$^1$-[9-(2'-O-acetyl-3'-fluoro-3'-deoxy-β-D-arabinofuranosyl)adenin-5'-yl]-P$^2$-[7-hydroxy-5-methoxy-4-methyl-phthalan-1-on-6-yl-(3'-methyloct-2'-ene-8'-yl)]methylenebis(phosphonate), P$^1$-(2',3'-O-isopropylideneguanosin-5'-yl)-P$^2$-[7-hydroxy-5-methoxy-4-methyl-phthalan-1-on-6-yl-(3'-methylbut-2'-ene-4'-yl)]methylenebis(phosphonate), P$^1$-(2',3'-O-isopropylideneguanosin-5'-yl)-P$^2$-[7-hydroxy-5-methoxy-4-methyl-phthalan-1-on-6-yl-(3'-methylpent-2'-ene-5'-yl)]methylenebis(phosphonate), P$^1$-(2',3'-O-isopropylideneguanosin-5'-yl)-P$^2$-[7-hydroxy-5-methoxy-4-methyl-phthalan-1-on-6-yl-(3'-methylhex-2'-ene-6'-yl)]methylenebis(phosphonate), P$^1$-(2',3'-O-isopropylideneguanosin-5'-yl)-P$^2$-[7-hydroxy-5-methoxy-4-methyl-phthalan-1-on-6-yl-(3'-methylhept-2'-ene-7'-yl)]methylenebis(phosphonate), P$^1$-(2',3'-O-isopropylideneguanosin-5'-yl)-P$^2$-[7-hydroxy-5-methoxy-4-methyl-phthalan-1-on-6-yl-(3'-methyloct-2'-ene-8'-yl)]methylenebis(phosphonate), P$^1$-(3'-O-acetyl-2'-fluoro-2'-deoxyguanosin-5'-yl)-P$^2$-[7-hydroxy-5-methoxy-4-methyl-phthalan-1-on-6-yl-(3'-methylbut-2'-ene-4'-yl)]methylenebis(phosphonate), P$^1$-(3'-O-acetyl-2'-fluoro-2'-deoxyguanosin-5'-yl)-P$^2$-[7-hydroxy-5-methoxy-4-methyl-phthalan-1-on-6-yl-(3'-methylpent-2'-ene-5'-yl)]methylenebis(phosphonate), P$^1$-(3'-O-acetyl-2'-fluoro-2'-deoxyguanosin-5'-yl)-P$^2$-[7-hydroxy-5-methoxy-4-methyl-phthalan-1-on-6-yl-(3'-methylhex-2'-ene-6'-yl)]methylenebis(phosphonate), P$^1$-(3'-O-acetyl-2'-fluoro-2'-deoxyguanosin-5'-yl)-P$^2$-[7-hydroxy-5-methoxy-4-methyl-phthalan-1-on-6-yl-(3'-methylhept-2'-ene-7'-yl)]methylenebis(phosphonate), P$^1$-(3'-O-acetyl-2'-fluoro-2'-deoxyguanosin-5'-yl)-P$^2$-[7-hydroxy-5-methoxy-4-methyl-phthalan-1-on-6-yl-(3'-methyloct-2'-ene-8'-yl)]methylenebis(phosphonate), P$^1$-(2'-O-acetyl-3'-fluoro-3'-deoxyguanosin-5'-yl)-P$^2$-[7-hydroxy-5-methoxy-4-methyl-phthalan-1-on-6-yl-(3'-methylbut-2'-ene-4'-yl)]methylenebis(phosphonate), P$^1$-(2'-O-acetyl-3'-fluoro-3'-deoxyguanosin-5'-yl)-P$^2$-[7-hydroxy-5-methoxy-4-methyl-phthalan-1-on-6-yl-(3'-methylpent-2'-ene-5'-yl)]methylenebis(phosphonate), P$^1$-(2'-O-acetyl-3'-fluoro-3'-deoxyguanosin-5'-yl)-P$^2$-[7-hydroxy-5-methoxy-4-methyl-phthalan-1-on-6-yl-(3'-methylhex-2'-ene-6'-yl)]methylenebis(phosphonate), P$^1$-(2'-O-acetyl-3'-fluoro-3'-deoxyguanosin-5'-yl)-P$^2$-[7-hydroxy-5-methoxy-4-methyl-phthalan-1-on-6-yl-(3'-methylhept-2'-ene-7'-yl)]methylenebis(phosphonate), P$^1$-(2'-O-acetyl-3'-fluoro-3'-deoxyguanosin-5'-yl)-P$^2$-[7-hydroxy-5-methoxy-4-methyl-phthalan-1-on-6-yl-(3'-lmethyloct-2'-ene-8'-yl)]methylenebis(phosphonate), P$^1$-[9-(3'-O-acetyl-2'-fluoro-2'-deoxy-β-D-arabinofuranosyl)guanin-5'-yl]-P$^2$-[7-hydroxy-5-methoxy-4-methyl-phthalan-1-on-6-yl-(3'-methylbut-2'-ene- 4'-yl)]methylenebis(phosphonate), P$^1$-[9-(3'-O-acetyl-2'-fluoro-2'-deoxy-β-D-arabinofuranosyl)guanin-5'-yl]-P$^2$-[7-hydroxy-5-methoxy-4-methyl-phthalan-1-on-6-yl-(3'-methylpent-2'-ene-5'-yl)]methylenebis(phosphonate), P$^1$-[9-(3'-O-acetyl-2'-fluoro-2'-deoxy-β-D-arabinofuranosyl)guanin-5'-yl]-P$^2$-[7-hydroxy-5-methoxy-4-methyl-phthalan-1-on-6-yl-(3'-methylhex-2'-ene-6'-yl)]methylenebis(phosphonate), P$^1$-[9-(3'-O-acetyl-2'-fluoro-2'-deoxy-β-D-arabinofuranosyl)guanin-5'-yl]-P$^2$-[7-hydroxy-5-methoxy-4-methyl-phthalan-1-on-6-yl-(3'-methylhept-2'-ene-7'-yl)]methylenebis(phosphonate), P$^1$-[9-(3'-O-acetyl-2'-fluoro-2'-deoxy-β-D-arabinofuranosyl) guanin-5'-yl]-P$^2$-[7-hydroxy-5-methoxy-4-methyl-phthalan-1-on-6-yl-(3'-methyloct-2'-ene-8'-yl)]methylenebis(phosphonate), P$^1$-[9-(2'-O-acetyl-3'-fluoro-3'-deoxy-β-D-arabinofuranosyl)guanin-5'-yl]-P$^2$-[7-hydroxy-5-methoxy-4-methyl-phthalan-1-on-6-yl-(3'-methylbut-2'-ene-4'-yl)]methylenebis(phosphonate), P$^1$-[9-(2'-O-acetyl-3'-fluoro-3'-deoxy-β-D-arabinofuranosyl)guanin-5'-yl]-P$^2$-[7-hydroxy-5-methoxy-4-methyl-phthalan-1-on-6-yl-(3'-methylpent-2'-ene-5'-yl)]methylenebis(phosphonate), P$^1$-[9-(2'-O-acetyl-3'-fluoro-3'-deoxy-β-D-arabinofuranosyl)guanin-5'-yl]-P$^2$-[7-hydroxy-5-methoxy-4-methyl-phthalan-1-on-6-yl-(3'-methylhex-2'-ene-6'-yl)]methylenebis(phosphonate), P$^1$-[9-(2'-O-acetyl-3'-fluoro-3'-deoxy-β-D-arabinofuranosyl)guanin-5'-yl]-P$^2$-[7-hydroxy-5-methoxy-4-methyl-phthalan-1-on-6-yl-(3'-methylhept-2'-ene-7'-yl)]methylenebis(phosphonate), P$^1$-[9-(2'-O-acetyl-3'-fluoro-3 '-deoxy-β-D-arabinofuranosyl)guanin-5'-yl]-P$^2$-[7-hydroxy-5-methoxy-4-methyl-phthalan-1-on-6-yl-(3'-methyloct-2'-ene-8'-yl)]methylenebis(phosphonate), P$^1$-(2',3'-O-isopropylideneinosin-5'-yl)-P$^2$-[7-hydroxy-5-methoxy-4-methyl-phthalan-1-on-6-yl-(3'-methylbut-2'-ene-4'-yl)]methylenebis(phosphonate), P$^1$-(2',3'-O-isopropylideneinosin-5'-yl)-P$^2$-[7-hydroxy-5-methoxy-4-methyl-phthalan-1-on-6-yl-(3'-methylpent-2'-ene-5'-yl)]methylenebis(phosphonate), P$^1$-(2',3'-O-isopropylideneinosin-5'-yl)-P$^2$-[7-hydroxy-5-methoxy-4-methyl-phthalan-1-on-6-yl-(3'-methylhex-2'-ene-6'-yl)]methylenebis(phosphonate), P$^1$-(2',3'-O-isopropylideneinosin-5'-yl)-P$^2$-[7-hydroxy-5-methoxy-4-methyl-phthalan-1-on-6-yl-(3'-methylhept-2'-ene-7'-yl)]methylenebis(phosphonate), P$^1$-(2',3'-O-isopropylideneinosin-5'-yl)-P$^2$-[7-hydroxy-5-methoxy-4-methyl-phthalan-1-on-6-yl-(3'-methyloct-2'-ene-8'-yl)]methylenebis(phosphonate), P$^1$-(3'-O-acetyl-2'-fluoro-2'-deoxyinosin-5'-yl)-P$^2$-[7-hydroxy-5-methoxy-4-methyl-phthalan-1-on-6-yl-(3'-methylbut-2'-ene-4'-yl)]methylenebis(phosphonate), P$^1$-(3'-O-acetyl-2'-fluoro-2'-deoxyinosin-5'-yl)-P$^2$-[7-hydroxy-5-methoxy-4-methyl-phthalan-1-on-6-yl-(3'-methylpent-2'-ene-5'-yl)]methylenebis(phosphonate), P$^1$-(3'-O-acetyl-2'-fluoro-2'-deoxyinosin-5'-yl)-P$^2$-[7-hydroxy-5-methoxy-4-methyl-phthalan-1-on-6-yl-(3'-methylhex-2'-ene-6'-yl)]methylenebis(phosphonate), P$^1$-(3'-O-acetyl-2'-fluoro-2'-deoxyinosin-5'-yl)-P$^2$-[7-hydroxy-5-methoxy-4-methyl-phthalan-1-on-6-yl-(3'-methylhept-2'-ene-7'-yl)]methylenebis(phosphonate), P$^1$-(3'-O-acetyl-2'-fluoro-2'-deoxyinosin-5'-yl)-P$^2$-[7-hydroxy-5-methoxy-4-methyl-phthalan-1-on-6-yl-(3'-methyloct-2'-ene-8'-yl)]methylenebis(phosphonate), P$^1$-(2'-O-acetyl-3'-fluoro-3'-deoxyinosin-5'-yl)-P$^2$-[7-hydroxy-5-methoxy-4-methyl-phthalan-1-on-6-yl-(3'-methylbut-2'-ene-4'-yl)]methylenebis(phosphonate), P$^1$-(2'-O-acetyl-3'-fluoro-3'-deoxyinosin-5'-yl)-P$^2$-[7-hydroxy-5-methoxy-4-methyl-phthalan-1-on-6-yl-(3'-methylpent-2'-ene-5'-yl)]methylenebis(phosphonate), P$^1$-(2'-O-acetyl-3'-fluoro-3'-deoxyinosin-5'-yl)-P$^2$-[7-hydroxy-5-methoxy-4-methyl-phthalan-1-on-6-yl-(3'-methylhex-2'-ene-6'-yl)]methylenebis(phosphonate), P$^1$-(2'-O-acetyl-3'-fluoro-3'-deoxyinosin-5'-yl)-P$^2$-[7-hydroxy-5-methoxy-4-methyl-phthalan-1-on-6-yl-(3'-methylhept-2'-ene-7'-yl)]methylenebis(phosphonate), P$^1$-(2'-O-acetyl-3'-fluoro-3'-deoxyinosin-5'-yl)-P$^2$-[7-hydroxy-5-methoxy-4-methyl-phthalan-1-on-6-yl-(3'-methyloct-2'-ene-8'-yl)]methylenebis(phosphonate), P$^1$-[9-(3'-O-acetyl-2'-fluoro-2'-deoxy-β-D-arabinofuranosyl)hypoxanthin-5'-yl]-P$^2$-[7-hydroxy-5-methoxy-4-methyl-phthalan-1-on-6-yl-(3'-methylbut-2'-ene-4'-yl)]methylenebis(phosphonate), P$^1$-[9-(3'-O-acetyl-2'-fluoro-2'-deoxy-β-D-arabinofuranosyl)hypoxanthin-5'-yl]-P$^2$-[7-hydroxy-5-methoxy-4-methyl-phthalan-1-on-6-yl-(3'-methylpent-2'-ene-5'-yl)]methylenebis(phosphonate), P$^1$-[9-(3'-O-acetyl-2'-fluoro-2'-deoxy-β-D-arabinofuranosyl)hypoxanthin-5'-yl]-P$^2$-[7-hydroxy-5-methoxy-4-methyl-phthalan-1-on-6-yl-(3'-methylhex-2'-ene-6'-yl)]methylenebis(phosphonate), P$^1$-[9-(3'-O-acetyl-2'-fluoro-2'-deoxy-β-D-arabinofuranosyl)hypoxanthin-5'-yl]-P$^2$-[7-hydroxy-5-methoxy-4-methyl-phthalan-1-on-6-yl-(3'-methylhept-2'-ene-7'-yl)]methylenebis(phosphonate), P$^1$-[9-(3'-O-acetyl-2'-fluoro-2'-deoxy-β-D-arabinofuranosyl)hypoxanthin-5'-yl]-P$^2$-[7-hydroxy-5-methoxy-4-methyl-phthalan-1-on-6-yl-(3'-methyloct-2'-ene-8'-yl)]methylenebis(phosphonate), P$^1$-[9-(2'-O-acetyl-3'-fluoro-3 '-deoxy-β-D-arabinofuranosyl)hypoxanthin-5'-yl]-P$^2$-[7-hydroxy-5-methoxy-4-methyl-phthalan-1-on-6-yl-(3'-methylbut-2'-ene-4'-yl)]methylenebis(phosphonate), P$^1$-[9-(2'-O-acetyl-3'-fluoro-3'-deoxy-β-D-arabinofuranosyl)hypoxanthin-5'-yl]-P$^2$-[7-hydroxy-5-methoxy-4-methyl-phthalan-1-on-6-yl-(3'-methylpent-2'-ene-5'-yl)]methylenebis(phosphonate), P$^1$-[9-(2'-O-acetyl-3'-fluoro-3'-deoxy-β-D-arabinofuranosyl)hypoxanthin-5'-yl]-P$^2$-[7-hydroxy-5-methoxy-4-methyl-phthalan-1-on-6-yl-(3'-methylhex-2'-ene-6'-yl)]methylenebis(phosphonate), P$^1$-[9-(2'-O-acetyl-3'-fluoro-3'-deoxy-β-D-arabinofuranosyl)hypoxanthin-5'-yl]-P$^2$-[7-hydroxy-5-methoxy-4-methyl-phthalan-1-on-6-yl-(3'-methylhept-2'-ene-7'-yl)]methylenebis(phosphonate), and P$^1$-[9-(2'-O-acetyl-3'-fluoro-3'-deoxy-β-D-arabinofuranosyl)hypoxanthin-5'-yl]-P$^2$-[7-hydroxy-5-methoxy-4-methyl-phthalan-1-on-6-yl-(3'-methyloct-2'-ene-8'-yl)]methylenebis(phosphonate).

EXAMPLE 17

P$^1$-(adenosin-5'-yl)-P$^2$-(mycophenol-5'-yl) methylenebis(phosphonate) (compound 1, Scheme 3, n=3)

Compound 7 of Scheme 3 (24 mg, 0.025 mmol, as triethylammonium salt) is dissolved in a mixture of methanol (1 mL) and water (1 mL) containing CF$_3$COOH (0.5 mL). The mixture is kept at room temperature for 1 hour and heated at 50° C. for 30 minutes. Methanol is removed in vacuo, the mixture is diluted with water (2 mL), neutralized with concentrated ammonia and then the solvents are removed in vacuo. The residue is chromatographed on a HPLC Dynamax-300A C18-83-243-C column with a flow rate of 20 mL/min of 0.05 M Et$_3$N H$_2$CO$_3$ (TEAB) followed by a linear gradient of 0.05 M TEAB-aq.MeCN (70%) to give 1 as the triethylammonium salt. This compound was converted to the sodium salt of 1 (11 mg, 63%) by passing through a column of Dowex 50WX8/Na$^+$form. $^1$H NMR (D$_2$O) d 1.64 [m, 2H, CH$_2$5' (MPAlc)], 1.73 (s, 3H, CH$_3$), 2.01 [m, 2H, CH$_2$4' (MPAlc)], 2.07 (s, 3H, CH$_3$), 2.18 (t, 2H, P—CH$_2$—P, J=20.0 Hz), 3.21 [d, 2H, CH$_2$1' (MPAlc), J=6.9 Hz], 3.68 (s, 3H, OCH$_3$), 3.85 [q, 2H, CH$_2$6' (MPAlc), J=6.3 Hz], 4.19 [m, 2H, H5',5" (Ado)], 4.33 [m, 1H, H4'(Ado)], 4.51 [dd, 1H, H3' (Ado), J$_{3',4'}$=4.2 Hz, J$_{2',3'}$=5.1 Hz], 4.67 [dd, 1H, H2' (Ado), J$_{1',2'}$=5.2 Hz], 4.93 [m, 1H, CH2' (MPAlc)], 5.26 [s, 2H, CH$_2$3 (MPAlc)], 5.99 [d, 1H, H1' (Ado)], 8.13 and 8.49 (two 1H singlets, H2 and H8); $^{31}$P NMR (D$_2$O) AB system 17.65, 18.35 (J=11.5 Hz).

By following the same procedure but using the corresponding protected P$^1$,P$^2$-disubstituted methylenebis (phosphonate), the following compounds are also prepared:

P$^1$-(adenosin-5'-yl)-P$^2$-[7-hydroxy-5-methoxy-4-methyl-phthalan-1-on-6-yl-(3'-methylbut-2'-ene-4'-yl)]methylenebis(phosphonate), P$^1$-(adenosin-5'-yl)-P$^2$-[7-hydroxy-5-methoxy-4-methyl-phthalan-1-on-6-yl-(3'-methylpent-2'-ene-5'-yl)]methylenebis(phosphonate), P$^1$-(adenosin-5'-yl)-P$^2$-[7-hydroxy-5-methoxy-4-methyl-phthalan-1-on-6-yl-(3'-methylhept-2'-ene-7'-yl)]methylenebis(phosphonate), P$^1$-(adenosin-5'-yl)-P$^2$-[7-hydroxy-5-methoxy-4-methyl-phthalan-1-on-6-yl-(3'-methyloct-2-ene-8'-yl)]methylenebis(phosphonate), P$^1$-(2'-fluoro-2'-deoxyadenosin-5'-yl)-P$^2$-[7-hydroxy-5-methoxy-4-methyl-phthalan-1-on-6-yl-(3'-methylbut-2'-ene-4'-yl)]-methylenebis(phosphonate), P$^1$-(2'-fluoro-2'-deoxyadenosin-5'-yl)-P$^2$-[7-hydroxy-5-methoxy-4-methyl-phthalan-1-on-6-yl-(3'-methylpent-2'-ene-5'-yl)]-methylenebis(phosphonate), P$^1$-(2'-fluoro-2'-deoxyadenosin-5'-yl)-P$^2$-[7-hydroxy-5-methoxy-4-methyl-phthalan-1-on-6-yl-(3'-methylhex-2-ene-6'-yl)]-methylenebis(phosphonate), P$^1$-(2'-fluoro-2'-deoxyadenosin-5'-yl)-P$^2$-[7-hydroxy-5-methoxy-4-methyl-phthalan-1-on-6-yl-(3'-methylhept-2'-ene-7'-yl)]-methylenebis(phosphonate), P$^1$-(2'-fluoro-2'-deoxyadenosin-5'-yl)-P$^2$-[7-hydroxy-5-methoxy-4-methyl-phthalan-1-on-6-yl-(3'-methyloct-2'-ene-8'-yl)]-methylenebis(phosphonate), P$^1$-(3'-fluoro-3'-deoxyadenosin-5'-yl)-P$^2$-[7-hydroxy-5-methoxy-4-methyl-phthalan-1-on-6-yl-(3'-methylbut-2'-ene-4'-yl)]-methylenebis(phosphonate), P$^1$-(3'-fluoro-3'-deoxyadenosin-5'-yl)-P$^2$-[7-hydroxy-5-methoxy-4-methyl-phthalan-1-on-6-yl-(3'-methylpent-2'-ene-5'-yl)]-methylenebis(phosphonate), P$^1$-(3'-fluoro-3'-deoxyadenosin-5'-yl)-P$^2$-[7-hydroxy-5-methoxy-4-methyl-phthalan-1-on-6-yl-(3'-methylhex-2'-ene-6'-yl)]-methylenebis(phosphonate), P$^1$-(3'-fluoro-3'-deoxyadenosin-5'-yl)-P$^2$-[7-hydroxy-5-methoxy-4-methyl-phthalan-1-on-6-yl-(3'-methylhept-2'-ene-7'-yl)]-methylenebis(phosphonate), P$^1$-(3'-fluoro-3'-deoxyadenosin-5'-yl]-P$^2$-[7-hydroxy-5-methoxy-4-methyl-phthalan-1-on-6-yl-(3'-methyloct-2'-ene-8'-yl)]-methylenebis(phosphonate), P$^1$-[9-(2'-fluoro-2'-deoxy-β-D-arabinofuranosyl)adenin-5'-yl]-P$^2$-[7-hydroxy-5-methoxy-4-methyl-phthalan-1-on-6-yl-(3'-methylbut-2'-ene-4'-yl)]methylenebis(phosphonate), P$^1$-[9-(2'-fluoro-2'-deoxy-β-D-arabinofuranosyl)adenin-5'-yl]-P$^2$-[7-hydroxy-5-methoxy-4-methyl-phthalan-1-on-6-yl-(3'-methylpent-2'-ene-5'-yl)]methylenebis(phosphonate), P$^1$-[9-(2'-fluoro-2'-deoxy-β-D-arabinofuranosyl)adenin-5'-yl]-P$^2$-[7-hydroxy-5-methoxy-4-methyl-phthalan-1-on-6-yl-(3'-methylhex-2'-ene-6'-yl)]methylenebis(phosphonate), P$^1$-[9-(2'-fluoro-2'-deoxy-β-D-arabinofuranosyl)adenin-5'-yl]-P$^2$-[7-hydroxy-5-methoxy-4-methyl-phthalan-1-on-6-yl-(3'-methylhept-2'-ene-7'-yl)]methylenebis(phosphonate), P$^1$-[9-(2'-fluoro-2'-deoxy-β-D-arabinofuranosyl)adenin-5'-yl]-P$^2$-[7-hydroxy-5-methoxy-4-methyl-phthalan-1-on-6-yl-(3'-methyloct-2'-ene-8'-yl)]methylenebis(phosphonate), P$^1$-[9-(3'-fluoro-3'-deoxy-β-D-arabinofuranosyl)adenin-5'-yl]-P$^2$-[7-hydroxy-5-methoxy-4-methyl-phthalan-1-on-6-yl-(3'-methylbut-2'-ene-4'-yl)]methylenebis(phosphonate), P$^1$-[9-(3'-fluoro-3'-deoxy-β-D-arabinofuranosyl)adenin-5'-yl]-P$^2$-[7-hydroxy-5-methoxy-4-methyl-phthalan-1-on-6-yl-(3'-methylpent-2'-ene-5'-yl)]methylenebis(phosphonate), P$^1$[9-(3'-fluoro-3'-deoxy-β-D-arabinofuranosyl)adenin-5'-yl]-P$^2$-[7-hydroxy-5-methoxy-4-methyl-phthalan-1-on-6-yl-(3'-methylhex-2'-ene-6'-yl)]methylenebis(phosphonate), P$^1$-[9-(3'-fluoro-3'-deoxy-β-D-arabinofuranosyl)adenin-5'-yl]-P$^2$-[7-hydroxy-5-methoxy-4-methyl-phthalan-1-on-6-yl-(3'-methylhept-2'-ene-7'-yl)]methylenebis(phosphonate), P$^1$-[9-(3'-fluoro-3'-deoxy-β-D-arabinofuranosyl)adenin-5'-yl]-P$^2$-[7-hydroxy-5-methoxy-4-methyl-phthalan-1-on-6-yl-(3'-methyloct-2'-ene-8'-yl)]methylenebis(phosphonate), P$^1$-(guanosin-5'-yl)-P$^2$-[7-hydroxy-5-methoxy-4-methyl-phthalan-1-on-6-yl-(3'-methylbut-2'-ene-4'-yl)]methylenebis(phosphonate), P$^1$-(guanosin-5'-yl)-P$^2$-[7-hydroxy-5-methoxy-4-methyl-phthalan-1-on-6-yl-(3'-methylpent-2'-ene-5'-yl)]methylenebis(phosphonate), P$^1$-(guanosin-5'-yl)-P$^2$-[7-hydroxy-5-methoxy-4-methyl-phthalan-1-on-6-yl-(3'-methylhex-2'-ene-6'-yl)]methylenebis(phosphonate), P$^1$-(guanosin-5'-yl)-P$^2$-[7-hydroxy-5-methoxy-4-methyl-phthalan-1-on-6-yl-(3'-methylhept-2'-ene-7'-yl)]methylenebis(phosphonate), P$^1$-(guanosin-5'-yl)-P$^2$-[7-hydroxy-5-methoxy- 4-methyl-phthalan-1-on-6-yl-(3'-methyloct-2-ene-8'-yl)]methylenebis(phosphonate), P$^1$-(2'-fluoro-2'-deoxyguanosin-5'-yl)-P$^2$-[7-hydroxy-5-methoxy-4-methyl-phthalan-1-on-6-yl-(3'-methylbut-2'-ene-4'-yl)]-methylenebis(phosphonate), P$^1$-(2'-fluoro-2'-deoxyguanosin-5'-yl)-P$^2$-[7-hydroxy-5-methoxy-4-methyl-phthalan-1-on-6-yl-(3'-methylpent-2'-ene-5'-yl)]methylenebis(phosphonate), P$^1$-(2'-fluoro-2'-deoxyguanosin-5'-yl)-P$^2$-[7-hydroxy-5-methoxy-4-methyl-phthalan-1-on-6-yl-(3'-methylhex-2-ene-6'-yl)]-methylenebis(phosphonate), P$^1$-(2'-fluoro-2'-deoxyguanosin-5'-yl)-P$^2$-[7-hydroxy-5-methoxy-4-methyl-phthalan-1-on-6-yl-(3'-methylhept-2'-ene-7'-yl)]methylenebis(phosphonate), P$^1$-(2'-fluoro-2'-deoxyguanosin-5'-yl)-P$^2$-[7-hydroxy-5-methoxy-4-methyl-phthalan-1-on-6-yl-(3'-methyloct-2'-ene-8'-yl)]-methylenebis(phosphonate), P$^1$-(3'-fluoro-3'-deoxyguanosin-5'-yl)-P$^2$-[7-hydroxy-5-methoxy-4-methyl-phthalan-1-on-6-yl-(3'-methylbut-2'-ene-4'-yl)]-methylenebis(phosphonate), P$^1$-(3'-fluoro-3'-deoxyguanosin-5'-yl)-P$^2$-[7-hydroxy-5-methoxy-4-methyl-phthalan-1-on-6-yl-(3'-methylpent-2'-ene-5'-yl)]methylenebis(phosphonate), P$^1$-(3'-fluoro-3'-deoxyguanosin-5'-yl)-P$^2$-[7-hydroxy-5-methoxy-4-methyl-phthalan-1-on-6-yl-(3'-methylhex-2'-ene-6'-yl)]methylenebis(phosphonate), P$^1$-(3'-fluoro-3'-deoxyguanosin-5'-yl)-P$^2$-[7-hydroxy-5-methoxy-4-methyl-phthalan-1-on-6-yl-(3'-methylhept-2'-ene-7'-yl)]methylenebis(phosphonate), P$^1$-(3'-fluoro-3'-deoxyguanosin-5'-yl]-P$^2$-[7-hydroxy-5-methoxy-4-methyl-phthalan-1-on-6-yl-(3'-methyloct-2'-ene-8'-yl)]-methylenebis(phosphonate), P$^1$-[9-(2'-fluoro-2'-deoxy-β-D-arabinofuranosyl)guanin-5'-yl]-P$^2$-[7-hydroxy-5-methoxy-4-methyl-phthalan-1- on-6-yl-(3'-methylbut-2'-ene-4'-yl)]methylenebis(phosphonate), $P^1$-[9-(2'-fluoro-2'-deoxy-β-D-arabinofuranosyl)guanin-5'-yl]-$P^2$-[7-hydroxy-5-methoxy-4-methyl-phthalan-1-on-6-yl-(3'-methylpent-2'-ene-5'-yl)]methylenebis(phosphonate), $P^1$-[9-(2'-fluoro-2'-deoxy-β-D-arabinofuranosyl)guanin-5'-yl]-$P^2$-[7-hydroxy-5-methoxy-4-methyl-phthalan-1-on-6-yl-(3'-methylhex-2'-ene-6'-yl)]methylenebis(phosphonate), $P^1$-[9-(2'-fluoro-2'-deoxy-β-D-arabinofuranosyl)guanin-5'-yl]-$P^2$-[7-hydroxy-5-methoxy-4-methyl-phthalan-1-on-6-yl-(3'-methylhept-2'-ene-7'-yl)]methylenebis(phosphonate), $P^1$-[9-(2'-fluoro-2'-deoxy-β-D-arabinofuranosyl)guanin-5'-yl]-$P^2$-[7-hydroxy-5-methoxy-4-methyl-phthalan-1-on-6-yl-(3'-methyloct-2'-ene-8'-yl)]methylenebis(phosphonate), $P^1$-[9-(3'-fluoro-3'-deoxy-β-D-arabinofuranosyl)guanin-5'-yl]-$P^2$-[7-hydroxy-5-methoxy-4-methyl-phthalan-1-on-6-yl-(3'-methylbut-2'-ene-4'-yl)]methylenebis(phosphonate), $P^1$-[9-(3'-fluoro-3'-deoxy-β-D-arabinofuranosyl)guanin-5'-yl]-$P^2$-[7-hydroxy-5-methoxy-4-methyl-phthalan-1-on-6-yl-(3'-methylpent-2'-ene-5'-yl)]methylenebis(phosphonate), $P^1$-[9-(3'-fluoro-3'-deoxy-β-D-arabinofuranosyl)guanin-5'-yl]-$P^2$-[7-hydroxy-5-methoxy-4-methyl-phthalan-1-on-6-yl-(3'-methylhex-2'-ene-6'-yl)]methylenebis(phosphonate), $P^1$-[9-(3'-fluoro-3'-deoxy-β-D-arabinofuranosyl)guanin-5'-yl]-$P^2$-[7-hydroxy-5-methoxy-4-methyl-phthalan-1-on-6-yl-(3'-methylhept-2'-ene-7'-yl)]methylenebis(phosphonate), $P^1$-[9-(3'-fluoro-3'-deoxy-β-D-arabinofuranosyl)guanin-5'-yl]-$P^2$-[7-hydroxy-5-methoxy-4-methyl-phthalan-1-on-6-yl-(3'-methyloct-2'-ene-8'-yl)]methylenebis(phosphonate), $P^1$-(inosin-5'-yl)-$P^2$-[7-hydroxy-5-methoxy-4-methyl-phthalan-1-on-6-yl-(3'-methylbut-2'-ene-4'-yl)]methylenebis(phosphonate), $P^1$-(inosin-5'-yl)-$P^2$-[7-hydroxy-5-methoxy-4-methyl-phthalan-1-on-6-yl-(3'-methylpent-2'-ene-5'-yl)]methylenebis(phosphonate), $P^1$-(inosin-5'-yl)-$P^2$-[7-hydroxy-5-methoxy- 4-methyl-phthalan-1-on-6-yl-(3'-methylhex-2'-ene-6'-yl)]methylenebis(phosphonate), $P^1$-(inosin-5'-yl)-$P^2$-[7-hydroxy-5-methoxy-4-methyl-phthalan-1-on-6-yl-(3'-methylhept-2'-ene-7'-yl)]methylenebis(phosphonate), $P^1$-(inosin-5'-yl)-$P^2$-[7-hydroxy-5-methoxy-4-methyl-phthalan-1-on-6-yl-(3'-methyloct-2-ene-8'-yl)]methylenebis(phosphonate), $P^1$-(2'-fluoro-2'-deoxyinosin-5'-yl)-$P^2$-[7-hydroxy-5-methoxy-4-methyl-phthalan-1-on-6-yl-(3'-methylbut-2'-ene-4'-yl)]-methylenebis(phosphonate), $P^1$-(2'-fluoro-2'-deoxyinosin-5'-yl)-$P^2$-[7-hydroxy-5-methoxy-4-methyl-phthalan-1-on-6-yl-(3'-methylpent-2'-ene-5'-yl)]-methylenebis(phosphonate), $P^1$-(2'-fluoro-2'-deoxyinosin-5'-yl)-$P^2$-[7-hydroxy-5-methoxy-4-methyl-phthalan-1-on-6-yl-(3'-methylhex-2-ene-6'-yl)]-methylenebis(phosphonate), $P^1$-(2'-fluoro-2'-deoxyinosin-5'-yl)-$P^2$-[mycophenol-6-(3'-methylhept-2'-ene-7'-yl)]-methylenebis(phosphonate), $P^1$-(2'-fluoro-2'-deoxyinosin-5'-yl)-$P^2$-[7-hydroxy-5-methoxy-4-methyl-phthalan-1-on-6-yl-(3'-methyloct-2'-ene-8'-yl)]-methylenebis(phosphonate), $P^1$-(3'-fluoro-3'-deoxyinosin-5'-yl)-$P^2$-[7-hydroxy-5-methoxy-4-methyl-phthalan-1-on-6-yl-(3'-methylbut-2'-ene-4'-yl)]-methylenebis(phosphonate), $P^1$-(3'-fluoro-3'-deoxyinosin-5'-yl)-$P^2$-[7-hydroxy-5-methoxy-4-methyl-phthalan-1-on-6-yl-(3'-methylpent-2'-ene-5'-yl)]-methylenebis(phosphonate), $P^1$-(3'-fluoro-3'-deoxyinosin-5'-yl)-$P^2$-[7-hydroxy-5-methoxy-4-methyl-phthalan-1-on-6-yl-(3'-methylhex-2'-ene-6'-yl)]methylenebis(phosphonate), $P^1$-(3'-fluoro-3'-deoxyinosin-5'-yl)-$P^2$-[7-hydroxy-5-methoxy-4-methyl-phthalan-1-on-6-yl-(3'-methylhept-2'-ene-7'-yl)]-methylenebis(phosphonate), $P^1$-(3'-fluoro-3'-deoxyinosin-5'-yl)-$P^2$-[7-hydroxy-5-methoxy-4-methyl-phthalan-1-on-6-yl-(3'-methyloct-2'-ene-8'-yl)]-methylenebis(phosphonate), $P^1$-[9-(2'-fluoro-2'-deoxy-β-D-arabinofuranosyl)-hypoxanthin-5'-yl]-$P^2$-[7-hydroxy-5-methoxy-4-methyl-phthalan-1-on-6-yl-(3'-methylbut-2'-ene-4'-yl)]methylenebis(phosphonate), $P^1$-[9-(2'-fluoro-2'-deoxy-β-D-arabinofuranosyl)-hypoxanthin-5'-yl]-$P^2$-[7-hydroxy-5-methoxy-4-methyl-phthalan-1-on-6-yl-(3'-methylpent-2'-ene-5'-yl)]methylenebis(phosphonate), $P^1$-[9-(2'-fluoro-2'-deoxy-β-D-arabinofuranosyl)-hypoxanthin-5'-yl]-$P^2$-[7-hydroxy-5-methoxy-4-methyl-phthalan-1-on-6-yl-(3'-methylhex-2'-ene-6'-yl)]methylenebis(phosphonate), $P^1$-[9-(2'-fluoro-2'-deoxy-β-D-arabinofuranosyl)-hypoxanthin-5'-yl]-$P^2$-[7-hydroxy-5-methoxy-4-methyl-phthalan-1-on-6-yl-(3'-methylhept-2'-ene-7'-yl)]methylenebis(phosphonate), $P^1$-[9-(2'-fluoro-2'-deoxy-β-D-arabinofuranosyl)-hypoxanthin-5'-yl]-$P^2$-[7-hydroxy-5-methoxy-4-methyl-phthalan-1-on-6-yl-(3'-methyloct-2'-ene-8'-yl)]methylenebis(phosphonate), $P^1$-[9-(3'-fluoro-3'-deoxy-β-D-arabinofuranosyl)-hypoxanthin-5'-yl]-$P^2$-[7-hydroxy-5-methoxy-4-methyl-phthalan-1-on-6-yl-(3'-methylbut-2'-ene-4'-yl)]methylenebis(phosphonate), $P^1$-[9-(3'-fluoro-3'-deoxy-β-D-arabinofuranosyl)-hypoxanthin-5'-yl]-$P^2$-[7-hydroxy-5-methoxy-4-methyl-phthalan-1-on-6-yl-(3'-methylpent-2'-ene-5'-yl)]methylenebis(phosphonate), $P^1$-[9-(3'-fluoro-3'-deoxy-β-D-arabinofuranosyl)-hypoxanthin-5'-yl]-$P^2$-[7-hydroxy-5-methoxy-4-methyl-phthalan-1-on-6-yl-(3'-methylhex-2'-ene-6'-yl)]methylenebis(phosphonate), $P^1$-[9-(3'-fluoro-3'-deoxy-β-D-arabinofuranosyl)-hypoxanthin-5'-yl]-$P^2$-[7-hydroxy-5-methoxy-4-methyl-phthalan-1-on-6-yl-(3'-methylhept-2'-ene-7'-yl)]methylenebis(phosphonate), and $P^1$-[9-(3'-fluoro-3'-deoxy-β-D-arabinofuranosyl)-hypoxanthin-5'-yl]-$P^2$-[7-hydroxy-5-methoxy-4-methyl-phthalan-1-on-6-yl-(3'-methyloct-2'-ene-8'-yl)]methylenebis(phosphonate).

What is claimed is:
1. A compound having the following structure:

wherein
each of $R_1$, $R_2$, $R_3$, and $R_4$ is independently H, OH or F;
X is O, S, mono- or di-halomethylene, or NR wherein R is H or alkyl, or $CH_2$;
Y is OH, SH or F; and
each of $W_1$ and $W_2$ is independently H, OH, =O, OR, SH, SR, $NH_2$, NHR or $NR_2$, wherein R is $C_1$–$C_5$ alkyl and n is an integer from 1 to 5.

2. The compound of claim 1, wherein the compound is selected from the group consisting of:

$P^1$-(2',3'-O-isopropylideneadenosin-5'-yl)-P2-[7-hydroxy-5-methoxy-4-methyl-phthalan-1-on-6-yl-(3'-methylhex-2'-ene-6'-yl)methylenebis(phosphonate), $P^1$-(2',3'-O-isopropylideneadenosin-5'-yl)-$P^2$-[7-hydroxy-5-methoxy-4-methyl-phthalan-1-on-6-yl-(3'-methylbut-2'-ene-4'-yl)]methylenebis(phosphonate), $P^1$-(2',3'-O-isopropylideneadenosin-5'-yl)-$P^2$-[7-hydroxy-5-methoxy-4-methyl-phthalan-1-on-6-yl-(3'-methylpent-2'-ene-5'-yl)]methylenebis(phosphonate), $P^1$-(2',3'-O-isopropylideneadenosin-5'-yl)-$P^2$-[7-hydroxy-5-methoxy-4-methyl-phthalan-1-on-6-yl-(3'-methylhept-2'-ene-7'-yl)]methylenebis(phosphonate), $P^1$-(2',3'-O-isopropylideneadenosin-5'-yl)-$P^2$-[7-hydroxy-5-methoxy-4-methyl-phthalan-1-on-6-yl-(3'-methylocta-2'-ene-8'-yl)]methylenebis(phosphonate), $P^1$-(3'-O-acetyl-2'-fluoro-2'-deoxyadenosin-5'-yl)-$P^2$-[7-hydroxy-5-methoxy-4-methyl-phthalan-1-on-6-yl-(3'-methylbut-2'-ene-4'-yl)]methylenebis(phosphonate), $P^1$-(3'-O-acetyl-2'-fluoro-2'-deoxyadenosin-5'-yl)-$P^2$-[7-hydroxy-5-methoxy-4-methyl-phthalan-1-on-6-yl-(3'-methylpent-2'-ene-5'-yl)]methylenebis(phosphonate), $P^1$-(3'-O-acetyl-2'-fluoro-2'-deoxyadenosin-5'-yl)-$P^2$-[7-hydroxy-5-methoxy-4-methyl-phthalan-1-on-6-yl-(3'-methylhex-2'-ene-6'-yl)]methylenebis(phosphonate), $P^1$-(3'-O-acetyl-2'-fluoro-2'-deoxyadenosin-5'-yl)-$P^2$-(7-hydroxy-5-methoxy-4-methyl-phthalan-1-on-6-yl-(3'-methylhept-2'-ene-7'-yl)]methylenebis(phosphonate), $P^1$-(3'-O-acetyl-2'-fluoro-2'-deoxyadenosin-5'-yl)-$P^2$-[7-hydroxy-5-methoxy-4-methyl-phthalan-1-on-6-yl-(3'-methyloct-2'-ene-8'-yl)]methylenebis(phosphonate), $P^1$-(2'-O-acetyl-3'-fluoro-3'-deoxyadenosin-5'-yl)-$P^2$-[7-hydroxy-5-methoxy-4-methyl-phthalan-1-on-6-yl-(3'-methylbut-2'-ene-4'-yl)]methylenebis(phosphonate), $P^1$-(2'-O-acetyl-3'-fluoro-3'-deoxyadenosin-5'-yl)-$P^2$-[7-hydroxy-5-methoxy-4-methyl-phthalan-1-on-6-yl-(3'-methylpent-2'-ene-5'-yl)]methylenebis(phosphonate), $P^1$-(2'-O-acetyl-3'-fluoro-3'-deoxyadenosin-5'-yl)-$P^2$-[7-hydroxy-5-methoxy-4-methyl-phthalan-1-on-6-yl-(3'-methylhex-2'-ene-6'-yl)]methylenebis(phosphonate), $P^1$-(2'-O-acetyl-3'-fluoro-3'-deoxyadenosin-5'-yl)-$P^2$-(7-hydroxy-5-methoxy-4-methyl-phthalan-1-on-6-yl-(3'-methylhept-2'-ene-7'-yl)]methylenebis(phosphonate), $P^1$-(2'-O-acetyl-3'-fluoro-3'-deoxyadenosin-5'-yl)-$P^2$-[7-hydroxy-5-methoxy-4-methyl-phthalan-1-on-6-yl-(3'-methyloct-2'-ene-8'-yl)]methylenebis(phosphonate), $P^1$-[9-(3'-O-acetyl-2'-fluoro-2'-deoxy-β-D-arabinofuranosyl)adenin-5'-yl]-$P^2$-[7-hydroxy-5-methoxy-4-methyl-phthalan-1-on-6-yl-(3'-methylbut-2'-ene-4'-yl)]methylenebis(phosphonate), $P^1$-[9-(3'-O-acetyl-2'-fluoro-2'-deoxy-β-D-arabinofuranosyl)adenin-5'-yl]-$P^2$-[7-hydroxy-5-methoxy-4-methyl-phthalan-1-on-6-yl-(3'-methylpent-2'-ene-5'-yl)]methylenebis(phosphonate), $P^1$-[9-(3'-O-acetyl-2'-fluoro-2'-deoxy-β-D-arabinofuranosyl)adenin-5'-yl]-$P^2$-[7-hydroxy-5-methoxy-4-methyl-phthalan-1-on-6-yl-(3'-methylhex-2'-ene-6'-yl)]methylenebis(phosphonate), $P^1$-[9-(3'-O-acetyl-2'-fluoro-2'-deoxy-β-D-arabinofuranosyl)adenin-5'-yl]-$P^2$-[7-hydroxy-5-methoxy-4-methyl-phthalan-1-on-6-yl-(3'-methylhept-2'-ene-7'-yl)]methylenebis(phosphonate), $P^1$-[9-(3'-O-acetyl-2'-fluoro-2'-deoxy-β-D-arabinofuranosyl) adenin-5'-yl]-$P^2$-[7-hydroxy-5-methoxy-4-methyl-phthalan-1-on-6-yl-(3'-methyloct-ene-8'-yl)]methylenebis(phosphonate), $P^1$-[9-(2'-O-acetyl-3'-fluoro-3'-deoxy-β-D-arabinofuranosyl)adenin-5'-yl]-$P^2$-[7-hydroxy-5-methoxy-4-methyl-phthalan-1-on-6-yl-(3'-methylbut-2'-ene-4'-yl)]methylenebis(phosphonate), $P^1$-[9-(2'-O-acetyl-3'-fluoro-3'-deoxy-β-D-arabinofuranosyl)adenin-5'-yl]-$P^2$-[7-hydroxy-5-methoxy-4-methyl-phthalan-1-on-6-yl-(3'-methylpent-2'-ene-5'-yl)]methylenebis(phosphonate), $P^1$-[9-(2'-O-acetyl-3'-fluoro-3'-deoxy-β-D-arabinofuranosyl)adenin-5'-yl]-$P^2$-[7-hydroxy-5-methoxy-4-methyl-phthalan-1-on-6-yl-(3'-methylhex-2'-ene-6'-yl)]methylenebis(phosphonate), $P^1$-[9-(2'-O-acetyl-3'-fluoro-3'-deoxy-β-D-arabinofuranosyl)adenin-5'-yl]-$P^2$-[7-hydroxy-5-methoxy-4-methyl-phthalan-1-on-6-yl-(3'-methylhept-2'-ene-7'-yl)]methylenebis(phosphonate), $P^1$-[9-(2'-O-acetyl-3'-fluoro-3'-deoxy-β-D-arabinofuranosyl)adenin-5'-yl]-$P^2$-[7-hydroxy-5-methoxy-4-methyl-phthalan-1-on-6-yl-(3'-methyloct-2'-ene-8'-yl)]methylenebis(phosphonate), $P^1$-(2',3'-O-isopropylideneguanosin-5'-yl)-$P^2$-[7-hydroxy-5-methoxy-4-methyl-phthalan-1-on-6-yl-(3'-methylbut-2'-ene-4'-yl)]methylenebis(phosphonate), $P^1$-(2',3'-O-isopropylideneguanosin-5'-yl)-$P^2$-[7-hydroxy-5-methoxy-4-methyl-phthalan-1-on-6-yl-(3'-methylpent-2'-ene-5'-yl)]methylenebis(phosphonate), $P^1$-(2',3'-O-isopropylideneguanosin-5'-yl)-$P^2$-[7-hydroxy-5-methoxy-4-methyl-phthalan-1-on-6-yl-(3'-methylhex-2'-ene-6'-yl)]methylenebis(phosphonate), $P^1$-(2',3'-O-isopropylideneguanosin-5'-yl)-$P^2$-[7-hydroxy-5-methoxy-4-methyl-phthalan-1-on-6-yl-(3'-methylhept-2'-ene-7'-yl)]methylenebis(phosphonate), $P^1$-(2',3'-O-isopropylideneguanosin-5'-yl)-$P^2$-[7-hydroxy-5-methoxy-4-methyl-phthalan-1-on-6-yl-(3'-methyloct-2'-ene-8'-yl)]methylenebis(phosphonate), $P^1$-(3'-O-acetyl-2'-fluoro-2'-deoxyguanosin-5'-yl)-$P^2$-[7-hydroxy-5-methoxy-4-methyl-phthalan-1-on-6-yl-(3'-methylbut-2'-ene-4'-yl)lmethylenebis(phosphonate), $P^1$-(3'-O-acetyl-2'-fluoro-2'-deoxyguanosin-5'-yl)-$P^2$-[7-hydroxy-5-methoxy-4-methyl-phthalan-1-on-6-yl-(3'-methylpent-2'-ene-5'-yl)]methylenebis(phosphonate), P¹-(3'-O-acetyl-2'-fluoro-2'-deoxyguanosin-5'-yl)-P²-[7-hydroxy-5-methoxy-4-methyl-phthalan-1-on-6-yl-(3'-methylhex-2'-ene-6'-yl)]methylenebis(phosphonate), P¹-(3'-O-acetyl-2'-fluoro-2'-deoxyguanosin-5'-yl)-P²-[7-hydroxy-5-methoxy-4-methyl-phthalan-1-on-6-yl-(3'-methylhept-2'-ene-7'-yl)]methylenebis(phosphonate), P¹-(3'-O-acetyl-2'-fluoro-2'-deoxyguanosin-5'-yl)-P²-[7-hydroxy-5-methoxy-4-methyl-phthalan-1-on-6-yl-(3'-methyloct-2'-ene-8'-yl)]methylenebis(phosphonate), P¹-(2'-O-acetyl-3'-fluoro-3'-deoxyguanosin-5'-yl)-P²-[7-hydroxy-5-methoxy-4-methyl-phthalan-1-on-6-yl-(3'-methylbut-2'-ene-4'-yl)]methylenebis(phosphonate), P¹-(2'-O-acetyl-3'-fluoro-3'-deoxyguanosin-5'-yl)-P²-[7-hydroxy-5-methoxy-4-methyl-phthalan-1-on-6-yl-(3'-methylpent-2'-ene-5'-yl)]methylenebis(phosphonate), P¹-(2'-O-acetyl-3'-fluoro-3'-deoxyguanosin-5'-yl)-P²-[7-hydroxy-5-methoxy-4-methyl-phthalan-1-on-6-yl-(3'-methylhex-2'-ene-6'-yl)]methylenebis(phosphonate), P¹-(2'-O-acetyl-3'-fluoro-3'-deoxyguanosin-5'-yl)-P²-[7-hydroxy-5-methoxy-4-methyl-phthalan-1-on-6-yl-(3'-methylhept-2'-ene-7'-yl)]methylenebis(phosphonate), P¹-(2'-O-acetyl-3'-fluoro-3'-deoxyguanosin-5'-yl]-P²-[7-hydroxy-5-methoxy-4-methyl-phthalan-1-on-6-yl-(3'-methyloct-2'-ene-8'-yl)]methylenebis(phosphonate), P¹-[9-(3'-O-acetyl-2'-fluoro-2'-deoxy-β-D-arabinofuranosyl) guanin-5'-yl]-P²-[7-hydroxy-5-methoxy-4-methyl-phthalan-1-on-6-yl-(3'-methylbut-2'-ene-4'-yl)]methylenebis(phosphonate), P¹-[9-(3'-O-acetyl-2'-fluoro-2'-deoxy-β-D-arabinofuranosyl) guanin-5'-yl]-P²-[7-hydroxy-5-methoxy-4-methyl-phthalan-1-on-6-yl-(3'-methylpent-2'-ene-5'-yl)]methylenebis(phosphonate), P¹-[9-(3'-O-acetyl-2'-fluoro-2'-deoxy-β-D-arabinofuranosyl) guanin-5'-yl]-P²-[7-hydroxy-5-methoxy-4-methyl-phthalan-1-on-6-yl-(3'-methylhex-2'-ene-6'-yl)]methylenebis(phosphonate), P¹-[9-(3'-O-acetyl-2'-fluoro-2'-deoxy-β-D-arabinofuranosyl) guanin-5'-yl]-P²-[7-hydroxy-5-methoxy-4-methyl-phthalan-1-on-6-yl-(3'-methylhept-2'-ene-7'-yl)]methylenebis(phosphonate), P¹-[9-(3'-O-acetyl-2'-fluoro-2'-deoxy-β-D-arabinofuranosyl) guanin-5'-yl]-P²-[7-hydroxy-5-methoxy-4-methyl-phthalan-1-on-6-yl-(3'-methyloct-2'-ene-8'-yl)]methylenebis(phosphonate), P¹-[9-(2'-O-acetyl-3'-fluoro-3'-deoxy-β-D-arabinofuranosyl)guanin-5'-yl]-P²-[7-hydroxy-5-methoxy-4-methyl-phthalan-1-on-6-yl-(3'-methylbut-2'-ene-4'-yl)]methylenebis(phosphonate), P¹-[9-(2'-O-acetyl-3'-fluoro-3'-deoxy-β-D-arabinofuranosyl)guanin-5'-yl]-P²-[7-hydroxy-5-methoxy-4-methyl-phthalan-1-on-6-yl-(3'-methylpent-2'-ene-5'-yl)]methylenebis(phosphonate), P¹-[9-(2'-O-acetyl-3'-fluoro-3'-deoxy-β-D-arabinofuranosyl)guanin-5'-yl]-P²-[7-hydroxy-5-methoxy-4-methyl-phthalan-1-on-6-yl-(3'-methylhex-2'-ene-6'-yl)]methylenebis(phosphonate), P¹-[9-(2'-O-acetyl-3'-fluoro-3'-deoxy-β-D-arabinofuranosyl)guanin-5'-yl]-P²-[7-hydroxy-5-methoxy-4-methyl-phthalan-1-on-6-yl-(3'-methylhept-2'-ene-7'-yl)]methylenebis(phosphonate), P¹-[9-(2'-O-acetyl-3'-fluoro-3'-deoxy-β-D-arabinofuranosyl)guanin-5'-yl]-P²-[7-hydroxy-5-methoxy-4'-methyl-phthalan-1-on-6-yl-(3'-methyloct-2'-ene-8'-yl)]methylenebis(phosphonate), P¹-(2',3'-O-isopropylideneinosin-5'-yl)-P²-[7-hydroxy-5-methoxy-4-methyl-phthalan-1-on-6-yl-(3'-methylbut-2'-ene-4'-yl)]methylenebis(phosphonate), P¹-(2',3'-O-isopropylideneinosin-5'-yl)-P²-[7-hydroxy-5-methoxy-4-methyl-phthalan-1-on-6-yl-(3'-methylpent-2'-ene-5'-yl)]methylenebis(phosphonate), P¹-(2',3'-O-isopropylideneinosin-5'-yl)-P²-[7-hydroxy-5-methoxy-4-methyl-phthalan-1-on-6-yl-(3'-methylhex-2'-ene-6'-yl)]methylenebis(phosphonate), P¹-(2',3'-O-isopropylideneinosin-5'-yl)-P²-[7-hydroxy-5-methoxy-4-methyl-phthalan-1-on-6-yl-(3'-methylhept-2'-ene-7'-yl)]methylenebis(phosphonate), P¹-(2',3'-O-isopropylideneinosin-5'-yl)-P²-[7-hydroxy-5-methoxy-4-methyl-phthalan-1-on-6-yl-(3'-methyloct-2'-ene-8'-yl)]methylenebis(phosphonate), P¹-(3'-O-acetyl-2'-fluoro-2'-deoxyinosin-5'-yl)-P²-[7-hydroxy-5-methoxy-4-methyl-phthalan-1-on-6-yl-(3'-methylbut-2'-ene-4'-yl)]methylenebis(phosphonate), P¹-(3'-O-acetyl-2'-fluoro-2'-deoxyinosin-5'-yl)-P²-[7-hydroxy-5-methoxy-4-methyl-phthalan-1-on-6-yl-(3'-methylpent-2'-ene-5'-yl)]methylenebis(phosphonate), P¹-(3'-O-acetyl-2'-fluoro-2'-deoxyinosin-5'-yl)-P²-[7-hydroxy-5-methoxy-4-methyl-phthalan-1-on-6-yl-(3'-methylhex-2'-ene-6'-yl)]methylenebis(phosphonate), P¹-(3'-O-acetyl-2'-fluoro-2'-deoxyinosin-5'-yl)-P²-[7-hydroxy-5-methoxy-4-methyl-phthalan-1-on-6-yl-(3'-methylhept-2'-ene-7'-yl)]methylenebis(phosphonate), P¹-(3'-O-acetyl-2'-fluoro-2'-deoxyinosin-5'-yl)-P²-[7-hydroxy-5-methoxy-4-methyl-phthalan-1-on-6-yl-(3'-methyloct-2'-ene-8'-yl)]methylenebis(phosphonate), P¹-(2'-O-acetyl-3'-fluoro-3'-deoxyinosin-5'-yl)-P²-[7-hydroxy-5-methoxy-4-methyl-phthalan-1-on-6-yl-(3'-methylbut-2'-ene-4'-yl)]methylenebis(phosphonate), P¹-(2'-O-acetyl-3'-fluoro-3'-deoxyinosin-5'-yl)-P²-[7-hydroxy-5-methoxy-4-methyl-phthalan-1-on-6-yl-(3'-methylpent-2'-ene-5'-yl)]methylenebis(phosphonate), P¹-(2'-O-acetyl-3'-fluoro-3'-deoxyinosin-5'-yl)-P²-[7-hydroxy-5-methoxy-4-methyl-phthalan-1-on-6-yl-(3'-methylhex-2'-ene-6'-yl)]methylenebis(phosphonate), P¹-(2'-O-acetyl-3'-fluoro-3'-deoxyinosin-5'-yl)-P²-[7-hydroxy-5-methoxy-4-methyl-phthalan-1-on-6-yl-(3'-methylhept-2'-ene-7'-yl)]methylenebis(phosphonate), P¹-(2'-O-acetyl-3'-fluoro-3'-deoxyinosin-5'-yl]-P²-[7-hydroxy-5-methoxy-4-methyl-phthalan-1-on-6-yl-(3'-methyloct-2'-ene-8'-yl)]methylenebis(phosphonate), P¹-[9-(3'-O-acetyl-2'-fluoro-2'-deoxy-β-D-arabinofuranosyl)hypoxanthin-5'-yl]-P²-[7-hydroxy-5-methoxy-4-methyl-phthalan-1-on-6-yl-(3'-methylbut-2'-ene-4'-yl)]methylenebis(phosphonate), P¹-[9-(3'-O-acetyl-2'-fluoro-2'-deoxy-β-D-arabinofuranosyl)hypoxanthin-5'-yl]-P²-[7-hydroxy-5-methoxy-4-methyl-phthalan-1-on-6-yl-(3'-methylpent-2'-ene-5'-yl)]methylenebis(phosphonate), P¹-[9-(3'-O-acetyl-2'-fluoro-2'-deoxy-β-D-arabinofuranosyl)hypoxanthin-5'-yl]-P²-[7-hydroxy-5-methoxy-4-methyl-phthalan-1-on-6-yl-(3'-methylhex-2'-ene-6'-yl)]methylenebis(phosphonate), P¹-[9-(3'-O-acetyl-2'-fluoro-2'-deoxy-β-D-arabinofuranosyl)hypoxanthin-5'-yl]-P²-[7-hydroxy-5-methoxy-4-methyl-phthalan-1-on-6-yl-(3'-methylhept-2'-ene-7'-yl)]methylenebis(phosphonate), P¹-[9-(3'-O-acetyl-2'-fluoro-2'-deoxy-β-D-arabinofuranosyl)hypoxanthin-5'-yl]-P²-[7-hydroxy-5-methoxy-4-methyl-phthalan-1-on-6-yl-(3'-methyloct-2'-ene-8'-yl)]methylenebis(phosphonate), P$^1$-[9-(2'-O-acetyl-3'-fluoro-3'-deoxy-β-D-arabinofuranosyl)hypoxanthin-5'-yl]-P$^2$-[7-hydroxy-5-nmethoxy-4-methyl-phthalan-1-on-6-yl-(3'-methylbut-2'-ene-4'-yl)]methylenebis(phosphonate), P$^1$-[9-(2'-O-acetyl-3'-fluoro-3'-deoxy-β-D-arabinofuranosyl)hypoxanthin-5'-yl]-P$^2$-[7-hydroxy-5-methoxy-4-methyl-phthalan-1-on-6-yl-(3'-methylpent-2'-ene-5'-yl)]methylenebis(phosphonate), P$^1$-[9-(2'-O-acetyl-3'-fluoro-3'-deoxy-β-D-arabinofuranosyl)hypoxanthin-5'-yl]-P$^2$-[7-hydroxy-5-methoxy-4-methyl-phthalan-1-on-6-yl-(3'-methylhex-2'-ene-6'-yl)]methylenebis(phosphonate), P$^1$-[9-(2'-O-acetyl-3'-fluoro-3'-deoxy-β-D-arabinofuranosyl)hypoxanthin-5'-yl]-P$^2$-[7-hydroxy-5-methoxy-4-methyl-phthalan-1-on-6-yl-(3'-methylhept-2'-ene-7'-yl)]methylenebis(phosphonate), and P$^1$-[9-(2'-O-acetyl-3'-fluoro-3'-deoxy-β-D-arabinofuranosyl)hypoxanthin-5'-yl]-P$^2$-[7-hydroxy-5-methoxy-4-methyl-phthalan-1-on-6-yl-(3'-methyloct-2'-ene-8'-yl)]methylenebis(phosphonate).

3. The compound of claim 1, wherein the compound is selected from the group consisting of:

P$^1$-(adenosin-5'-yl)-P$^2$-[7-hydroxy-5-methoxy-4-methylphthalan-1-on-6-yl-(3'-methylpent-2'-ene-5'-yl)]methylenebis(phosphonate), P$^1$-(adenosin-5'-yl)-P$^2$-[7-hydroxy-5-methoxy-4-methyl-phthalan-1-on-6-yl-(3'-methylhept-2'-ene-7?-yl)]methylenebis(phosphonate), P$^1$-(adenosin-5'-yl)-P$^2$-[7-hydroxy-5-methoxy-4-methyl-phthalan-1-on-6-yl-(3'-methyloct-2-ene-8'-yl)]methylenebis(phosphonate), P$^1$-(2'-fluoro-2'-deoxyadenosin-5'-yl)-P$^2$-[7-hydroxy-5-methoxy-4-methyl-phthalan-1-on-6-yl-(3'-methylbut-2'-ene-4'-yl)]-methylenebis(phosphonate), P$^1$-(2'-fluoro-2'-deoxyadenosin-5'-yl)-P$^2$-[7-hydroxy-5-methoxy-4-methyl-phthalan-1-on-6-yl-(3'-methylpent-2'-ene-5'-yl)]-methylenebis(phosphonate), P$^1$-(2'-fluoro-2'-deoxyadenosin-5'-yl)-P$^2$-[7-hydroxy-5-methoxy-4-methyl-phthalan-1-on-6-yl-(3'-methylhex-2-ene-6'-yl)]methylenebis(phosphonate), P$^1$-(2'-fluoro-2'-deoxyadenosin-5'-yl)-P$^2$-[7-hydroxy-5-methoxy-4-methyl-phthalan-1-on-6-yl-(3'-methylhept-2'-ene-7'-yl)]-methylenebis(phosphonate), P$^1$-(2'-fluoro-2'-deoxyadenosin-5'-yl)-P$^2$-[7-hydroxy-5-methoxy-4-methyl-phthalan-1-on-6-yl-(3'-methyloct-2'-ene-8'-yl)]-methylenebis(phosphonate), P$^1$-(3'-fluoro-3'-deoxyadenosin-5'-yl)-P$^2$-[7-hydroxy-5-methoxy-4-methyl-phthalan-1-on-6-yl-(3'-methylbut-2'-ene-4'-yl)]-methylenebis(phosphonate), P$^1$-(3'-fluoro-3'-deoxyadenosin-5'-yl)-P$^2$-[7-hydroxy-5-methoxy-4-methyl-phthalan-1-on-6-yl-(3'-methylpent-2'-ene-5'-yl)]-methylenebis(phosphonate), P$^1$-(3'-fluoro-3'-deoxyadenosin-5'-yl)-P$^2$-[-hydroxy-5-methoxy-4-methyl-phthalan-1-on-6-yl-(3'-methylhex-2'-ene-6'-yl)]methylenebis(phosphonate), P$^1$-(3'-fluoro-3'-deoxyadenosin-5'-yl)-P$^2$-[7-hydroxy-5-methoxy-4-methyl-phthalan-1-on-6-yl-(3'-methylhept-2'-ene-7'-yl)]methylenebis(phosphonate), P$^1$-(3'-fluoro-3'-deoxyadenosin-5'-yl)-P$^2$-[7-hydroxy-5-methoxy-4-methyl-phthalan-1-on-6-yl-(3'-methyloct-2'-ene-8'-yl)]methylenebis(phosphonate), P$^1$-[9-(2'-fluoro-2'-deoxy-β-D-arabinofuranosyl)adenin-5'-yl]-P$^2$-[7-hydroxy-5-methoxy-4-methyl-phthalan-1-on-6-yl-(3'-methylbut-2'-ene-4'-yl)]methylenebis(phosphonate), P$^1$-[9-(2'-fluoro-2'-deoxy-β-D-arabinofuranosyl)adenin-5'-yl]-P$^2$-[7-hydroxy-5-methoxy-4-methyl-phthalan-1-on-6-yl-(3'-methylpent-2'-ene-5'-yl)]methylenebis(phosphonate), P$^1$-[9-(2'-fluoro-2'-deoxy-β-D-arabinofuranosyl)adenin-5'-yl] P$^2$-[7-hydroxy-5-methoxy-4-methyl-phthalan-1-on-6-yl-(3'-methylhex-2'-ene-6'-yl)]methylenebis(phosphonate), P$^1$-[9-(2'-fluoro-2'-deoxy-β-D-arabinofuranosyl)adenin-5'-yl]-P$^2$-[7-hydroxy-5-methoxy-4-methyl-phthalan-1-on-6-yl-(3'-methylhept-2'-ene-7'-yl)lmethylenebis(phosphonate), P$^1$-[9-(2'-fluoro-2'-deoxy-β-D-arabinofuranosyl)adenin-5'-yl]-P$^2$-[7-hydroxy-5-methoxy-4-methyl-phthalan-1-on-6-yl-(3'-methyloct-2'-ene-8'-yl)]methylenebis(phosphonate), P$^1$-[9-(3'-fluoro-3'-deoxy-β-D-arabinofuranosyl)adenin-5'-yl]-P$^2$-[7-hydroxy-5-methoxy-4-methyl-phthalan-1-on-6-yl-(3'-methylbut-2'-ene-4'-yl)]methylenebis(phosphonate), P$^1$-[9-(3'-fluoro-3'-deoxy-β-D-arabinofuranosyl)adenin-5'-yl]-P$^2$-[7-hydroxy-5-methoxy-4-methyl-phthalan-1-on-6-yl-(3'-methylpent-2'-ene-5'-yl)]methylenebis(phosphonate), P$^1$-[9-(3'-fluoro-3'-deoxy-β-D-arabinofuranosyl)adenin-5'-yl]-P$^2$-[7-hydroxy-5-methoxy-4-methyl-phthalan-1-on-6-yl-(3'-methylhex-2'-ene-6'-yl)]methylenebis(phosphonate), P$^1$-[9-(3'-fluoro-3'-deoxy-β-D-arabinofuranosyl)adenin-5'-yl]-P$^2$-[7-hydroxy-5-methoxy-4-methyl-phthalan-1-on-6-yl-(3'-methylhept-2'-ene-7'-yl)]methylenebis(phosphonate), P$^1$-[9-(3'-fluoro-3'-deoxy-β-D-arabinofuranosyl)adenin-5'-yl]-P$^2$-[7-hydroxy-5-methoxy-4-methyl-phthalan-1-on-6-yl-(3'-methyloct-2'-ene-8'-yl)]methylenebis(phosphonate), P$^1$-(guanosin-5'-yl)-P$^2$-[7-hydroxy-5-methoxy-4-methyl-phthalan-1-on-6-yl-(3'-methylbut-2'-ene-4'-yl)]methylenebis(phosphonate), P$^1$-(guanosin-5'-yl)-P$^2$-[7-hydroxy-5-methoxy-4-methyl-phthalan-1-on-6-yl-(3'-methylpent-2'-ene-5'-yl)]methylenebis(phosphonate), P$^1$-(guanosin-5'-yl)-P$^2$-[7-hydroxy-5-methoxy-4-methyl-phthalan-1-on-6-yl-(3'-methylhex-2'-ene-6'-yl)]methylenebis(phosphonate), P$^1$-(guanosin-5'-yl)-P$^2$-[7-hydroxy-5-methoxy-4-methyl-phthalan-1-on-6-yl-(3'-methylhept-2'-ene-7'-yl)]methylenebis(phosphonate), P$^1$-(guanosin-5'-yl)-P$^2$-[7-hydroxy-5-methoxy-4-methyl-phthalan-1-on-6-yl-(3'-methyloct-2-ene-8'-yl)]methylenebis(phosphonate), P$^1$-(2'-fluoro-2'-deoxyguanosin-5'-yl)-P$^2$-[7-hydroxy-5-methoxy-4-methyl-phthalan-1-on-6-yl-(3'-methylbut-2'-ene-4'-yl)]-methylenebis(phosphonate), P$^1$-(2'-fluoro-2'-deoxyguanosin-5'-yl)-P$^2$-[7-hydroxy-5-methoxy-4-methyl-phthalan-1-on-6-yl-(3'-methylpent-2'-ene-5'-yl)]methylenebis(phosphonate), P$^1$-(2'-fluoro-2'-deoxyguanosin-5'-yl)-P$^2$-[7-hydroxy-5-methoxy-4-methyl-phthalan-1-on-6-yl-(3'-methylhex-2-ene-6'-yl)]methylenebis(phosphonate), P$^1$-(2'-fluoro-2'-deoxyguanosin-5'-yl)-P$^2$-[7-hydroxy-5-methoxy-4-methyl-phthalan-1-on-6-yl-(3'-methylhept-2'-ene-7'-yl)]methylenebis(phosphonate), P$^1$-(2'-fluoro-2'-deoxyguanosin-5'-yl)-P$^2$-[7-hydroxy-5-methoxy-4-methyl-phthalan-1-on-6-yl-(3'-methyloct-2'-ene-8'-yl)]methylenebis(phosphonate), P$^1$-(3'-fluoro-3'-deoxyguanosin-5'-yl)-P$^2$-[7-hydroxy-5-methoxy-4-methyl-phthalan-1-on-6-yl-(3'-methylbut-2'-ene-4'-yl)]methylenebis(phosphonate), P$^1$-(3'-fluoro-3'-deoxyguanosin-5'-yl)-P$^2$-[7-hydroxy-5-methoxy-4-methyl-phthalan-1-on-6-yl-(3'-methylpent-2'-ene-5'-yl)]methylenebis(phosphonate), P$^1$-(3'-fluoro-3'-deoxyguanosin-5'-yl)-P$^2$-[7-hydroxy-5-methoxy-4-methyl-phthalan-1-on-6-yl-(3'-methylhex-2'-ene-6'-yl)]methylenebis(phosphonate), P$^1$-(3'-fluoro-3'-deoxyguanosin-5'-yl)-P$^2$-[7-hydroxy-5-methoxy-4-methyl-phthalan-1-on-6-yl-(3'-methylhept-2'-ene-7'-yl)]methylenebis(phosphonate), P$^1$-(3'-fluoro-3'-deoxyguanosin-5'-yl]-P$^2$-[7-hydroxy-5-methoxy-4-methyl-phthalan-1-on-6-yl-(3'-methyloct-2'-ene-8'-yl)]methylenebis(phosphonate), P$^1$-[9-(2'-fluoro-2'-deoxy-β-D-arabinofuranosyl)guanin-5'-yl]-P$^2$-[7-hydroxy-5-methoxy-4-methyl-phthalan-1-on-6-yl-(3'-methylbut-2'-ene-4'-yl)]methylenebis(phosphonate), P$^1$-[9-(2'-fluoro-2'-deoxy-β-D-arabinofuranosyl)guanin-5'-yl]-P$^2$-[7-hydroxy-5-methoxy-4-methyl-phthalan-1-on-6-yl-(3'-methylpent-2'-ene-5'-yl)]methylenebis(phosphonate), P$^1$-[9-(2'-fluoro-2'-deoxy-β-D-arabinofuranosyl)guanin-5'-yl]-P$^2$-[7-hydroxy-5-methoxy-4-methyl-phthalan-1-on-6-yl-(3'-methylhex-2'-ene-6'-yl)]methylenebis(phosphonate), P$^1$-[9-(2'-fluoro-2'-deoxy-β-D-arabinofuranosyl)guanin-5'-yl]-P$^2$-[7-hydroxy-5-methoxy-4-methyl-phthalan-1-on-6-yl-(3'-methylhept-2'-ene-7'-yl)]methylenebis(phosphonate), P$^1$-[9-(2'-fluoro-2'-deoxy-β-D-arabinofuranosyl)guanin-5'-yl]-P$^2$-[7-hydroxy-5-methoxy-4-methyl-phthalan-1-on-6-yl-(3'-methyloct-2'-ene-8'-yl)]methylenebis(phosphonate), P$^1$-[9-(3'-fluoro-3'-deoxy-β-D-arabinofuranosyl)guanin-5'-yl]-P$^2$-[7-hydroxy-5-methoxy-4-methyl-phthalan-1-on-6-yl-(3'-methylbut-2'-ene-4'-yl)]methylenebis(phosphonate), P$^1$-[9-(3'-fluoro-3'-deoxy-β-D-arabinofuranosyl)guanin-5'-yl]-P$^2$-[7-hydroxy-5-methoxy-4-methyl-phthalan-1-on-6-yl-(3'-methylpent-2'-ene-5'-yl)]methylenebis(phosphonate), P$^1$-[9-(3'-fluoro-3'-deoxy-β-D-arabinofuranosyl)guanin-5'-yl]-P$^2$-[7-hydroxy-5-methoxy-4-methyl-phthalan-1-on-6-yl-(3'-methylhex-2'-ene-6'-yl)]methylenebis(phosphonate), P$^1$-[9-(3'-fluoro-3'-deoxy-β-D-arabinofuranosyl)guanin-5'-yl]-P$^2$-[7-hydroxy-5-methoxy-4-methyl-phthalan-1-on-6-yl-(3'-methylhept-2'-ene-7'-yl)]methylenebis(phosphonate), P$^1$-[9-(3'-fluoro-3'-deoxy-β-D-arabinofuranosyl)guanin-5'-yl]-P$^2$-[7-hydroxy-5-methoxy-4-methyl-phthalan-1-on-6-yl-(3'-methyloct-2'-ene-8'-yl)]methylenebis(phosphonate), P$^1$-(inosin-5'-yl)-P$^2$-[7-hydroxy-5-methoxy-4-methyl-phthalan-1-on-6-yl-(3'-methylbut-2'-ene-4'-yl)]methylenebis(phosphonate), P$^1$-(inosin-5'-yl)-P$^2$-[7-hydroxy-5-methoxy-4-methyl-phthalan-1-on-6-yl-(3'-methylpent-2'-ene-5'-yl)]methylenebis(phosphonate), P$^1$-(inosin-5'-yl)-P$^2$-[7-hydroxy-5-methoxy-4-methyl-phthalan-1-on-6-yl-(3'-methylhex-2'-ene-6'-yl)]methylenebis(phosphonate), P$^1$-(inosin-5'-yl)-P$^2$-[7-hydroxy-5-methoxy-4-methyl-phthalan-1-on-6-yl-(3'-methylhept-2'-ene-7'-yl)]methylenebis(phosphonate), P$^1$-(inosin-5'-yl)-P$^2$-[7-hydroxy-5-methoxy-4-methyl-phthalan-1-on-6-yl-(3'-methyloct-2'-ene-8'-yl)]methylenebis(phosphonate), P$^1$-(2'-fluoro-2'-deoxyinosin-5'-yl)-P$^2$-[7-hydroxy-5-methoxy-4-methyl-phthalan-1-on-6-yl-(3'-methylbut-2'-ene-4'-yl)]methylenebis(phosphonate), P$^1$-(2'-fluoro-2'-deoxyinosin-5'-yl)-P$^2$-[7-hydroxy-5-methoxy-4-methyl-phthalan-1-on-6-yl-(3'-methylpent-2'-ene-5'-yl)]methylenebis(phosphonate), P$^1$-(2'-fluoro-2'-deoxyinosin-5'-yl)-P$^2$-[7-hydroxy-5-methoxy-4-methyl-phthalan-1-on-6-yl-(3'-methylhex-2-ene-6'-yl)]methylenebis(phosphonate), P$^1$-(2'-fluoro-2'-deoxyinosin-5'-yl)-P$^2$-[mycophenol-6-(3'-methylhept-2'-ene-7'-yl)]methylenebis(phosphonate), P$^1$-(2'-fluoro-2'-deoxyinosin-5'-yl)-P$^2$-[7-hydroxy-5-methoxy-4-methyl-phthalan-1-on-6-yl-(3'-methyloct-2'-ene-8'-yl)]methylenebis(phosphonate), P$^1$-(3'-fluoro-3'-deoxyinosin-5'-yl)-P$^2$-[7-hydroxy-5-methoxy-4-methyl-phthalan-1-on-6-yl-(3'-methylbut-2'-ene-4'-yl)]methylenebis(phosphonate), P$^1$-(3'-fluoro-3'-deoxyinosin-5'-yl)-P$^2$-[7-hydroxy-5-methoxy-4-methyl-phthalan-1-on-6-yl-(3'-methylpent-2'-ene-5'-yl)]methylenebis(phosphonate), P$^1$-(3'-fluoro-3'-deoxyinosin-5'-yl)-P$^2$-[7-hydroxy-5-methoxy-4-methyl-phthalan-1-on-6-yl-(3'-methylhex-2'-ene-6'-yl)]methylenebis(phosphonate), P$^1$-(3'-fluoro-3'-deoxyinosin-5'-yl)-P$^2$-[7-hydroxy-5-methoxy-4-methyl-phthalan-1-on-6-yl-(3'-methylhept-2'-ene-7'-yl)]methylenebis(phosphonate), P$^1$-(3'-fluoro-3'-deoxyinosin-5'-yl]-P$^2$-[7-hydroxy-5-methoxy-4-methyl-phthalan-1-on-6-yl-(3'-methyloct-2'-ene-8'-yl)]methylenebis(phosphonate), P$^1$-[9-(2'-fluoro-2'-deoxy-β-D-arabinofuranosyl)-hypoxanthin-5'-yl]-P$^2$-[7-hydroxy-5-methoxy-4-methyl-phthalan-1-on-6-yl-(3'-methylbut-2'-ene-4'-yl)]methylenebis(phosphonate), P$^1$-[9-(2'-fluoro-2'-deoxy-β-D-arabinofuranosyl)hypoxanthin-5'-yl]-P$^2$-[7-hydroxy-5-methoxy-4-methyl-phthalan-1-on-6-yl-(3'-methylpent-2'-ene-5'-yl)]methylenebis(phosphonate), P$^1$-[9-(2'-fluoro-2'-deoxy-β-D-arabinofuranosyl)hypoxanthin-5'-yl]-P$^2$-[7-hydroxy-5-methoxy-4-methyl-phthalan-1-on-6-yl-(3'-methylhex-2'-ene-6'-yl)]methylenebis(phosphonate), P$^1$-[9-(2'-fluoro-2'-deoxy-β-D-arabinofuranosyl)-hypoxanthin-5'-yl]-P$^2$-[7-hydroxy-5-methoxy-4-methyl-phthalan-1-on-6-yl-(3'-methylhept-2'-ene-7'-yl)]methylenebis(phosphonate), P$^1$-[9-(2'-fluoro-2'-deoxy-β-D-arabinofuranosyl)-hypoxanthin-5'-yl]-P$^2$-[7-hydroxy-5-methoxy-4-methylphthalan-1-on-6-yl-(3'-methyloct-2'-ene-8'-yl)]methylenebis(phosphonate), P$^1$-[9-(3'-fluoro-3'-deoxy-β-D-arabinofuranosyl)-hypoxanthin-5'-yl]-P$^2$-[7-hydroxy-5-methoxy-4-methyl-phthalan-1-on-6-yl-(3'-methylbut-2'-ene-4'-yl)]methylenebis(phosphonate), P$^1$-[9-(3'-fluoro-3'-deoxy-β-D-arabinofuranosyl)-hypoxanthin-5'-yl]-P$^2$-[7-hydroxy-5-methoxy-4-methyl-phthalan-1-on-6-yl-(3'-methylpent-2'-ene-5'-yl)]methylenebis(phosphonate), P$^1$-[9-(3'-fluoro-3'-deoxy-β-D-arabinofuranosyl)-hypoxanthin-5'-yl]-P$^2$-[7-hydroxy-5-methoxy-4-methyl-phthalan-1-on-6-yl-(3'-methylhex-2'-ene-6'-yl)]methylenebis(phosphonate), P$^1$-[9-(3'-fluoro-3'-deoxy-β-D-arabinofuranosyl)-hypoxanthin-5'-yl]-P$^2$-[7-hydroxy-5-methoxy-4-methyl-phthalan-1-on-6-yl-(3'-methylhept-2'-ene-7'-yl)]methylenebis(phosphonate), and P$^1$-[9-(3'-fluoro-3'-deoxy-β-D-arabinofuranosyl)-hypoxanthin-5'-yl]-P$^2$-[7-hydroxy-5-methoxy-4-methyl-phthalan-1-on-6-yl-(3'-methyloct-2'-ene-8'-yl)]methylenebis(phosphonate).

4. The compound of claim 1, wherein X is $CH_2$.

5. The compound of claim 1, wherein X is dihalomethylene.

6. The compound of claim 1, wherein $W_1$ is $NH_2$, NRH, or $NR_2$.

7. The compound of claim 1, wherein $W_2$ is H.

8. The compound of claim 1, wherein $W_2$ is $NH_2$, NRH, or $NR_2$.

9. The compound of claim 1, wherein $R_1$ and $R_2$ are OH, and $R_3$ and $R_4$ are H.

10. The compound of claim 1, wherein Y is OH.

11. The compound of claim 1, wherein n is 1.

12. The compound of claim 1, wherein n is 3.

13. The compound of claim 1, wherein X is $CH_2$, and $W_1$ and $W_2$ are $NH_2$, NRH, or $NR_2$, and $W_2$ is H.

14. The compound of claim 1, wherein X is $CH_2$, and $W_1$ and $W_2$ are $NH_2$, NRH, or $NR_2$, and $W_2$ is H.

15. The compound of claim 1, wherein X is dihalomethylene, W1 and $W_2$ are $NH_2$, NRH, or $NR_2$, and $W_2$ is H.

16. The compound of claim 1, wherein X is dihalomethylene, and $W_1$ and $W_2$ are $NH_2$, NRH, or $NR_2$.

17. The compound of claim 1, wherein X is $CH_2$, $R_1$ and $R_2$ are OH, and $R_3$ and $R_4$ are H.

18. The compound of claim 1, wherein X is dihalomethylene, $R_1$ and $R_2$ are OH, and $R_3$ and $R_4$ are H.

19. The compound of claim 1, wherein X is $CH_2$, $W_1$ is $NH_2$, NRH, or $NR_2$, $W_2$ is H, and n is 1.

20. The compound of claim 1, wherein X is $CH_2$, $W_1$ and $W_2$ are $NH_2$, NRH, or $NR_2$, and n is 1.

21. The compound of claim 1, wherein X dihalomethylene, $W_1$ is $NH_2$, NRH, or $NR_2$, $W_2$ is H, and n is 1.

22. The compound of claim 1, wherein X is dihalomethylene, $W_1$ and $W_2$ are $NH_2$, NRH, or $NR_2$, and n is 1.

23. The compound of claim 1, wherein X is $CH_2$, $W_1$ and $W_2$ are $NH_2$, NRH, or NR, and n is 3.

24. The compound of claim 1, wherein X is $CH_2$, $R_1$ and $R_2$ are OH, and $R_3$ and $R_4$ are H, and n is 1.

25. The compound of claim 1, wherein dihalomethylene, $R_1$ and $R_2$ are OH, and $R_3$ and $R_4$ are H, and n is 1.

26. The compound of claim 1, wherein X is $CH_2$, $R_1$ and $R_2$ are OH, and $R_3$ and $R_4$ are H, and n is 3.

27. The compound of claim 1, which is P$^1$-(Adenosin-5'-yl)-P$^2$-(mycophenol-5'-yl) methylenebis(phosphonate).

28. The compound of claim 1, which is P$^1$-(Adenosin-5'yl)-P$^2$-[7-hydroxy-5-methoxy-4methyphtalan-1-on-6yl-(3'-methylhex-2'-ene-6'-yl)]methylenebis-(phosphonate).

* * * * *